US011105818B2

(12) United States Patent
Su et al.

(10) Patent No.: US 11,105,818 B2
(45) Date of Patent: Aug. 31, 2021

(54) MIC-1 RECEPTOR AND USES THEREOF

(71) Applicant: Novo Nordisk A/S, Bagsvaerd (DK)

(72) Inventors: Jing Su, Beijing (CN); Wei Yang, Boston, MA (US); Chih-Chuan Chang, Beijing (CN); Li Yang, Beijing (CN); Zhe Sun, Beijing (CN); Haibin Chen, Ningbo (CN); Zhenhua He, Shanghai (CN); Zhe Wang, Beijing (CN); Sebastian Beck Joergensen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 35 days.

(21) Appl. No.: 16/069,985

(22) PCT Filed: Jan. 13, 2017

(86) PCT No.: PCT/EP2017/050695
§ 371 (c)(1),
(2) Date: Jul. 13, 2018

(87) PCT Pub. No.: WO2017/121865
PCT Pub. Date: Jul. 20, 2017

(65) Prior Publication Data
US 2019/0025332 A1    Jan. 24, 2019

(30) Foreign Application Priority Data
Jan. 15, 2016 (WO) ................ PCT/CN2016/071028

(51) Int. Cl.
*G01N 33/74* (2006.01)
*G01N 33/566* (2006.01)
*C07K 14/71* (2006.01)
*C12N 9/12* (2006.01)

(52) U.S. Cl.
CPC ............ *G01N 33/74* (2013.01); *C07K 14/71* (2013.01); *C12N 9/12* (2013.01); *C12Y 207/10001* (2013.01); *G01N 33/566* (2013.01); *G01N 2333/495* (2013.01); *G01N 2333/70575* (2013.01); *G01N 2500/02* (2013.01); *G01N 2500/10* (2013.01); *G01N 2500/20* (2013.01)

(58) Field of Classification Search
CPC ............ G01N 33/74; G01N 2333/495; G01N 2500/10; C07K 14/71; C12Y 207/10001
See application file for complete search history.

(56) References Cited

FOREIGN PATENT DOCUMENTS

| WO | 2005099746 A1 | 10/2005 |
| WO | 2006095446 A1 | 9/2006 |
| WO | 2013148117 A1 | 10/2013 |
| WO | 2014120619 A2 | 8/2014 |
| WO | 2014160811 A1 | 10/2014 |

OTHER PUBLICATIONS

Li et al., Targeting both sides of the GDF15-GFRAL-RET receptor complex: A new approach to achieve body weight homeostasis. Genese & Diseases 4: 183-184, 2017.*
Kim et al., "Macrophage Inhibitory Cytokine-1 Activates AKT and ERK-1/2 via the Transactivation of ErbB2 in Human Breast and Gastric Cancer Cells," Carcinogenesis, 2008, vol. 29, No. 4, pp. 704-712.
Li et al., "Identification, Expression and Functional Characterization of the GRAL Gene," J. Neurochem., 2005, vol. 95, pp. 361-376.
Takahashi, "The GDNF/RET Signaling Pathway and Human Diseases," Cytokine & Growth Factor Reviews, 2001, vol. 12, No. 4, pp. 361-373.
Bauskin et al., "The Propeptide of Macrophage Inhibitory Ctyokine (MIC-1), a TGF-? Superfamily Member, Acts as a Quality Control Determinant for Correctly Folded MIC-1," The EMBO Journal, 2000, vol. 19, No. 10, pp. 2212-2220.
Bootcov et al., "MIC-1, a Novel Macrophage Inhibitory Cytokine, is a Divergent Member of the TGF-beta Superfamily," Proc Natl Acad Sci USA, 1997, vol. 94, pp. 11514-11519.
Carlos F. Ibanez, "Beyond the Cell Surface: New Mechanisms of Receptor Function," Biochemical and Biophysical Research Communications, 2010, vol. 296, No. 1, pp. 24-27.
Jing et al., "GFRalpha-2 and GFRalpha-3 are Two New Receptors for Ligands of the GDNF Family," The Journal of Biological Chemistry, 1997, vol. 272, No. 52, pp. 33111-33117.
Johnen et al., "Tumor-Induced Anorexia and Weight Loss are Mediated by the TGF-beta Superfamily Cytokine MIC-1," Nat Med, 2007, vol. 13, pp. 1333-1340.
Jes Thom Clausen, "Ansogning om tilladelse til anvendelse af Genetisk Modificerede DYR, jfr. lov om kloning og genmodificering, i forbindelse med dyreforsog" ("Application for permission to use Genetically Modified Animals, ref. the Danish Act on Cloning and Genetic Engineering, in connection with experiments and testing involving animals." Nov. 20, 2015.

* cited by examiner

*Primary Examiner* — Ruixiang Li
(74) *Attorney, Agent, or Firm* — Leon Y. Lum

(57) ABSTRACT

The present invention relates to the newly identified MIC-1 binding receptor, GFRAL. In vitro bioassays, for testing affinity and potency of GFRAL ligand, such as MIC- or MIC-1 variants, are provided.

3 Claims, 20 Drawing Sheets
Specification includes a Sequence Listing.

MIC-1 RECEPTOR AND USES THEREOF

CROSS-REFERENCE TO RELATED APPLICATIONS

This application is a 35 U.S.C. § 371 National Stage application of International Application PCT/EP2017/050695 (WO 2017/121865), filed Jan. 13, 2017, which claims priority to Chinese Patent Application PCT/CN2016/071028, filed Jan. 15, 2016; the contents of which are incorporated herein by reference.

FIELD OF THE INVENTION

The present invention relates to assays for screening or evaluating GFRAL ligands, such as MIC-1 compounds. The present invention also relates to cell lines for determining the activity of GFRAL ligands.

BACKGROUND OF THE INVENTION

Weight and appetite control are complex. Its dysregulation can lead to obesity or anorexia.

Obesity is believed to be one of the principal factors responsible for the development of insulin resistance, impaired glucose homeostasis. There has been proposed several mechanisms linking obesity with type 2 diabetes such as ectopic lipid accumulation, low-grade chronic inflammation, endothelial dysfunction, leptin resistance, gut flora, impaired energy expenditure just to mention some. Interestingly, while the relative contributions from each of these factors remain uncertain, it is believed that many of these factors are either induced or accelerated with obesity. Thus, the most direct approach to prevent and treat newly diagnosed T2 diabetics is to reduce food intake and obesity.

At the other extreme, anorexia/cachexia is most commonly due to late stage cancer, where it is believed that tumor or stromal cell derived molecules disturb the control of appetite and weight, leading to wasting, debility and often death.

MIC-1 was first reported as a new member of the transforming TGF-β super-family in 1997, and it was named Macrophage Inhibitory Cytokine-1 (MIC-1). See Bootcov, M. R. et al. MIC-1, a novel macrophage inhibitory cytokine, is a divergent member of the TGF-β superfamily cluster. *Proc. Natl. Acad. Sci. USA* 94, 11514-11519 (1997).

Data in literature show that MIC-1 is not expressed under basal conditions but may be induced by inflammation, injury or malignancy. MIC-1 is overexpressed in many cancers, including those of the prostate, colon, pancreas and breast. In individuals with advanced cancer, serum MIC-1 can rise from a mean of 0.45 ng/ml to 5-50 ng/ml or higher. Tumor overproduction of MIC-1 and the correlation of serum MIC-1 levels with weight loss (in both animal models and in individuals with prostate cancer) suggest that MIC-1 is involved in the pathogenesis of cancer anorexia and weight loss and is perhaps involved in other cachectic conditions, such as those that are associated with renal and cardiac failure. The weight loss in animal model was reversed by treatment with MIC-1 antibody. MIC-1 also induced weight loss in massively obese leptin-deficient ob/ob mice. The studies in the literature show that MIC-1 is a regulator of appetite and weight, and it could be a therapeutic target for cancer anorexia, weight loss, obesity, and other conditions that are responsive to modulating the activity of MIC-1. See, for example, Breit S N et al. Tumor-induced anorexia and weight loss are mediated by the TGF-β superfamily cytokine MIC-1. Nat Med 2007; 13: 1333-1340. However, MIC-1's mechanism of action is not known.

SUMMARY OF THE INVENTION

In one aspect, the invention provides a method or an assay for testing or evaluating the activity of a GFRAL ligand. In one aspect, the invention provides a method or an assay for testing or evaluating the activity of a MIC-1 compound.

In a further aspect, the invention provides a cell-based assay or a cell line for detecting or evaluating the activity of a GFRAL ligand, such as a MIC-1 compound, wherein the cell expresses GFRAL ligand receptor on cell surface. The cell-based assay could be a proliferation assay, cytotoxicity assay, gene expression assay, a signal transduction assay, etc.

In another aspect, the invention provides a method or an assay for detecting or evaluating the binding affinity and selectivity of a GFRAL ligand, such as a MIC-1 compound, to GFRAL.

Also or alternatively, the invention provides a kit for measuring the activity and selectivity of a GFRAL ligand, such as a MIC-1 compound.

Also or alternatively, the invention provides a kit for measuring the binding affinity and selectivity of a GFRAL ligand, such as a MIC-1 compound.

BRIEF DESCRIPTION OF THE SEQUENCE LISTING

Figure 1:
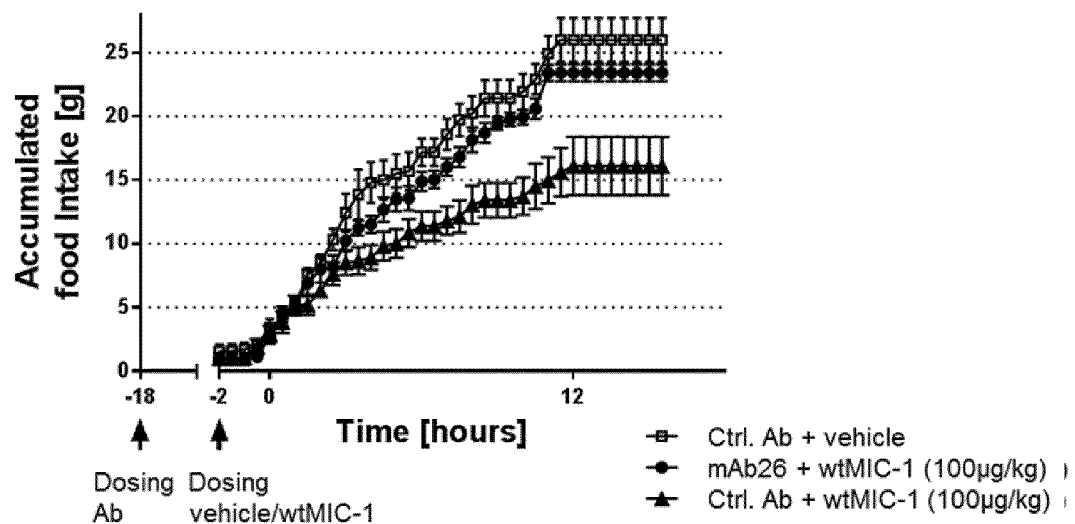
FIG. 1 shows that administration of mAb26 inhibited wtMIC-1's in vivo activity on suppressing food intake in sprague dawley male rats. Accumulated food intake was measured over 24 hrs in rats after SC administration of 200 µg/kg of wtMIC-1. Open Square: vehicle group pre-treated with isotype antibody. Black circle: wtMIC-1 group pre-treated with isotype antibody (control); Black triangle: wtMIC-1 group pre-treated with mAb26. Vehicle and wtMIC-1 was administrated SC and antibodies was administrated IP.

SEQ ID NO: 1 gives the DNA sequence of full length human GFRAL (hGFRAL). Residues 88-1272 is the sequence of coding sequence (CDS).

SEQ ID NO: 2 gives the amino acid sequence of the full length hGFRAL(hGFRAL(FL)). Residues 1-18 is the sequence of the signal peptide. Residues 19-351 is the sequence of the extracellular region (ECR). Residues 352-371 is the sequence of the transmembrane domain. Residues 372-394 is the sequence of the intracellular region (ICR).

SEQ ID NO: 3 gives the DNA sequence of mouse GFRAL isoform 1 (mGFRAL). Residues 196-1377 is the sequence of CDS.

SEQ ID NO: 4 gives the amino acid sequence of mGFRAL isoform1. Residues 1-19 is the sequence of the signal peptide. Residues 20-349 is the sequence of the extracellular region (ECR). Residues 350-370 is the sequence of the transmembrane domain. Residues 371-393 is the sequence of the intracellular region (ICR).

SEQ ID NO: 5 gives the amino acid sequence of human RET isoform 51 (hRET51). Residues 1-28 is the sequence of the signal peptide. Residues 29-636 is the sequence of the extracellular region (ECR). Residues 637-667 is the sequence of the transmembrane domain. Residues 668-1114 is the sequence of the intracellular region (ICR).

SEQ ID NO: 6 gives the amino acid sequence of hGFRAL_ECR-LC. Residues 1-16 is the sequence of the CD33 signal peptide. Residues 17-348 is the sequence of ECR of hGFRAL. Residues 349-358 is the sequence of the GGGGSGGGGS linker. Residues 359-577 is the sequence of mouse anti-TNP light chain (LC).

SEQ ID NO: 7 gives the amino acid sequence of hGFRAL_ECR-hIgG1.1_Fc. Residues 1-16 is the sequence of the CD33 signal peptide. Residues 17-340 is the sequence of ECR of hGFRAL. Residues 341-575 is the sequence of human IgG1.1_Fc (hIgG1.1_Fc).

SEQ ID NO: 8 gives the amino acid sequence of mGFRAL_ECR-LC. Residues 1-16 is the sequence of the CD33 signal peptide. Residues 17-345 is the sequence of ECR of mGFRAL. Residues 346-356 is the sequence of the GGGGSGGGGS linker. Residues 357-575 is the sequence of mouse anti-TNP light chain (LC).

SEQ ID NO: 9 gives the amino acid sequence of hGFRAL_C1-LC. Residues 1-16 is the sequence of the CD33 signal peptide. Residues 17-127 is the sequence of the C1 domain in ECR of hGFRAL. Residues 128-137 is the sequence of the GGGGSGGGGS linker. Residues 138-356 is the sequence of mouse anti-TNP light chain (LC).

SEQ ID NO: 10 gives the amino acid sequence of hGFRAL_C2-LC. Residues 1-16 is the sequence of the CD33 signal peptide. Residues 17-105 is the sequence of the C2 domain in ECR of hGFRAL. Residues 106-115 is the sequence of the GGGGSGGGGS linker. Residues 116-334 is the sequence of mouse anti-TNP light chain (LC).

SEQ ID NO: 11 gives the amino acid sequence of hGFRAL_C3-LC. Residues 1-16 is the sequence of the CD33 signal peptide. Residues 17-148 is the sequence of the C2 domain in ECR of hGFRAL. Residues 149-158 is the sequence of the GGGGSGGGGS linker. Residues 159-377 is the sequence of mouse anti-TNP light chain (LC).

SEQ ID NO: 12 gives the amino acid sequence of hGFRAL_C1C2-LC. Residues 1-16 is the sequence of the CD33 signal peptide. Residues 17-216 is the sequence of the C1 and C2 domains in ECR of hGFRAL. Residues 217-226 is the sequence of the GGGGSGGGGS linker. Residues 227-445 is the sequence of mouse anti-TNP light chain (LC).

SEQ ID NO: 13 gives the amino acid sequence of hGFRAL_C2C3-LC. Residues 1-16 is the sequence of the CD33 signal peptide. Residues 17-237 is the sequence of the C2 and C3 domains in ECR of hGFRAL. Residues 238-247 is the sequence of the GGGGSGGGGS linker. Residues 248-466 is the sequence of mouse anti-TNP light chain (LC).

SEQ ID NO: 14 gives the amino acid sequence of HC_TM (chimeric protein consisted of mouse anti-TNF fab heavy chain and PDGFR transmembrane region). Residues 1-18 is the sequence of the signal peptide of mouse Ig heavy chain. Residues 19-236 is the sequence of mouse anti-TNP fab heavy chain (HC). Residues 237-285 is the sequence of a fragment of human PDGFRB containing the transmembrane region. Residues 257-277 is the sequence of the PDGFRB transmembrane region (TM).

SEQ ID NO: 15 gives the amino acid sequence of HC_HPC4 (chimeric protein consisted of mouse anti-TNF fab heavy chain and HPC4 tag). Residues 1-18 is the sequence of the signal peptide of mouse Ig heavy chain. Residues 19-236 is the sequence of mouse anti-TNP fab heavy chain (HC). Residues 237-241 is the sequence of GGGGS linker. Residues 242-253 is the sequence of HPC4 tag (HPC4).

SEQ ID NO: 16 gives the amino acid sequence of wild type human MIC-1 (wtMIC-1).

SEQ ID NO: 17 gives the amino acid sequence of the full length human RET43.

SEQ ID NO: 18 gives the amino acid sequence of the full length human RET9.

SEQ ID NO: 19 gives the amino acid sequence of the full length mouse RET.

SEQ ID NO: 20 gives the amino acid sequence of the full length cyno GFRAL.

SEQ ID NO: 21 gives the amino acid sequence of the full length cyno RET.

SEQ ID NO: 22 gives the amino acid sequence of the full rat GFRAL.

SEQ ID NO: 23 gives the amino acid sequence of the full length rat RET.

DESCRIPTION OF THE INVENTION

The inventors of the present application surprisingly found that GFRAL is the cell surface receptor that mediates the in vivo activities of MIC-1. In particular, GFRAL binds to MIC-1 and then the complex of GFRAL and MIC-1 binds to RET to mediate activation of MIC-1.

In one aspect, the invention provides a cell-based potency assay to test the biological activity of a GFRAL ligand, comprising contacting an indicator cell with a test sample that comprises the GFRAL ligand, and then detecting a biological response of the indicator cell. The indicator cell expresses on the cell surface a GFRAL ligand binding receptor comprising a GFRAL ligand binding segment derived from GFRAL. In one embodiment, the GFRAL ligand is a MIC-1 compound, and GFRAL ligand binding receptor is MIC-1 binding receptor that comprises a MIC-1 binding segment derived from GFRAL.

As used herein, "potency" is a measure of substance's biological activity of a substance that elicits or produces a defined biological response. In the pharmaceutical area, potency is a measure of the biological activity of a drug product that produces a defined clinical effect.

As used herein, "biological activity" is the ability of a molecule to effect a change in a biological process. Here, biological activity, bioactivity, functional activity, and function are interchangeable. Characterization of a biological product includes the determination of physicochemical properties, biological activity, immunochemical properties, purity and impurities, etc. Cell culture based or cell-based potency assays are often the preferred format for determining the biological activity of a biological product, since they can measure the biological response elicited by the product and can generate results within a relatively short period of time, comparing with animal based assays. Also, lots of cell-based potency assays have defined correlation with the drug product's mechanism of action. Thus, such assays are widely used and required by drug administration authorities for drug registration and release.

Cells are living entities, representing biological systems that possess many of the important in vivo characteristics that make them useful for measuring biological activity. Such cell-based assays is capable of being used for characterization, lot release, in-process and stability testing for drugs. Such assays can provide a basis for assessing product comparability before and after manufacturing changes. They can evaluate product stability (e.g., expiry dating), and control clinical dosing consistency. Other uses of cell-based assays include qualification of internal reference materials; characterization of process intermediates, formulations, and degradation products, etc.

In one aspect of the invention, indicator cell line is from a cell lineage close to the cell or tissue type targeted by MIC-1 compounds in vivo. In another aspect of the invention, it is a cell line expressing an appropriate MIC-1 compound binding receptor on the cell surface, either endogenously or exogenously via transfection. In one embodiment, the indicator cell is derived from neuron cells. In a further embodiment, the indicator cell is derived from hypothalamus or brain stem. In yet another embodiment, the indicator cell is derived from arcuate nucleus (ARC), paraventricular nucleus (PVN), area postrema (AP), or nucleus tractus solitarus (NTS). In a further embodiment, the indicator cells are derived from neuron cells, e.g. cells derived from ARC, PVN, AP, NTS, express the MIC-1 binding receptor endogenously. In yet another embodiment, indicator cell is derived from arcuate nucleus (ARC), paraventricular nucleus (PVN), area postrema (AP), or nucleus tractus solitarus (NTS) express the MIC-1 binding receptor exogenously via transfection or transformation with a construct or vector. In another embodiment, the indicator cell is a cell transfected or transformed with a construct or vector to exogenously express the MIC-1 binding receptor on the cell surface. The transformed or transfected cells can be prokaryotes, or eukaryotes. Prokaryotes include gram negative bacteria and gram positive bacteria. The indicator cell can also be yeast cells or animal cells. In an embodiment, the animal cell is originated from non-mammalian animal, e.g., insects or birds. In another embodiment, the animal cell is originated from mammalian animal, e.g., human, primates, and rodents. In a further embodiment, the indicator cell is BHK21, PC-12, HEK293, 3T3-L1, CHO, HTC-116, PC3, or Caco2.

"Construct" is interchangeable with "vector" in this document, which refers to an artificially assembled DNA segment to be transferred into a cell line, target tissue, or animal. Construct or vectors, as used herein, include plasmid, virus, bacteriophage, integratable DNA fragments (i.e., fragments integratable into the host genome by genetic recombination), and other vehicles which enable the integration of DNA fragments comprising a gene or a nucleic acid sequence of interest. Typically, the construct comprises control elements and a gene or a nucleic acid sequence encoding MIC-1 binding receptor. Generally, the control elements include a promoter system, an operator to control the level of mRNA expression, a sequence encoding a ribosome binding site, a sequence terminating transcription and translation, etc.

The term "biological response" as used herein means a response of the indicator cell elicited by the molecules to be tested, e.g., GFRAL ligand (such as MIC-1 compound). Biological responses include any responses related to for example cell proliferation, validity, growth arrest, cell death (e.g. apoptosis), motility, morphology, toxicity, gene transcription (e.g. reporter genes), protein expression, cytokine release, phosphorylation of a kinase, or activation or inactivation of any components of a signaling pathway, metabolism, etc.

In one embodiment, the biological response is up-regulating or down-regulating a gene transcription. In a further embodiment, the up-regulated gene is c-fos. In another embodiment, the up-regulated gene is a gene of an appetite regulating neuro-peptide. In a further embodiment, the appetite regulating neuro-peptide is POMC (pro-opiomelanocortin), CART (cocaine and amphetamine regulated transcript), NPY (neuropeptide Y), or AGRP (agouti-related protein). In yet a further embodiment, the mRNA of POMC and/or CART is increased. In yet another embodiment, the mRNA of NYP and/or AGRP is decreased. In yet another embodiment, the up-regulated gene transcription is an indicator of signaling pathway activation. In a further embodiment, transcription of GLI, MEF2, SRE, FOXO is upregulated.

In one embodiment, the biological response is related to signal transduction. Cell signaling or signal transduction is a part of a communication system that governs cellular activities and coordinates cell actions. Through such communication systems including signal transduction, cells are able to perceive and respond to the changes in the surrounding microenvironment.

In one embodiment, the signal transduction related biological response is an increase or decrease of phosphorylation of a protein kinase. In a further embodiment, the signal transduction related biological response is an increase or decrease of phosphorylation of RET, ERK1/2, AKT1/2/3, STAT(s), etc. One major mechanism for signal transduction in animals involves protein phosphorylation. Protein phosphorylation involves the action of protein kinase, an enzyme that transfers a phosphate group from a phosphate donor onto an acceptor amino acid in a substrate protein. Protein kinases can be classified based on the acceptor amino acid specificity. The two most well characterized types of protein kinases are protein serine/threonine kinases (a protein kinase with a protein alcohol group as acceptor) and protein tyrosine kinases (a protein kinases with a protein phenolic group as acceptor).

Various assays have been developed for measuring the phosphorylation of serine/threonine kinases and tyrosine kinases. Some of these assays measure the ability of a tyrosine kinase or serine/threonine kinase to phosphorylate a synthetic substrate polypeptide. See Pike, L., Methods of Enzymology 146:353-362 (1987) and Hunter, Journal of Biological Chemistry 257(9):4843-4848 (1982). Wang et al., Journal of Biological Chemistry 267(24):17390-17396 [1992]. Such assays can use radioactive labels. The discovery of phospho-specific antibodies against phosphorylated of tyrosine/serine/threonine residues or against a specific phosphorylated protein kinase enables immunology assays measuring phosphorylation of protein kinases, such as ELISA.

In another embodiment, the biological response detected is an increase or decrease of the level of a second messenger.

Except for protein phosphorylation, second messengers usually are also involved in intracellular signal transduction. Second messengers are signaling molecules released by the cell to trigger physiological changes such as proliferation, differentiation, migration, survival, and apoptosis, etc. Examples of second messenger molecules include cyclic AMP, cyclic GMP, inositol triphosphate, diacylglycerol, and calcium. In one embodiment, the second messenger is coupled to phosphorylation of a protein kinase. For example, Ras and GTP link with the Mitogen Activated Protein Kinase (MAPK) cascade.

GFRAL is the abbreviation of "GDNF family receptor alpha like". Human GFRAL was described in WO 03/076569. Mouse GFRAL was described by Li Z, et al. in Identification, expression and functional characterization of the GRAL gene, *J Neurochem,* 2005 October. Sequence analysis suggests that GFRAL is a remote homolog of GFRα1-4 (GDNF family receptor alpha 1-4).

"GFRAL ligand" as used herein means a ligand (a compound) that binds to the GFRAL receptor. "GFRAL ligand" can be an antagonist or against of GFRAL receptor. In one embodiment, GFRAL ligand is an antibody, e.g. an antagonistic antibody or agonistic antibody. In another embodiment, GFRAL ligand is a MIC-1 compound.

The term "MIC-1 compound" as used herein means MIC-1 of mammalian origin, such as human, monkey, rat, mouse, etc., and recombinant MIC-1, such as recombinant human, monkey, rat, mouse MIC-1, and a MIC-1 variant. A MIC-1 variant means a variant that retains MIC-1 activity. MIC-1 variant could be a truncated MIC-1, a MIC-1 analogue or a MIC-1 derivative. As used herein "MIC-1" and "MIC-1 compound" are interchangeable. A truncated MIC-1 is a fragment of wild type MIC-1. A MIC-1 analogue means a modified MIC-1 wherein one or more amino acid residues of wild type MIC-1 have been substituted with other natural or unnatural amino acid residues and/or wherein one or more natural or unnatural amino acid residues have been deleted from wild type MIC-1 and/or wherein one or more natural or unnatural amino acid residues have been added to wild type MIC-1 and any combinations thereof. MIC-1 derivative means a chemically modified wild type MIC-1 with or without substituting, adding or deleting one or more natural or unnatural amino acid residues, wherein at least one substituent is not present in wild type MIC-1. Typical modifications include amides, carbohydrates, alkyl groups, acyl groups, esters, PEGylations and the like.

In some embodiments, the MIC-1 compound has at least 80% sequence identity or homology with wild type MIC-1. In some embodiments, the MIC-1 compound has at least 10% of the wild type MIC-1 activity. "Identity" and "homology" are interchangeable in this document. In some embodiments, the MIC-1 has at least 80% identity with wild type human MIC-1 and at least 10% of the activity of the wild type human MIC-1. In a further embodiment, MIC-1 represents a MIC-1 compound comprising an amino acid sequence having at least 90% identity to the amino acid sequence of human MIC-1. In further embodiments, MIC-1 has at least 80%, at least 85%, at least 95%, at least 96%, at least 97%, at least 98% or at least 99% identity with human MIC-1. In further embodiments, MIC-1 has at least 10%, at least 20%, at least 30%, at least 40%, at least 50%, at least 60%, at least 70%, at least 80%, or at least 90% of the MIC-1 activity of human MIC-1.

"GFRAL variant" as used herein means a GFRAL variant that retains MIC-1 binding affinity of wtGFRAL. A GFRAL variant could be a truncated GFRAL, a GFRAL analogue or a GFRAL derivative. A truncated GFRAL is a fragment of wild type GFRAL. In one embodiment, a truncated GFRAL comprises C1 and C2 domains of GFRAL. A GFRAL analogue means a modified GFRAL wherein one or more amino acid residues of wild type GFRAL have been substituted with other natural or unnatural amino acid residues and/or wherein one or more natural or unnatural amino acid residues have been deleted from wild type GFRAL and/or wherein one or more natural or unnatural amino acid residues have been added to wild type GFRAL and any combinations thereof. GFRAL derivative means a chemically modified wild type GFRAL with or without substituting, adding or deleting one or more natural or unnatural amino acid residues, wherein at least one substituent is not present in wild type GFRAL. Typical modifications include amides, carbohydrates, alkyl groups, acyl groups, esters, PEGylations and the like.

In some embodiments, the GFRAL variant has at least 80% sequence identity or homology with the MIC-1 binding domain of the extracellular region of wtGFRAL, and retains at least 10% of the MIC-1 binding affinity of wtGFRAL. In a further embodiment, the GFRAL variant has at least 85%, at least 90%, at least 91%, at least 92%, at least 93%, at least 94%, at least 95%, at least 96%, at least 97%, s at least 98%, at least 99% or 100% sequence identity with the MIC-1 binding domain of the extracellular region of wild type hGFRAL, and retains at least 10% of the MIC-1 binding affinity of wild type hGFRAL. In further embodiments, the GFRAL variant retains such as at least 20%, such as at least 40%, such as at least 60%, such as at least 80% of the MIC-1 binding affinity of wild type hGFRAL.

"GFRAL ligand binding receptor" as used herein means a receptor comprising an extracellular region, which comprises a GFRAL ligand binding segment that is derived from the GFRAL ligand binding domain in the extracellular region of GFRAL. In a further embodiment, GFRAL is derived from mammalian origin, such as human, monkey, rat, mouse, rabbit, etc. In one embodiment, the GFRAL ligand binding receptor further comprises a transmembrane region and an intracellular region. In a further embodiment, the intracellular region comprises a domain for effecting a response or change in the cytoplasm. In yet a further embodiment, the intracellular region comprises a catalytic domain. In one embodiment, a GFRAL ligand binds to the GFRAL ligand binding receptor in such a way that the conformation of the intracellular region of the receptor molecule changes, and such change activates or inhibits the enzymatic activity of the catalytic domain in the intracellular region. In another embodiment, a GFRAL ligand binds to the GFRAL ligand binding receptor in such a way that changes the conformation of whole receptor molecule, and such change triggers formation of a cluster/complex of GFRAL ligand, GFRAL ligand binding receptor with another receptor, so that a response or change in the cytoplasm is elicited. Preferably the other receptor is a cell surface receptor.

"MIC-1 binding receptor" as used herein means a receptor comprising an extracellular region, which comprises a MIC-1 binding segment that is derived from the MIC-1 binding domain in the extracellular region of GFRAL. In a further embodiment, GFRAL is derived from mammalian origin, such as human, monkey, rat, mouse, rabbit, etc. In one embodiment, the MIC-1 binding receptor further comprises a transmembrane region and an intracellular region. In a further embodiment, the intracellular region comprises a domain for effecting a response or change in the cytoplasm. In yet a further embodiment, the intracellular region comprises a catalytic domain. In one embodiment, a MIC-1 compound binds to the MIC-1 binding receptor in such a way that the conformation of the intracellular region of the receptor molecule changes, and such change activates or inhibits the enzymatic activity of the catalytic domain in the intracellular region. In another embodiment, a MIC-1 compound binds to the MIC-1 binding receptor in such a way that changes the conformation of whole receptor molecule, and such change triggers formation of a cluster/complex of MIC-1, MIC-1 binding receptor with another receptor, so that a response or change in the cytoplasm is elicited. Preferably the other receptor is a cell surface receptor.

In one embodiment of the invention, the "MIC-1 binding receptor comprising a MIC-1 binding segment derived from GFRAL" is a full length wild type GFRAL of mammalian origin, such as human, monkey, rat, mouse, rabbit, etc. MIC-1 binding receptor can also be allelic variations, natural mutants of GFRAL, or a protein encoded by DNA which hybridise under high or low stringency conditions to nucleic acids which encode GFRAL, etc.

In another embodiment of the invention, "MIC-1 binding receptor comprising a MIC-1 binding segment derived from GFRAL" is a GFRAL derived receptor, which is a modified GFRAL wherein one or more amino acid residues of wild type GFRAL have been substituted, deleted and/or wherein one or more natural or unnatural amino acid residues have been added, and such modified GFRAL comprises a MIC-1 binding segment derived from the MIC-1 binding domain of GFRAL and retains MIC-1 binding ability. In one embodiment, the MIC-1 binding segment of the MIC-1 binding receptor is derived from the MIC-1 binding domain of hGFRAL.

In another embodiment, MIC-1 binding receptor is a fusion protein, wherein the extracellular region comprises a MIC-1 binding segment derived from GFRAL. In one embodiment, the MIC-1 binding receptor comprises the extracellular region of GFRAL and an intracellular region of another receptor. In a further embodiment, the intracellular region comprises a catalytic domain.

In some embodiments, the MIC-1 binding domain of the extracellular region of a GFRAL derived receptor has at least 80% sequence identity or homology with the MIC-1 binding domain of the extracellular region of wtGFRAL, and retain at least 10% of the MIC-1 binding affinity of wtGFRAL. In a further embodiment, the MIC-1 binding segment has at least 85%, at least 90%, at least 91%, at least 92%, at least 93%, at least 94%, at least 95%, at least 96%, at least 97%, s at least 98%, at least 99% or 100% sequence identity with the MIC-1 binding domain of the extracellular region of wild type hGFRAL, and typically at least 10% of the MIC-1 binding affinity of wild type hGFRAL. In further embodiments, said identities to the MIC-1 binding domain of the extracellular region of wild type hGFRAL are coupled to at least 10%, such as at least 20%, such as at least 40%, such as at least 60%, such as at least 80% of the MIC-1 binding affinity of wild type hGFRAL.

The inventors of the present application surprisingly found that although GFRAL is a cell surface receptor that binds to MIC-1, in order to mediate MIC-1 activity, further binding of the complex of GFRAL and MIC-1 to RET is needed. As demonstrated in the examples, MIC-1 did not induce downstream signals in cells expressing GFRAL only or RET only, but MIC-1 signaled in cells expressing both GFRAL and RET. Without being bound to theory, it is believed that the in vivo activity of MIC-1 is mediated through both GFRAL and RET by forming a ternary complex.

RET is an abbreviation for "rearranged during transfection", as the DNA sequence of this gene was originally found to be rearranged within a 3T3 fibroblast cell line following its transfection with DNA taken from human lymphoma cells. The natural alternative splicing of the human RET gene results in the production of 3 different isoforms of the protein RET: RET51, RET43 and RET9. These three isoforms share the same 1063 amino acids in their N-terminal, but then contain 51, 43 and 9 different amino acids in their C-terminal at the cytoplasmic side respectively. Experiment results described below show that the activity of MIC-1 is only mediated by human RET51.

Similarly for mouse, rat, and cynomolgus, there are also isoforms of RET in each species. In mouse, they were also defined as Ret9 and Ret51. Experimental results of the invention showed that the activity of MIC-1 is mediated by the mouse, rat or cynomolgus homologs of human RET51.

The term "identity" or "homology" refers to a relationship between the sequences of two or more proteins, as determined by comparing the sequences. In the art, "identity" also means the degree of sequence relatedness between proteins, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins is capable of being readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993.

In one embodiment, results of cell-based potency assays are typically expressed as the 'relative potency' when compared to a reference standard or reference compound. The use of relative potency allows direct comparison between the molecules to be tested and the reference compound within the same assay, therefore reducing the impact of run-to-run variability on final reportable results.

In cell-based potency assays, a reference compound is usually used to assign relative potency, ensuring the measurement of potency is normalized over various compounds to be tested. As used herein, "reference compound" in a GFRAL ligand potency assays refers to a GFRAL ligand with known biological activity. For example, such GFRAL ligand can be a MIC-1 compound with known MIC-1 biological activity. In one embodiment of the invention, a reference compound is a wild type GFRAL ligand, for example, a wild type MIC-1 of mammalian origin, such as human, monkey, rat, mouse, etc., and a recombinant wild type MIC-1, such as recombinant human, monkey, rat, mouse MIC-1. In another embodiment of the invention, a reference compound is a variant, analogue, or derivative of the wild type GFRAL ligand with known biological activity, for example, a MIC-1 variant, analogue, or derivative, wherein the biological activity of such MIC-1 variant, analogue, or derivative is already known. In a further embodiment, the reference material is a representative batch of commercial MIC-1 compound for therapeutic use. In one embodiment of the invention, the indicator cells are grown in culture plates and stimulated with the reference compound and the GFRAL ligand to be tested respectively over a range of concentrations. In a further embodiment of the invention, the range of concentrations covers the whole dose response range from 0 to a maximal concentration. In yet a further embodiment, the whole dose response curve is in a sigmoidal shape.

In another aspect, the invention provides an assay or method for detecting the binding affinity of a GFRAL ligand. In a particular aspect, the invention provides an assay or method for detecting the binding affinity of a MIC-1 compound.

The term "binding affinity" is herein used as a measure of the strength of a noncovalent interaction between two molecules, such as a ligand (e.g., MIC-1 compound) and its receptor (MIC-1 binding receptor). Binding of a ligand (agonist or antagonist) to its receptor is the initial step in reactions that cause a biological or pharmacological effect. Binding assays is capable of being used in many ways. For example, they I used for screening of new chemical entities and also for the discovery of endogenous ligands. Such assays can also be used in a quantitative way to determine an unknown amount of analyte that is present in a test sample. They can also be used to study the receptor itself, such as identifying receptor subtypes or variants or determining the in vivo distribution of the receptor.

Binding affinity can be quantified by determination of the dissociation constant ($K_D$). In turn, $K_D$ can be determined by measurement of the kinetics of complex formation and dissociation, e.g. by the SPR method (Biacore). The rate constants corresponding to the association and the dissociation of a monovalent complex are referred to as the association rate constants $k_a$ and dissociation rate constant $k_d$, respectively. $K_D$ is related to $k_a$ and $k_d$ through the equation $K_D = k_d/k_a$. $K_D$ is inversely proportional to the ligand's binding affinity to the receptor.

Binding affinities associated with different molecules, e.g. the binding affinities of different MIC-1 compounds, may be compared by comparison of the $K_D$ values for the individual ligand, e.g., MIC-1 compound.

Similarly, the specificity of an interaction between two molecules (e.g., a MIC-1 compound and a MIC-1 binding protein) may be assessed by determination and comparison of the $K_D$ value for the interaction of interest, e.g. a specific interaction between a MIC-1 compound and the MIC-1 binding protein, with the $K_D$ value of an interaction not of interest.

Competitive assays are widely used for binding assays, where the receptor is contacted with a labeled ligand having known binding affinity to the receptor and a test analyte whose binding affinity to the receptor is being measured or detected. The bound ligands and the free ligands are then separated to detect or measure the binding. The amount of the bound test compound is inversely proportional to the amount of bound labeled ligand.

In one embodiment, the binding assay or method comprises contacting a test sample comprising the GFRAL ligand with a GFRAL ligand binding protein, and then detecting the binding of the GFRAL ligand to the GFRAL ligand binding protein, wherein the GFRAL ligand binding protein comprises a GFRAL ligand binding segment derived from GFRAL. In another embodiment, such assay or method comprises contacting a test sample comprising a reference compound and the GFRAL ligand to be tested with a GFRAL ligand binding protein, then detecting the binding of the reference compound to the GFRAL ligand binding protein, wherein the reference compound is a different GFRAL ligand with known binding affinity and is labeled for detection. In a further embodiment, the relative binding affinity of the GFRAL ligand is calculated based on the binding of the reference compound.

In a further embodiment, the binding assay or method comprises contacting a test sample comprising the MIC-1 compound with a MIC-1 binding protein, and then detecting the binding of the MIC-1 compound to the MIC-1 binding protein, wherein the MIC-1 binding protein comprising a MIC-1 binding segment derived from GFRAL. In another embodiment, such assay or method comprises contacting a test sample comprising a reference compound and the MIC-1 compound to be tested with a MIC-1 binding protein, then detecting the binding of the reference compound to the MIC-1 binding protein, wherein the reference compound is a different MIC-1 compound with known binding affinity and is labeled for detection. In a further embodiment, the relative binding affinity of the MIC-1 compound is calculated based on the binding of the reference compound.

"GFRAL ligand binding protein comprising GFRAL ligand binding segment derived from GFRAL" can be any form of protein that comprises a GFRAL ligand binding segment derived from GFRAL. In one embodiment, it could a GFRAL receptor. In another embodiment, the GFRAL ligand binding protein comprises a tag, e.g., HPC4, Fc, Fab, polyhistidine-tag, antibody light chain, etc. In one embodiment, the GFRAL ligand binding protein is soluble. In another embodiment, the GFRAL ligand binding protein is anchored on a solid phase or a cell surface. In a further embodiment, the solid phase is a plate or a bead. In a further embodiment, the cell is immobilized. In one embodiment, the GFRAL ligand binding protein comprises the extracellular region of wild type hGFRAL or mGFRAL. In one embodiment, the GFRAL ligand binding protein comprises a reporter peptide, except for the GFRAL ligand binding segment derived from GFRAL. In a further embodiment, the reporter peptide is luciferase, bacterial β-galactosidase, trpE, Protein A, β-lactamase, alpha amylase, alcohol dehydrogenase, yeast alpha mating factor, etc.

"MIC-1 binding protein comprising MIC-1 binding segment derived from GFRAL" can be any form of protein that comprises a MIC-1 binding segment derived from GFRAL. In one embodiment, it could a MIC-1 receptor. In another embodiment, the MIC-1 binding protein comprises a tag, e.g., HPC4, Fc, Fab, Fab-HPC4, polyhistidine-tag, antibody light chain, etc. In one embodiment, the MIC-1 binding protein is soluble. In another embodiment, the MIC-1 binding protein is anchored on a solid phase or a cell surface. In a further embodiment, the solid phase is a plate or a bead. In a further embodiment, the cell is immobilized. In one embodiment, the MIC-1 binding protein comprises the extracellular region of wild type hGFRAL or mGFRAL. In one embodiment, the MIC-1 binding protein comprises a reporter peptide, except for the MIC-1 binding segment derived from GFRAL. In a further embodiment, the reporter peptide is luciferase, bacterial β-galactosidase, trpE, Protein A, β-lactamase, alpha amylase, alcohol dehydrogenase, yeast alpha mating factor, etc.

In GFRAL ligand binding assays, "reference compound" refers to a GFRAL ligand with known binding affinity to GFRAL ligand binding receptor. In one embodiment of the invention, the reference compound used in binding assay is a wild type GFRAL ligand of mammalian origin, such as human, monkey, rat, mouse, etc., and a recombinant wild type GFRAL ligand, such as recombinant human, monkey, rat, mouse GFRAL ligand. In another embodiment of the invention, a reference compound used in binding assay is a GFRAL ligand variant, analogue, or derivative, wherein the binding affinity of such GFRAL ligand variant, analogue, or derivative is already known.

In an embodiment, the GFRAL ligand is MIC-1 compound. In MIC-1 compound binding assays, "reference compound" refers to a MIC-1 compound with known binding affinity to MIC-1 binding receptor. In one embodiment of the invention, the reference compound used in binding assay is a wild type MIC-1 of mammalian origin, such as human, monkey, rat, mouse, etc., and a recombinant wild type MIC-1, such as recombinant human, monkey, rat, mouse MIC-1. In another embodiment of the invention, a reference compound used in binding assay is a MIC-1 variant, analogue, or derivative, wherein the binding affinity of such MIC-1 variant, analogue, or derivative is already known.

Labels are widely used in binding assays. In one embodiment, the labels can be detected directly. For example, such directly detectable label a radio-isotopic label, a label detected by colorimetric detection system, a label detected by fluorescence detection system, a label detected by luminescence detection system, etc. In a further embodiment, the detectable label is $^3$H, $^{125}$I or $^{32}$P. In another further embodiment, the detectable label is tetramethylbenzidine (TMB), fluorescein, Alexa Fluor dyes, Bodipy FL-propionic acid, methoxycoumarin-COOH, CyDyes, Dansyl-SE, Fluorescein, NBD-SE, Rhodamine Green-SE, Texas Red-SE, Europium-chloride.6H$_2$O, luminol, lucigenin, luciferin, etc.

In another embodiment, the labels cannot be detected directly, but can facilitate binding of the labelled ligand to a binding partner that is labeled with a directly detectable label. In a further embodiment, such binding facilitating label is biotin, digoxin, HPC4, etc.

Ligand-receptor binding can be detected by many technologies. Some technologies require using a label. Some technologies are label-free. For example, binding can be detected by SPA (scintillation proximity assay), TRF (time-resolved fluorescence), FRET (fluorescence resonance energy transfer), BRET (bioluminescence resonance energy transfer), TR-FRET (time-resolved fluorescence resonance energy transfer), FP (fluorescence polarization), FMAT (fluorometric microvolume assay technology), AlphaScreen™, flow cytometry, FCS (fluorescence correlation spectroscopy), SPR (surface plasmon resonance), ForteBio, or TIRF (total internal reflection fluorescence), etc. Please see L. A. A. deJong et al., Receptor-ligand binding assays: Technologies and Applications, J. Chromatogr. B 829 (2005) 1-25.

The foregoing descriptions and the following list of embodiments are non-limiting to the invention:

Embodiment 1: A method for determining the activity of a GFRAL ligand, such as a MIC-1 compound, comprising:

(a) contacting an indicator cell with a test sample that comprises the GFRAL ligand, such as a MIC-1 compound; and (b) detecting a biological response of the indicator cell contacted with the test sample;

wherein the indicator cell expresses on the cell surface a MIC-1 binding receptor comprising the MIC-1 binding segment derived from GFRAL.

Embodiment 2: The method of embodiment 1, wherein the GFRAL ligand is a MIC-1 compound, and wherein the indicator cell further expresses a cell surface receptor kinase, and the biological response is induced when the MIC-1 compound, the MIC-1 compound binding receptor, and the cell surface receptor kinase form a ternary complex.

Embodiment 3: The method of embodiment 2, wherein the cell surface receptor kinase is RET receptor tyrosine kinase.

Embodiment 4: The method according to any one of embodiments 1-3, wherein GFRAL is derived from human, mouse, rat, rabbit or cynomolgus.

Embodiment 5: The method according to any one of embodiments 1-4, wherein the indicator cell also expresses a reporter peptide, such as luciferase, bacterial β-galactosidase, trpE, Protein A, β-lactamase, alpha amylase, alcohol dehydrogenase, yeast alpha mating factor, etc.

Embodiment 6: The method of according to any one of embodiments 1-5, wherein the indicator cell exogenously expresses the MIC-1 binding receptor, and/or the cell surface receptor kinase.

Embodiment 7: The method of embodiment 6, wherein the indicator cell is a mammalian cell.

Embodiment 8: The method of embodiment 7, wherein the indicator cell is BHK21 cell, PC-12 cell, HEK293 cell, or HEK293 cell stably expressing the tetracycline (Tet) repressor.

Embodiment 9: The method according to any one of embodiments 1-8, wherein the MIC-1 binding receptor is full length GFRAL.

Embodiment 10: The method according to any one of embodiments 1-8, wherein the MIC-1 binding receptor comprises the extracellular region of GFRAL.

Embodiment 11: The method of embodiment 1 or 2, wherein the biological response is related to signal transduction.

Embodiment 12: The method of embodiment 11, wherein the signal transduction related biological response is increase or decrease of a protein kinase phosphorylation, transcription of a gene or expression of a protein.

Embodiment 13: The method of embodiment 12, wherein the protein kinase is the cell surface receptor kinase or an intracellular protein kinase.

Embodiment 14: The method of embodiment 13, wherein the signal transduction related biological response is related to activation of Hedgehog pathway, MEF2 pathway, Smad pathway, ERK/MAPK pathway, JNK/p38 pathway, Small GTPase pathway, PI3K/Akt pathway, PLC-γ pathway, JAK/STAT pathway, Src-family kinases, CDK5 (cyclin-dependent kinase 5), Src-like kinase Fyn, FAK (focal adhesion kinase), and a combination thereof.

Embodiment 15: The method of embodiment 14, wherein the signal transduction related biological response is increased or decreased phosphorylation of a protein kinase of ERK/MAPK pathway.

Embodiment 16: The method of embodiment 15, wherein the protein kinase is selected from a group consisting of ERK1/2, MAP3K, Ras, MEK, Shc, c-Raf, or a combination thereof. Embodiment 17: The method of embodiment 14, wherein the signal transduction related biological response is increased or decreased phosphorylation of a protein kinase of PI3K/Akt pathway.

Embodiment 18: The method of embodiment 17, wherein the protein kinase is selected from the group consisting of PI3K (phosphoinositide 3-kinase), Akt1/2/3, mTOR (mammalian target of rapamycin), 4E-BP1 (4E-binding protein 1), S6 kinase, c-Ab1, and a combination thereof.

Embodiment 19: The method of embodiment 14, the signal transduction related biological response is increased or decreased phosphorylation of a protein kinase of Smad pathway, wherein the protein kinase could be selected from the group consisting of Smad1, Smad2, Smad3, Smad5, Smad8, and a combination thereof.

Embodiment 20: The method of embodiment 14, wherein the signal transduction related biological response is increased or decreased phosphorylation of a protein kinase of JNK/p38 MAPK pathway, wherein the protein kinase could be selected from a group consisting of MKK3, MKK4, MKK6, JNK, p38 MAPK, TAK1, TRAF6, and a combination thereof.

Embodiment 21: The method of embodiment 14, wherein the signal transduction related biological response is increased or decreased phosphorylation of a protein kinase of Small GTPase pathway, wherein the protein kinase could be selected from the group consisting of RhoA, Rac, Cdc42, and a combination thereof.

Embodiment 22: The method of embodiment 14, wherein the signal transduction related biological response is increased or decreased phosphorylation of a protein kinase of JAK/STAT pathway, wherein the protein kinase is selected from the group consisting of JAK1, JAK2, JAK3, TYK2, STAT1, STAT2, STAT3, STAT5 and a combination thereof. Embodiment 23: The method of embodiment 14, wherein the signal transduction related biological response is up-regulated or down-regulated transcription of a gene or expression a protein of Hedgehog pathway, wherein the gene or protein could be GLI.

Embodiment 24: The method of embodiment 14, wherein the signal transduction related biological response is up-regulated or down-regulated transcription or a gene or expression of a protein of MEF2 pathway, wherein the gene or protein could be MEF2.

Embodiment 25: The method of embodiment 21, wherein the increase or decrease of phosphorylation is determined by the phosphorylation level of the protein kinase; or is determined by the activity level of the reporter peptide, wherein the activity level of the reporter peptide is associated with the phosphorylation level of the protein kinase.

Embodiment 26: The method of embodiment 25, wherein the reporter peptide is luciferase.

Embodiment 27: The method of embodiment 25, wherein the phosphorylation of a protein kinase is measured by a process comprising:
(a) lysing the indicator cell to obtain cell lysate;
(b) exposing the cell lysate to a capture agent that specifically binds the protein kinase;
(c) removing the unbound cell lysate;
(d) exposing the bound protein kinase to a phosphor-specific antibody against a phosphorylated amino acid; and
(e) detecting binding of the phospho-specific antibody.

Embodiment 28: The method of embodiment 27, wherein the phospho-specific antibody is an anti-phosphotyrosine antibody, an anti-phosphoserine antibody, or an antiphosphotyrosine antibody.

Embodiment 29: The method of embodiment 25, wherein the phosphorylation of a protein kinase is measured by a process comprising:
(a) lysing the indicator cell to obtain cell lysate;
(b) exposing the cell lysate to a phospho-specific antibody against the phosphorylated protein kinase; and
(c) detecting binding of the phospho-specific antibody.

Embodiment 30: The method of embodiment 11, wherein the signal transduction related biological response is increase or decrease of the level of a second messenger.

Embodiment 31: The method of embodiment 30, wherein the second messenger is selected from the group consisting of diacylglycerol, phosphatidylinositol, cAMP, cGMP, IP3, $Ca^{2+}$, nitric oxide (NO), carbon monoxide (CO), hydrogen sulfide ($H_2S$), and a combination thereof.

Embodiment 32: The method of embodiment 1, wherein the indicator cell endogenously expresses the MIC-1 binding receptor, and/or the cell surface receptor kinase; furthermore, the indicator cell is derived from neuron cells.

Embodiment 33: The method of embodiment 32, wherein the neuron cell is derived from hypothalamus or brain stem.

Embodiment 34: The method of embodiment 33, wherein the neuron cell is derived from arcuate nucleus (ARC), paraventricular nucleus (PVN), area postrema (AP), or nucleus tractus solitarus (NTS).

Embodiment 35: The method of embodiment 1, wherein the MIC-1 binding receptor is a fused protein comprising the extracellular region of GFRAL, a transmembrane domain, and an intracellular region of a cell surface receptor.

Embodiment 36: The method of embodiment 35, wherein the intracellular region comprises a catalytic domain, and the biological response is the increase or decrease of the catalytic activity of the catalytic domain.

Embodiment 37: The method of embodiment 35, wherein the cell surface receptor kinase is a member receptor of TGF-β super family.

Embodiment 38: The method of embodiment 1, wherein the biological response is related to cell proliferation or cell validity.

Embodiment 39: The method of embodiment 1, wherein the biological response is related to cell apoptosis or cell growth arrest.

Embodiment 40: The method of embodiment 39, wherein the biological response is caspase activity.

Embodiment 41: The method of embodiment 39, wherein the biological response is measured as the number of viable cells or the number of apoptotic cells.

Embodiment 42: The method of embodiment 1, wherein the biological response is related to cytotoxicity.

Embodiment 43: The method of embodiment 1, wherein the biological response is up-regulated transcription of a gene.

Embodiment 44: The method of embodiment 43, wherein the gene is selected from a group consisting of GLI, MEF2, SRE, c-fos, POMC (pro-opiomelanocortin), CART (cocaine and amphetamine regulated transcript), or a combination thereof.

Embodiment 45: The method of embodiment 1, wherein the biological response is down-regulating mRNA of a gene.

Embodiment 46: The method of embodiment 45, wherein the gene is NPY (neuropeptide Y), AGRP (agouti-related protein), or a combination thereof.

Embodiment 47: A cell line for determining the activity of a MIC-1 compound, wherein the cell line expresses a MIC-1 binding receptor and a cell surface receptor kinase, wherein the MIC-1 binding receptor comprises the MIC-1 binding segment derived from GFRAL, and a biological response is induced when the MIC-1 compound, the MIC-1 binding receptor, and the cell surface receptor kinase form a ternary complex.

Embodiment 48: The cell line of embodiment 47, wherein the cell surface receptor kinase is RET receptor tyrosine kinase.

Embodiment 49: A cell line for determining the activity of a GFRAL ligand, wherein the cell lines expresses a GFRAL ligand binding receptor and RET receptor tyrosine kinase, wherein the GFRAL ligand binding receptor comprises the GFRAL ligand binding segment derived from GFRAL, and a biological response is induced when the GFRAL ligand, the GFRAL ligand binding receptor, and RET form a ternary complex.

Embodiment 50: The cell line of embodiment 47 or 49, wherein the cell line also expresses a reporter peptide, and the biological response is capable of being detected by detecting the activity of the reporter peptide.

Embodiment 51: The cell line of embodiment 50, wherein the reporter peptide is luciferase, bacterial β-galactosidase, trpE, Protein A, β-lactamase, alpha amylase, alcohol dehydrogenase, yeast alpha mating factor, etc.

Embodiment 52: The cell line of embodiment 51, wherein the reporter peptide is luciferase.

Embodiment 53: The cell line of embodiment 52, wherein the cell line also expresses SRE.

Embodiment 54: The cell line of embodiment 47 or 49, wherein the cell line is derived a mammalian cell, such as BHK21 cell, HEK293 cell, or PC-12 cell.

Embodiment 55: The cell line of embodiment 47 or 49, wherein the cell line expresses full length hGFRAL, full length hRET, and luciferate.

Embodiment 56: A method for detecting the binding affinity of a GFRAL ligand, such as a MIC-1 compound and GFRAL, comprising:

(a) contacting a test sample comprising the GFRAL ligand, such as a MIC-1 compound with a MIC-1 binding protein; and (b) detecting binding of between the GFRAL ligand, such as a MIC-1 compound and the MIC-1 binding protein, wherein the MIC-1 binding protein comprising the MIC-1 binding segment derived from GFRAL.

Embodiment 57: A method for detecting the binding affinity of a MIC-1 compound, comprising:

(a) contacting a test sample with a MIC-1 binding protein, wherein the test sample comprises a reference compound; and (b) detecting binding of the reference compound to the MIC-1 binding protein;

wherein the reference compound is a different MIC-1 compound with known binding affinity, and, the MIC-1 binding protein comprising the MIC-1 binding segment derived from GFRAL.

Embodiment 58: The method of embodiment 55, wherein the MIC-1 binding segment comprises the extracellular region of GFRAL.

Embodiment 59: The method of embodiment 55, wherein the MIC-1 binding protein comprises C1 and C2 domains of GFRAL.

Embodiment 60: The method of embodiment 55, wherein the MIC-1 binding protein is anchored on a cell surface.

Embodiment 61: The method of embodiment 55, wherein GFRAL is derived from human, mouse, rat, rabbit or cynomolgus.

Embodiment 62: The method of embodiment 53, wherein the MIC-1 binding protein is immobilized on a solid phase.

Embodiment 63: The method of embodiment 56, wherein the reference compound is immobilized.

Embodiment 64: The method of embodiment 56, wherein reference compound is labeled for detection.

Embodiment 65: The method of embodiment 63, wherein the label for detection is a radio-isotope, biotin, digoxin, tetramethylbenzidine (TMB), fluorescein, luminol, lucigenin, or luciferin.

Embodiment 66: The method of embodiment 55, wherein the binding is detected by radioactivity detection system, colour detection systems, fluorescence detection systems, or luminescence detection systems.

Embodiment 67: The method of embodiment 55, wherein binding is detected by SPA (scintillation proximity assay), TRF (time-resolved fluorescence), FRET (fluorescence resonance energy transfer), BRET (bioluminescence resonance energy transfer), TR-FRET (time-resolved fluorescence resonance energy transfer), FP (fluorescence polarization), FMAT (fluorometric microvolume assay technology), AlphaScreen™, flow cytometry, FCS (fluorescence correlation spectroscopy), SPR (surface plasmon resonance), or TIRF (total internal reflection fluorescence).

Embodiment 68: A method for determining the activity of a GFRAL ligand, comprising:

(a) contacting an indicator cell with the GFRAL ligand, and detecting a biological response of the indicator cell contacted with GFRAL ligand;

(c) contacting the indicator cell with a MIC-1 compound with known activity, and detecting a biological response of the indicator cell contacted with the MIC-1 compound;

(c) comparing the biological response induced by the GFRAL ligand with the biological response induced by the MIC-1 compound, wherein the indicator cell expresses on the cell surface a MIC-1 binding receptor comprising the MIC-1 binding segment derived from GFRAL.

Embodiment 69: A method for determining the activity of a GFRAL variant, comprising:

(a) contacting an indicator cell with a test sample that comprises the GFRAL variant and a MIC-1 compound with known activity; and (b) detecting a biological response of the indicator cell contacted with the test sample;

wherein the indicator cell expresses on the cell surface a MIC-1 binding receptor comprising the MIC-1 binding segment derived from GFRAL.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Generation of Human and Mouse GFRAL Extracellular Region Expression Constructs

Reagents: Qiagen EndoFree Plasmid Maxi Kit (#12362), Gene Synthesis and Cloning of Expression Constructs
hGFRAL ECR-pCLC Human (Homo sapiens) GDNF family receptor alpha like (hGFRAL) DNA sequence (SEQ ID: 1) is from CCDS4957.1. The sequence was analyzed with Phobius, SignalP and TMHMM. The definition of its extracellular region (ECR) is consistent with the UniProt record Q6UXV0. Only the sequence encoding the ECR (amino acids 19-351 in SEQ ID: 1) was retained while the sequences encoding the signal peptide, transmembrane, and intracellular regions were discarded. The DNA sequence encoding hGFRAL_ECR was further optimized to remove common restriction sites (EcoRI, BamHI, HindIII, and ApaI) while retaining the encoded ECR peptide sequence.

hGFRAL_ECR DNA was synthesized and cloned into expression vector pCLC. This expression vector contains a CMV promoter to drive expression in the mammalian cells. It has DNA sequence encoding CD33 signal peptide for protein secretion. It has DNA sequence encoding mouse anti-TNP light chain (ATNP LC or LC) sequence. This construct, when co-expressing in a cell with plasmid encoding a peptide comprising the anti-TNP fab heavy chain (HC) and a fragment of human PDGFRB containing the transmembrane region (HC_TM, the amino sequence is shown in SEQ ID NO: 14), would create anti-TNP Fab protein and anchored the hGFRAL_ECR on the cell surface through the PDGFRB transmembrane region. The hGFRAL_ECR DNA was cloned in frame directly after the sequence of CD33 signal peptide and in front of the ATNP LC sequence. A short linker sequence encoding GGGGSGGGGS peptide was also inserted between the hGFRAL_ECR and ATNP LC sequences to provide flexibility between the fused domains. The name of the expression plasmid is hGFRAL_ECR-pCLC. The amino acid sequence of the protein expressed by hGFRAL_ECR-pCLC is shown in SEQ ID NO: 6.

Plasmids:
hGFRAL_C1-pCLC,
hGFRAL_C2-pCLC,
hGFRAL_C3-pCLC,
hGFRAL_C1C2-pCLC, and
hGFRAL_C2C3-pCLC For the mapping of the ligand binding domain in the ECR of hGFRAL, five expression constructs were generated encoding different domains of hGFRAL. Based on homology and structural predictions, there are three separate cysteine rich domains in the hGFRAL_ECR. They are amino acid 19-130 (referred as C1 from here on), amino acid 131-219 (referred as C2 from here on), and amino acid 220-351 (referred as C3 from here on). The amino acids refer to the peptide sequence in UniProt record Q6UXV0. We generated the expression constructs encoding these domains: C1, C2, C3, C1C2, and C2C3. These constructs are in the same expression format as the full length hGFRAL_ECR-LC construct described as above. They contain the N-terminal CD33 signal peptide sequence and the C terminal ATNP LC sequence. The names of these expression plasmids are hGFRAL_C1-pCLC, hGFRAL_C2-pCLC, hGFRAL_C3-pCLC, hGFRAL_C1C2-pCLC, and hGFRAL_C2C3-pCLC. The amino acid sequences of the proteins expressed by these plasmids are shown in SEQ ID NOs: 9, 10, 11, 12, and 13 respectively.

mGFRAL_ECR-pCLC

There are two splice variants of Mouse (*Mus musculus*) GDNF family receptor alpha like (mGFRAL), the full-length cell membrane-anchored form, isoform 1 (DNA sequence is shown in SEQ ID NO: 3; amino acid sequence is shown in SEQ IN NO: 4); and a short secreted form, isoform 2, which only consisting of the signal peptide and the ECR as of isoform 1. The DNA sequence of mGFRAL isoforms 1 is from CCDS40694.1. The definition of its extracellular region (referred as mGFRAL_ECR from here on) is based on UniProt record Q63JE0-1. Only the sequence encoding the ECR was retained in the construct while the sequences predicted to encode the signal peptide, transmembrane, and intracellular regions were discarded. The DNA sequence encoding mGFRAL_ECR was further optimized to remove common restriction sites (EcoRI, BamHI, HindIII, and ApaI) while retaining the encoded ECR peptide sequence.

mGFRAL_ECR DNA was synthesized and cloned into expression vector pCLC. This expression vector contains a CMV promoter to drive expression in the mammalian cells. It has DNA sequence encoding CD33 signal peptide for protein secretion. It has DNA sequence encoding mouse anti-TNP light chain (ATNP LC or LC) sequence. This construct, when co-expressing with plasmid encoding a peptide comprising the anti-TNP fab heavy chain (HC) and a fragment of human PDGFRB containing the transmembrane region (HC_TM, the amino sequence is shown in SEQ ID NO: 14), would create anti-TNP Fab protein and anchored the mGFRAL_ECR on the cell surface through the PDGFRB transmembrane region. The mGFRAL_ECR DNA was cloned in frame directly after the CD33 signal sequence and in front of the ATNP LC sequence. A short linker sequence encoding GGGGSGGGGS peptide was also inserted between the mGFRAL_ECR and ATNP LC sequences to provide flexibility between the fused domains.

The name of the expression plasmid is mGFRAL_ECR-pCLC. The amino acids sequence of the protein expressed by mGFRAL_ECR-pCLC is shown in SEQ ID NO: 8.

pJSV002-ATNP-mIgG1-HL-HPC4

The coding sequence of the heavy chain of an ATNP Fab fused with HPC4 at its C terminus was synthesized and cloned into expression vector pJSV002 (HC_HPC4, the amino sequence is shown in SEQ ID NO: 15). This expression vector contains a CMV promoter to drive expression in the mammalian cells. It has DNA sequence encoding CD33 signal peptide for protein secretion. When the construct is co-transfected into mammalian cells with plasmid encoding the ATNP LC or a fusion protein comprising ATNP LC, the ATNP Fab or a fusion protein comprising ATNP Fab will be formed, e.g., hGFRAL(ECR)-Fab, mGFRAL(ECR)-Fab.

pJSV002-CD33-hGFRAL ECR-hIgG1.1 Fc hGFRAL_ECR DNA was synthesized and cloned into expression vector pJSV002-CD33-hIgG1.1_Fc. This vector has the same CMV promoter to drive expression. The hGFRAL_ECR was cloned in frame between the CD33 signal peptide and the hIgG1.1_Fc sequence. The amino acid sequence of the fusion protein is hGFRAL_ECR-hIgG1.1_Fc (SEQ ID NO: 7, also "hGFRAL-Fc"). The name of the expression plasmid is pJSV002-CD33-hGFRAL_ECR-hIgG1.1_Fc.

Example 2

Expression of Soluble Form of Human and Mouse GFRAL Extracellular Region Fusion Proteins, hGFRAL(ECR)-Fab, hGFRAL(ECR)-Fc, and mGFRAL(ECR)-Fab Cell: HEK293-6E
Reagents:
Gibco® FreeStyle™ 293 Expression Medium, Invitrogen, Cat. No.: 12338-026;
Gibco® 10% Pluronic F68, Invitrogen, Cat. No.: 24040-032;
Gibco® Geneticin, Invitrogen, Cat. No.: 11811-023;
Gibco® Opti-MEM® I+GlutaMax™-I, Invitrogen, Cat. No.: 51985-034;
293Fectin™ Reagent, Invitrogen, Cat. No.: 12347-019;
Plasmids:
hGFRAL_ECR-pCLC
pJSV002-CD33-hGFRAL_ECR-hIgG1.1_Fc
mGFRAL_ECR-pCLC
hGFRAL_C1-pCLC
hGFRAL_C2-pCLC
hGFRAL_C3-pCLC
hGFRAL_C1C2-pCLC
hGFRAL_C2C3-pCLC
pJSV002-ATNP-mIgG1-HP-HPC4 (for TM1, type I cell surface receptor)
Transient Transfection
hGFRAL(ECR)-Fab-HPC4 (hGFRAL(ECR)-Fab), hGFRAL-hIgG1.1_Fc (hGFRAL(ECR)-Fc) and mGFRAL(ECR)-Fab-HPC4 (mGFRAL(ECR)-Fab) were produced using transient transfection in HEK293-6E cells.

HEK293-6E cells were grown in suspension in Gibco® FreeStyle™ 293 Expression Medium supplemented with 0.1% Fluronic F68 at 37° C. with 5% $CO_2$. Cells were transfected when reaching $1\times10^6$ cells/ml density.

For 300 ml cell volume, 300 µg of DNA were used for transfection. For the two pCLC constructs, 300 µg of DNA included 240 µg of the plasmids and 60 µg pJSV002-ATNP-mIgG1-HP-HPC4.

The 300 µg of DNA for transfection was diluted in 15 ml of Opti-MEM. 300 µl of 293Fectin was added to a separate 15 ml of Opti-MEM and was gently mixed. The transfection agent was incubated for 5 minutes at room temperature. After incubation, the 15 ml diluted DNA for transfection was added to the 293Fectin mixture for a total volume of 30 ml. This mixture was then incubated for 25 minutes at room temperature to allow 293Fectin-DNA complexes to form.

After incubation, the mixture containing 293Fectin-DNA complexes was added to 300 ml of HEK293-6E cells (at $1\times106$ cells/ml density) in 1 L flask. The cells were then incubated in 37° C. shaking incubator with 5% $CO_2$.

The cells were harvested 5 days post transfection. Cells were removed by centrifugation at 6000 rpm for 15 minutes followed by filtration of the supernatant using a 0.45 µm filter. The supernatant were checked for expression using SDS-PAGE gel and delivered for subsequent purification.

Example 3

Cloning and Expression of Soluble Forms of Human RET Extracellular Region, hRET(ECR)-Fc and hRET(ECR)-Fab Reagents
Qiagen EndoFree Plasmid Maxi Kit (#12362)
Gibco® FreeStyle™ 293 Expression Medium, Invitrogen, Cat. No.: 12338-026;
Gibco® 10% Pluronic F68, Invitrogen, Cat. No.: 24040-032;
Gibco® Geneticin, Invitrogen, Cat. No.: 11811-023;
Gibco® Opti-MEM® I+GlutaMax™-I, Invitrogen, Cat. No.: 51985-034;
293Fectin™ Reagent, Invitrogen, Cat. No.: 12347-019;
Cell: HEK293-6E
Gene Synthesis and Cloning of Expression Constructs Human (Homo sapiens) proto-oncogene tyrosine-protein kinase receptor's (RET) DNA sequence is from CCDS7200.1 and UniProt P07949-1 (hRET51, amino acid sequence is shown in SEQ ID NO: 5). The sequence was analyzed with Phobius, SignalP and TMHMM. The definition of its extracellular region (ECR) is consistent with the UniPort record P07949-1. Only the sequence encoding the ECR (amino acids 29-636) was retained while the sequences encoding the signal peptide, transmembrane, and intracellular regions were discarded. The DNA sequence encoding hRET_ECR was further optimized to remove common restriction sites (EcoRI, BamHI, HindIII, and ApaI) while retaining the encoded ECR peptide sequence. There is an additional splice variant of hRET with corresponding CCDS (CCDS53525.1) and UniPort P07949-2. The differences between the two splice forms are in the C terminal, which are within intracellular regions. The hRET_ECR sequences of the two splice forms are the same.

hRET_ECR DNA was synthesized and cloned into two expression vectors. The first vector was pCLC. This expression vector contains a CMV promoter to drive expression in the mammalian cell lines. It has DNA sequence encoding CD33 signal peptide for protein secretion. It has DNA sequence encoding mouse anti-TNP light chain (ATNP LC, or LC) sequence. This construct, when co-expressing with plasmid encoding the anti-TNP fab heavy chain, would create anti-TNP Fab protein. The hRET_ECR DNA was cloned in frame directly after the CD33 signal sequence and in front of the ATNP LC sequence. A short linker sequence encoding GGGGSGGGGS peptide was also inserted between the hRET_ECR and ATNP LC sequences to provide flexibility between the fused ECR and ATNP LC domains. The resulting fusion protein is hRET_ECR-LC. The name of the expression plasmid is hRET_ECR-pCLC. The second vector is pJSV002-CD33-hIgG1.1_Fc. It has the same CMV promoter to drive expression. The hRET_ECR was cloned in frame between the CD33 signal peptide and the hIgG1.1_Fc sequence. The sequence of the fusion protein is hRET_ECR-hIgG1.1_Fc. The name of the expression plasmid is pJSV002-CD33-hRET_ECR-hIgG1.1_Fc.

Plasmids for Transfection
  hRET_ECR-pCLC
  pJSV002-CD33-hRET_ECR-hIgG1.1_Fc
  pJSV002-aTNP-mIgG1-HL-HPC4 (for TM1)

All expression plasmids were sequence verified and prepared in large quantity using Qiagen EndoFree Plasmid Maxi Kit following manufacturer's instruction.

Transient Transfection

2 Proteins were produced using transient transfection in HEK293-6E cells. They are hRET(ECR)-Fab-HPC4 (hRET (ECR)-Fab), AND hRET(ECR)-hIgG1.1_Fc (hRET(ECR)-Fc).

HEK293-6E were grown in suspension in Gibco® FreeStyle™ 293 Expression Medium supplemented with 0.1% Fluronic F68 at 37° C. with 5% $CO_2$. Cells were transfected when reaching $1 \times 10^6$ cells/ml density.

For 300 ml cell volume, 300 μg of DNA were used for transfection. For the two pCLC constructs, the 300 μg of DNA included 240 μg of the plasmids and 60 μg pJSV002-aTNP-mIgG1-HL-HPC4 plasmid. For the two hIgG1.1_Fc constructs, 300 μg of plasmids DNA were used.

DNA was diluted in 15 ml of Opti-MEM. 300 μl of 293Fectin added to a separate 15 ml of Opti-MEM and was gently mixed. The transfection agent was incubated for 5 minutes at room temperature. After incubation, the 15 ml diluted DNA was added to the 293Fectin mixture for a total volume of 30 ml. This mixture was then incubated for 25 minutes at room temperature to allow 293Fectin-DNA complexes to form.

After incubation, the mixture containing 293Fectin-DNA complexes was added to 300 ml of HEK293-6E cells (at $1 \times 10^6$ cells/ml density) in 1 L flask. The cells were then incubated in 37° C. shaking incubator with 5% $CO_2$.

The cells were harvested at 5 days post transfection. Cells were removed by centrifugation at 6000 rpm for 15 minutes followed by filtration of the supernatant using a 0.45 μm filter. The supernatant were checked for expression using SDS-PAGE gel and delivered for subsequent purification.

Example 4

Purification of Human and Mouse GFRAL Extracellular Regions Fusion Proteins

Purification of hGFRAL(ECR)-Fab-HPC4

The culture supernatant containing secreted hGFRAL (ECR)-Fab-HPC4 was applied to an anti-HPC4 sepharose 4FF affinity column (anti-HPC4 antibody coupled to the CNBr activated sepharose 4FF resin, 15 mL), equilibrated in 20 mM Tris-HCl, 100 mM NaCl, 1 mM CaCl2, pH 7.4. The bound hGFRAL(ECR)-Fab-HPC4 protein was eluted with 20 mM Tris-HCl, 100 mM NaCl, pH 7.4, 1 mM EGTA. Fractions were pooled and concentrated to a final volume of approx. 3.0 mL using Millipore Amicon Ultra Centrifugal Filters (UFC 901096 10K NMWL, Billerica, Mass., USA) and further purified by size-exclusion chromatography on a Hi-Load 16/60 Superdex 200 μg column (28-9893-35 GE Healthcare, Uppsala, Sweden) in phosphate buffered saline (PBS). The fractions containing monomeric hGFRAL (ECR)-Fab-HPC4 were pooled and diluted 10 fold into 20 mM sodium acetate pH5.0 and then applied to a Mono S 5/52 GL column (17-5168-01 GE Healthcare, Uppsala, Sweden). The bound hGFRAL(ECR)-Fab-HPC4 was then eluted with a 10%-50% linear gradient of 20 mM sodium acetate pH5.0, 1 M NaCl in 30 column volumes. The fractions of hGFRAL(ECR)-Fab-HPC4 were buffer-exchanged to PBS by Millipore Amicon Ultra Centrifugal Filters (UFC 901096 10K NMWL, Billerica, Mass., USA). Purified proteins were sterilized by filtration through a 0.2 m filter unit (16541 Sartorius, Goettingen, Germany). The final protein concentrations were determined by measuring 280 nm absorbance with a NANODROP UV spectrometer.

Purification of mGFRAL(ECR)-Fab-HPC4

The culture supernatant containing secreted mGFRAL (ECR)-Fab-HPC4 was applied to an anti-HPC4 sepharose 4FF affinity column (anti-HPC4 antibody coupled to the CNBr activated sepharose 4FF resin, 5 mL), equilibrated in 20 mM Tris-HCl, 100 mM NaCl, 1 mM CaCl2, pH 7.4. The bound mGFRAL(ECR)-Fab-HPC4 protein was eluted with 20 mM Tris-HCl, 100 mM NaCl, pH 7.4, 1 mM EGTA. Fractions were pooled and concentrated to a final volume of approx. 3.0 mL using Millipore Amicon Ultra Centrifugal Filters (UFC 901096 10K NMWL, Billerica, Mass., USA) and further purified by size-exclusion chromatography on a Hi-Load 16/60 Superdex 200 pg column (28-9893-35 GE Healthcare, Uppsala, Sweden) in phosphate buffered saline (PBS). The fractions containing monomeric mGFRAL-Fab-HPC4 were pooled and concentrated by Millipore Amicon Ultra Centrifugal Filters (UFC 901096 10K NMWL, Billerica, Mass., USA). Purified protein was sterilized by filtration through a 0.2 mm filter unit (16541 Sartorius, Goettingen, Germany). The final protein concentration was determined by measuring 280 nm absorbance with a NANODROP UV spectrometer.

Purification of Human GFRAL Fragments Fusion Proteins

Five GFRAL fragments containing different domains were purified i.e. hGFRAL_C1_Fab_HPC4, hGFRAL_C2_Fab_HPC4, hGFRAL_C3_Fab_HPC4, hGFRAL_C1C2_Fab_HPC4 and hGFRAL_C2C3_Fab_HPC4.

For each GFRAL fragment fusion protein, culture supernatant containing secreted protein was applied to an anti-HPC4 sepharose 4FF affinity column (anti-HPC4 antibody coupled to the CNBr activated sepharose 4FF resin, 5 mL), equilibrated in 20 mM Tris-HCl, 100 mM NaCl, 1 mM CaCl2, pH 7.4. The bound protein was eluted with 20 mM Tris-HCl, 100 mM NaCl, pH 7.4, 1 mM EGTA. Fractions were pooled and concentrated to a final volume of approx. 3.0 mL using Millipore Amicon Ultra Centrifugal Filters (UFC 901096 10K NMWL, Billerica, Mass., USA) and further purified by size exclusion chromatography on a HiLoad 16/60 Superdex 200 pg column (28-9893-35 GE Healthcare, Uppsala, Sweden) in phosphate buffered saline (PBS). The fractions containing monomeric GFRAL fragment fusion protein were pooled and concentrated by Millipore Amicon Ultra Centrifugal Filters (UFC 901096 10K NMWL, Billerica, Mass., USA).

For hGFRAL_C3_Fab_HPC4, the protein was further polished by cation exchange chromatography. The fractions from size exclusion chromatography were pooled and diluted 10 fold into 20 mM NaAc pH5.0 and then applied to a Mono S 5/52 GL column (17-5168-01 GE Healthcare, Uppsala, Sweden). The bound protein was eluted with a 100-500 mM linear gradient of NaCl in 30 column volumes followed by a 600 mM NaCl step elution in 5 column volumes in 20 mM NaAc pH5.0. The charge variants of hGFRAL_C3_Fab_HPC4 were pooled separately and buffer-exchanged to PBS by Millipore Amicon Ultra Centrifugal Filters (UFC 901096 10K NMWL, Billerica, Mass., USA).

Purified protein was sterilized by filtration through a 0.2 mm filter unit (16541 Sartorius, Goettingen, Germany). The final protein concentration was determined by measuring 280 nm absorbance with a NANODROP UV spectrometer. Purified protein was analyzed by sodium dodecyl sulfate polyacrylamide gel electrophoresis (SDS-PAGE) and submitted to QC tests including endotoxin test and SEC-MALS. Protein identity was confirmed by LC-MS.

Example 5

Purification of Human RET Extracellular Region Fusion Proteins

Purification of hRET(ECR)-Fab-HPC4

The culture supernatant containing secreted hRET(ECR)-Fab-HPC4 was applied to an anti-HPC4 sepharose 4FF affinity column (anti-HPC4 antibody coupled to the CNBr activated sepharose 4FF resin, 5 mL), equilibrated in 20 mM Tris-HCl, 100 mM NaCl, 1 mM CaCl2, pH 7.4. The bound hRET(ECR)-Fab-HPC4 protein was eluted with 20 mM Tris-HCl, 100 mM NaCl, pH 7.4, 1 mM EGTA. Fractions were pooled and concentrated to a final volume of approx. 3.0 mL using Millipore Amicon Ultra Centrifugal Filters (UFC 901096 10K NMWL, Billerica, Mass., USA) and further purified by size exclusion chromatography on a Hi-Load 16/60 Superdex 200 pg column (28-9893-35 GE Healthcare, Uppsala, Sweden) in phosphate buffered saline (PBS). The fractions containing monomeric hRET(ECR)-Fab-HPC4 were pooled and concentrated by Millipore Amicon Ultra Centrifugal Filters (UFC 901096 10K NMWL, Billerica, Mass., USA). Purified protein was sterilized by filtration through a 0.2 mm filter unit (16541 Sartorius, Goettingen, Germany). The final protein concentration was determined by measuring 280 nm absorbance with a NANODROP UV spectrometer. Purified protein was analyzed by sodium dodecyl sulfate polyacrylamide gel electrophoresis (SDS-PAGE) and submitted to QC tests including endotoxin test and SEC-MALS. Protein identity was confirmed by LC-MS.

Example 6

Throughput Plasmid Preparation for Cell Surface Display of Target Proteins

In order to get high-quality plasmids for cell surface display of target proteins on HEK293-6E cells by transient transfection, a high throughput method was designed and optimized to ensure that the extracted plasmids are free from contamination, and the endotoxin level in extracted plasmids is low enough for transfection of mammalian cells. The Nucleo-Bond® 96 Xtra EF kit (MACHEREY-NAGEL, Cat #: 740430.4) was used in plasmid extraction process with optimized protocol as described as follows.

At first, the stock plasmids were transformed into an *E. coli* strain, DH5α. Single colonies of each transformation were picked to inoculate a 1.0 mL start culture (LB medium) in 2.0 mL deep-well plates (Costar, Cat #: 3960). 100 ng/mL carbenicillin was used in the culture medium to give strong antibiotic selection pressure for retaining plasmids inside *E. coli* cells. The culture plates were incubated in a shaking incubator at 37° C., 800 rpm overnight. In order to have robust growth of the culture and enough culture volume for plasmid extraction, a two-step culture strategy was developed. The start culture after overnight growth was subcultured into 4 copies of 1.5 mL culture (TB medium, 100 ng/mL carbenicillin) in 2.0 mL deep-well plates which were incubated again in a shaking incubator at 37° C., 800 rpm overnight. So for each plasmid, 4×1.5=6 mL culture was prepared for extraction. Cells in each 1.5 mL culture plate were lysed independently, and 4 copies of cleared lysate were loaded to a single well of a plasmid DNA binding plate. The plasmid DNA binding plate was washed to remove impurities and endotoxin, and subsequently plasmids were eluted to a collection plate (Eppendorf, Cat #: 0030 502.140) using an endotoxin-free buffer. All liquid handling steps were automated using a liquid handling robot. The entire extraction process was optimized and tested so that there was no cross-well contamination, and the extracted plasmids were free of microbial contamination.

Example 7

Transient Transfection of HEK293-6E Cells to Display the Target Proteins on the Cell Surface Cells: HEK293-6E
Reagents:
  Gibco® FreeStyle™ 293 Expression Medium, Invitrogen, Cat. No.: 12338-026;
  Gibco® 10% Pluronic F68, Invitrogen, Cat. No.: 24040-032;
  Gibco® Geneticin, Invitrogen, Cat. No.: 11811-023;
  Gibco® Opti-MEM® I+GlutaMax™-I, Invitrogen, Cat. No.: 51985-034;
  293Fectin™ Reagent, Invitrogen, Cat. No.: 12347-019;
Equipment:
  Infors HT Multitron
  Tissue culture plate, 24 well, flat bottom with low evaporation lid (Falcon®, Cat. No.: 353047)
Plasmids:
  ECR-LC (ECR-ATNP mIgG1 Fab LC) for TM1 like GFRAL
  HC-TM (ATNP mIgG1 Fab HC-PDGFR TM) for TM1
  LC-ECR (ATNP mIgG1 Fab LC-ECR) for TM2
  TM-HC (OX40L TM-ATNP mIgG1-HC Fab) for TM2
Transient Expression:

This process is to transfect the HEK293-6E cells with corresponding plasmid DNA to display the ECR (extracellular region) of target protein on the surface of the cells as a fusion protein with the Fab of mouse anti-trinitrophenyl (ATNP) mAb. To achieve this, the plasmid encoding a protein fusion between the ECR and light chain of the Fab (ECR-LC or LC-ECR) was co-transfected into HEK293-6E cells with a plasmid encoding a protein fusion between the heavy chain of the Fab and a transmembrane domain (HC-TM or TM-HC). When expressed, the ECR and Fab light chain fusion protein formed a complex with the Fab heavy chain, which is anchored on the cell surface through the transmembrane domain.

The Fab light chain was located either at the N-terminus or at the C-terminus of the ECR of the target protein, depending on the transmembrane type of the target protein. If it is type 1 transmembrane protein (TM1), e.g. GFRAL, the Fab light chain is located at the C-terminus (ECR-LC) and the plasmid for co-transfection carries a fusion gene of Fab heavy chain and PDGFR transmembrane domain, namely HC-TM (ATNP mIgG1-Fab-PDGFR TM). If it is type 2 transmembrane protein (TM2), the Fab light chain is located at the N-terminus (LC-ECR) and the plasmid for co-transfection carries a fusion gene of OX40L transmembrane domain and Fab heavy chain, namely TM-HC (OX40L TM-ATNP mIgG1-HC Fab). The expression of ATNP mIgG1-Fab-PDGFR TM and OX40L TM-ATNP mIgG1-HC Fab was droved by CMV promoter in the vector. Type 1 transmembrane proteins are single-pass transmembrane proteins which have their N-terminus exposed to the extracellular space, while type 2 transmembrane proteins have their C-terminus exposed to the extracellular space.

Suspension HEK293-6E cells were grown with 5% $CO_2$ and shaking at 37° C. in Gibco® FreeStyle™ 293 Expression Medium supplemented with 0.1% Fluronic F68 and 25 μg/ml of Geneticin. The cells were passaged between 0.3 and $2.5 \times 10^6$ cells/ml.

On the day of transfection, 1 ml of the cells with the density of $1.1 \times 10^6$ cells/ml and the viability of higher than 90% were prepared with fresh, pre-warmed cell culture medium (Gibco® FreeStyle™ 293 Expression Medium supplemented with 0.1% Fluronic F68 and 25 μg/ml of Geneticin) and allocated to 24 well culture plate.

1 μg of plasmid DNA, including 0.8 μg ECR-LC or LC-ECR DNA and 0.2 μg HC-TM or TM-LC DNA, was diluted in Opti-MEM® I with GlutaMax™-I to a total volume of 33.3 ul. Meanwhile, 1 μl of 293Fectin™ Reagent was diluted in Opti-MEM® I with GlutaMax™-I to a total volume of 33.3 ul. The 293Fectin mixture was incubated for 5 minutes at room temperature. After the 5-minute incubation, the diluted 293Fectin™ Reagent was added to the diluted DNA, and further incubated for 20 minutes at room temperature to allow the 293fectin™-DNA complexes to form.

After the 293fectin™ and DNA incubation is complete, the 293fectin™-DNA mixture was added to the 1 ml HEK293-6E cells. The cells were incubated at 37° C. on an orbital shaker rotating at 250 rpm (orbit 25 mm) with 5% $CO_2$. The cells were harvested at 40 hours after transfection and analyzed by FACS. The results are presented in both tables and figures, including curves and FACS dot-plot drawings.

Example 8 mAb26 Preparation and the In Vivo Activities Thereof mAb26 is a monoclonal blocking antibody of wtMIC-1. The preparation and characterization of mAb26 can be found in Fairlie W D et al., Epitope mapping of the transforming growth factor-beta superfamily protein, macrophage inhibitory cytokine-1 (MIC-1): identification of at least five distinct epitope specificities, Biochemistry. 2001 Jan. 9; 40(1):65-73.

We confirmed that mAb26 can inhibit wtMIC-1's in vivo activity by reversing its food intake suppressing.

In the in vivo study, rats were pre-treated IP with 7 mg mAb26/animal and an isotype antibody as control (Ctrl. Ab). Without treatment of mAb26, wtMIC-1 reduced 24 hr food intake by about 40% in animals. In contrast, this food intake suppressing activity was almost abolished by mAb26. This study suggests that mAb26 blocks MIC-1's binding to MIC-1's functional receptor. Please see FIG. 1.

Example 9

Anti-MIC-1 Antibody Blocks Binding of MIC-1 to Soluble Human and Mouse GFRAL(ECR)-Fab-HPC4

Figure 2:
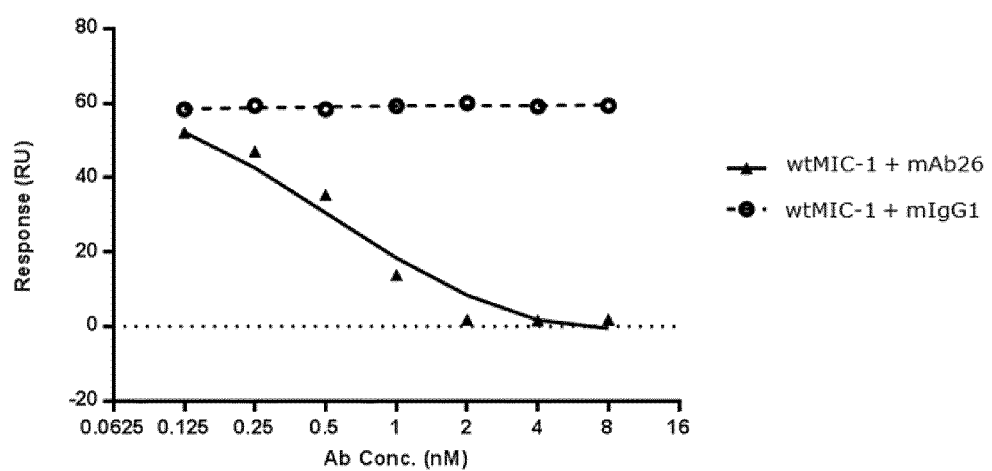
FIG. 2 shows that mAb26 blocked binding of wtMIC-1 to immobilized hGFRAL(ECR)-Fab in SPR in a dose-dependent manner.

A Biacore® 4000 (GE Healthcare, Piscataway, N.J., USA) instrument was used for SPR-based blocking assay to analyze the binding specificity between wild type human MIC-1 (wtMIC-1) and GFRAL. The assays were performed at 25° C. at flow rates of 30 μL/minute in 1×HBS-P running buffer (BR-1006-71, GE Healthcare, Piscataway, N.J., USA). wtMIC-1 was mixed with various concentration of MIC-1 blocking antibody mAb26 to form complex of wtMIC-1 and mAb26. The mixture was injected as analyte. hGFRAL(ECR) was immobilized on the surface of the chip as ligand. wtMIC-1 binding to immobilized hGFRAL(ECR) was detected. With the decreased binding level (response unit, RU), mAb26 dose-dependently blocked wtMIC-1's binding to immobilized hGFRAL(ECR) whereas isotype control (mIgG1) did not (FIG. 2, Table 1). This further suggested the binding of MIC-1 to hGFRAL was specific.

TABLE 1

Binding of wtMIC-1 to hGFRAL(ECR) was blocked by mAb26 in SPR

| Ab Conc. (nM) | Response (RU) | |
| --- | --- | --- |
|  | wtMIC-1 + mAb26 | wtMIC-1 + mIgG1 (ctrl.) |
| 0 | 57.1 | 58.3 |
| 0.125 | 52.1 | 58.4 |
| 0.25 | 47 | 59.4 |
| 0.5 | 35.4 | 58.4 |
| 1 | 13.8 | 59.3 |
| 2 | 1.8 | 60 |
| 4 | 1.6 | 59.1 |
| 8 | 1.9 | 59.4 |

Figure 3:
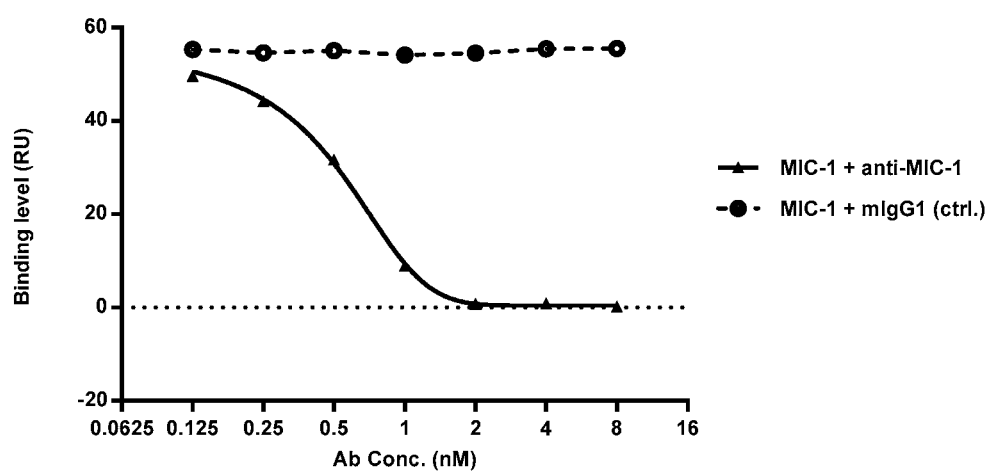
FIG. 3 shows that mAb26 blocked binding of wtMIC-1 to immobilized mGFRAL(ECR)-Fab in SPR in a dose-dependent manner.

Similarly, the binding of MIC-1 to mouse GFRAL was characterized with Biacore® 4000. wtMIC-1 was mixed with various concentration of mAb26 to form complex and injected as analyte; while mGFRAL(ECR) was immobilized as ligand. wtMIC-1 binding to immobilized mGFRAL (ECR) was detected. With the decreased binding level (response unit, RU), mAb26 dose-dependently blocked wtMIC-1 binding to immobilized mGFRAL(ECR) whereas isotype control did not. This further suggested the binding between MIC-1 and GFRAL is specific (FIG. 3, Table 2).

TABLE 2

Binding of wtMIC-1 to mGFRAL(ECR) was blocked by mAb26 in SPR

| Ab Conc. (nM) | Response (RU) | |
| --- | --- | --- |
|  | wtMIC-1 + mAb26 | wtMIC-1 + mIgG1 (ctrl.) |
| 0 | 56.2 | 55.6 |
| 0.125 | 49.6 | 55.3 |
| 0.25 | 44.2 | 54.6 |
| 0.5 | 31.7 | 55 |
| 1 | 8.9 | 54.1 |

TABLE 2-continued

Binding of wtMIC-1 to mGFRAL(ECR) was blocked by mAb26 in SPR

| Ab Conc. (nM) | Response (RU) | |
|---|---|---|
| | wtMIC-1 + mAb26 | wtMIC-1 + mIgG1 (ctrl.) |
| 2 | 0.8 | 54.5 |
| 4 | 0.9 | 55.4 |
| 8 | 0.2 | 55.5 |

Example 10

Ret Binds to Complex of MIC-1 and GFRAL hRet and complex of hGFRAL and MIC-1 interactions were assessed by SPR-based binding assay. A Biacore® 4000 (GE Healthcare, Piscataway, N.J., USA) instrument was used. The assays were performed at 25° C. at flow rates of 30 μL/minute in 1×HBS-P running buffer (BR-1006-71, GE Healthcare, Piscataway, N.J., USA). hRet(ECR)-Fc was immobilized through Fc as ligand on the chip. VISTA-Fc was immobilized as negative control ligand. The complex of MIC-1 and hGFRAL was prepared by pre-incubating wtMIC-1 with hGFRAL(ECR)-His. wtMIC-1, hGFRAL (ECR)-His, complex of wtMIC-1 and Ctrl-His, and complex of wtMIC-1 and hGFRAL(ECR)-His at various concentration were run as flow-through analyte.

Figure 4:
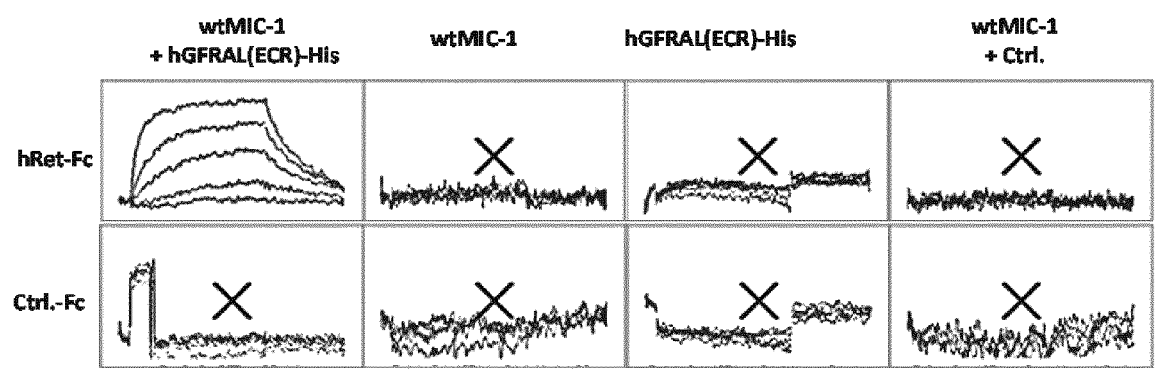
FIG. 4 shows that RET receptor tyrosine kinase is the co-binder of MIC-1 and GFRAL. In the presence of wtMIC-1, Ret-Fc specifically bound to hGFRAL(ECR) but not to GFRA1(ECR). Ret-Fc did not bind to wtMIC-1, nor to hGFRAL(ECR) in the absence of wtMIC-1.

Results showed that hRet only bound to complex of wtMIC-1 and hGFRAL(ECR)-His, but not to any other analytes (FIG. 4 and Table 3). VISTA did not bind to any of the analytes. Thus, it can be concluded that that hRet binds to hGFRAL in the presence of MIC-1; and Ret, MIC-1 and GFRAL forms a ternary complex.

TABLE 3

Ret bound to complex of MIC-1 and GFRAL

| Analyte | Analyte Conc (nM) | Response (RU) | |
|---|---|---|---|
| | | hRet-Fc | Ctrl-Fc |
| hGFRAL(ECR)-His | 0 | 0 | 0 |
| | 12 | −0.03970337 | −2.343414 |
| | 37 | −0.1051636 | −2.039063 |
| | 111 | 0.208313 | −2.940094 |
| | 333 | −0.4967651 | −3.480164 |
| | 1000 | −1.109711 | −3.848938 |
| wtMIC-1 | 0 | 0 | 0 |
| | 12 | 0.1835941 | −0.244781 |
| | 37 | 0.4674381 | −0.017883 |
| | 111 | 0.4840397 | 0.361664 |
| | 333 | 0.8801884 | 0.225617 |
| | 1000 | 0.5267033 | −0.514648 |
| wtMIC-1 + Ctrl-His | 0 | 0 | 0 |
| | 12 | −0.179032 | −0.1569062 |
| | 37 | −0.10286 | −0.5586091 |
| | 111 | 0.291336 | −0.3733826 |
| | 333 | 0.544601 | −1.0348359 |
| | 1000 | 0.324859 | 0.0764923 |
| wtMIC-1 + hGFRAL(ECR)-His | 0 | 0 | 0 |
| | 12 | 0.2256165 | −1.3935545 |
| | 37 | 1.9661557 | −1.4817815 |
| | 111 | 5.4817807 | −1.018219 |
| | 333 | 8.3245547 | −1.4296875 |
| | 1000 | 10.7024807 | −1.4036565 |

Example 11

Figure 5:
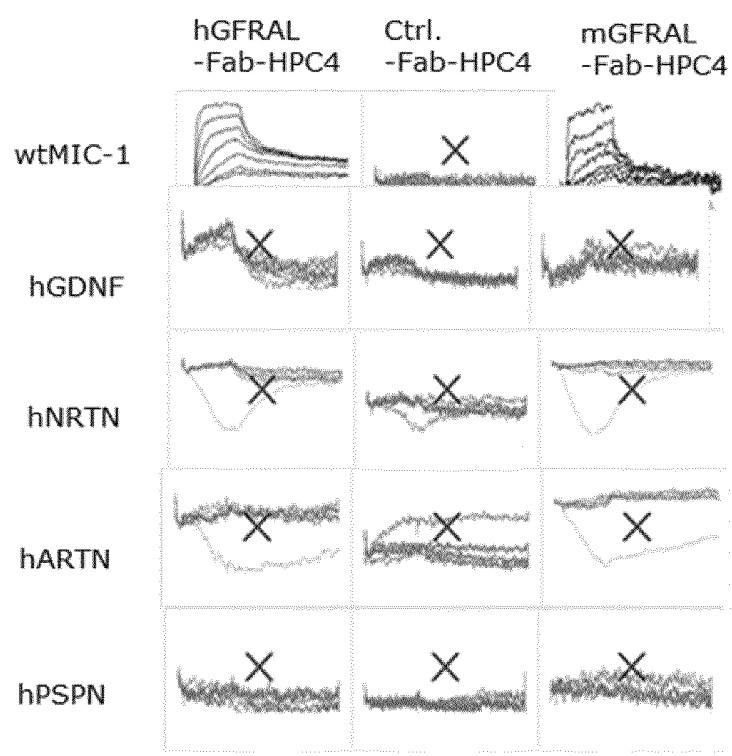
FIG. 5 shows that wtMIC-1 specifically bound to GFRAL, but not to the four receptors of GDNF family (GDNF, NRTN, ARTN and PSPN) in SPR.

Survey of Binding Interactions Between GDNF Family (MIC-1, GDNF, NRTN, ARTN and PSPN) and GFRAL For SPR-based binding assay, wtMIC-1 as well as hGDNF, hNRTN, hARTN and hPSPN, at various concentrations were run as flow-through analytes. hGFRAL(ECR)-Fab and mGFRAL(ECR)-Fab were immobilized as ligand. Results show that only wtMIC-1 bound to hGFRAL(ECR)-Fab and mGFRAL(ECR)-Fab. FCRL2-Fab-HPC4 (Ctrl.-Fab-HPC4) was used as control. Please see FIG. 5 and Table 4. Results showed that hGFRAL or mGFRAL only bound to wtMIC-1, but not to the other four ligands of GDNF family.

TABLE 4 hGDNF, hNRTN, hARTN or hPSPN did not bind to wtMIC-1 in SPR

| | hGFRAL(ECR)-Fab-HPC4 | Ctrl.-Fab-HPC4 | mGFRA(ECR)L-Fab-HPC4 |
|---|---|---|---|
| wtMIC-1 | ✓ | x | ✓ |
| hGDNF | x | x | x |
| hNRTN | x | x | x |
| hARTN | x | x | x |
| hPSPN | x | x | x |

"✓": binding was detected;
"x": No binding was detected

Example 12

Characterization of GFRAL Domain(s) for MIC-1 Interaction

The ECR of hGFRAL has three cysteine-rich domains: C1, C2 and C3, according to sequence comparison to GDNF family receptor α (GFRα) and secondary structure analysis. To identify which domain is responsible of binding to MIC-1, soluble GFRAL fragments (hGFRAL(ECR)-Fab-HPC4, hGFRAL_C1_Fab_HPC4, hGFRAL_C2_Fab_HPC4, hGFRAL_C3_Fab_HPC4, hGFRAL_C1C2_Fab_HPC4, and hGFRAL_C2C3_Fab_HPC4) were prepared according to previous examples.

Figure 6:
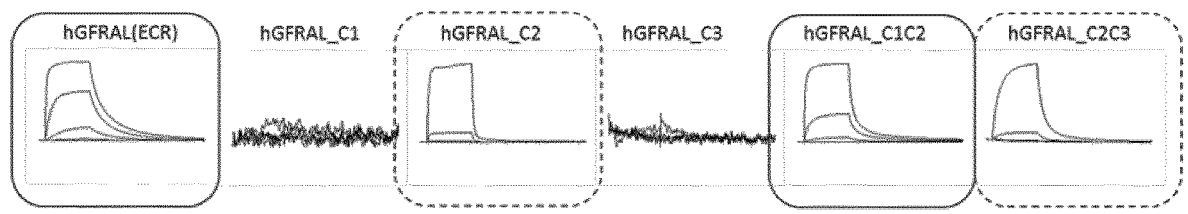
FIG. 6 shows that GFRAL domain(s) for MIC-1 binding interaction is located within C1C2 domains of the extracellular region of hGFRAL. wtMIC-1 strongly bound to hGFRAL_C1C2 at 1 nM in SPR; wtMIC-1 weakly bound to hGFRAL_C2 or hGFRAL_C2C3 at 1000 nM in SPR.

MIC-1 interactions with soluble GFRAL fragments were assessed by SPR-based binding assay. A Biacore® 4000 (GE Healthcare, Piscataway, N.J., USA) instrument was used for SPR-based binding assay. The assays were performed at 25° C. at flow rates of 30 μL/minute in 1×HBS-P running buffer (BR-1006-71, GE Healthcare, Piscataway, N.J., USA). Purified GFRAL fragments at various concentrations were run as flow-through analyte and wtMIC-1 was immobilized as ligand. Please see FIG. 6 and Table 5.

TABLE 5

Relative binding of wtMIC-1 to GFRAL fragments

| Ligand | % of Binding |
|---|---|
| hGFRAL(ECR)-Fab-HPC4 | 100 |
| hGFRAL_C1_Fab_HPC4 | N.A. |
| hGFRAL_C2_Fab_HPC4 | 21 |

TABLE 5-continued

Relative binding of wtMIC-1 to GFRAL fragments

| Ligand | % of Binding |
|---|---|
| hGFRAL_C3_Fab_HPC4 | N.A. |
| hGFRAL_C1C2_Fab_HPC4 | 87 |
| hGFRAL_C2C3_Fab_HPC4 | 8 |

*Binding between wtMIC-1 and hGFRAL(ECR) was detected as the strongest, thus was set up as 100%
"N.A.": not available According to the results shown above, hGFRAL_C1C2 showed strong binding to wtMIC-1. In addition, hGFRAL_C2 and hGFRAL_C2C3 at 1000 nM showed weak but apparent binding to immobilized wtMIC-1 in SPR, which indicates that C2 involves in direct binding with MIC-1 and should be the crucial fragment.

Example 13

Characterization of GFRAL Domain(s) for Ret to Bind with MIC-1/GFRAL Complex

To identify which domain of GFRAL (C1, C2 and C3) is responsible of MIC-1/GFRAL/Ret ternary complex formation, flow cytometry-based binding assay was performed. Binding of Ret-Fc protein against HEK cells expressing hGFRAL(ECR) and its fragments (C1, C2 and C3) was tested with presence or absence of wtMIC-1 through FACS. HEK293-6E cells were transiently transfected with plasmid expressing hGFRAL(ECR) and its fragments (hGFRAL_C1, hGFRAL_C2, hGFRAL_C3, hGFRAL_C1C2, hGFRAL_C2C3) were stained with Ret-Fc protein with the presence or absence of wtMIC-1. GFRAL fragments expression on cell surface was verified by positive staining of anti-mouse-Kappa antibody via flow cytometry analysis. Binding of hRet(ECR)-Fc was detected using APC-conjugated goat Anti-Human IgG (13392/D3-110, Cayman Chemical). Results showed that when there was no wtMIC-1, RET did not bind to hGFRAL(ECR) or its fragments (hGFRAL_C1, hGFRAL_C2, hGFRAL_C3, hGFRAL_C1C2, hGFRAL_C2C3). When wtMIC-1 was present, RET only bound to hGFRAL(ECR) but no other fragments (hGFRAL_C1, hGFRAL_C2, hGFRAL_C3, hGFRAL_C1C2, hGFRAL_C2C3). Considering data in the previous example, i.e., both hGFRAL(ECR) and hGFRAL_C1C2 showed detectable binding to wtMIC-1, and RET bound to the complex of wtMIC-1 and GFRAL, the results of this example indicate that C3 domain is necessary for Ret's binding to the complex of MIC-1 and GFRAL, although C3 is dispensable for MIC-1's binding to GFRAL. Please see FIG. 7, Table 6; and FIG. 8 (showing the relative binding of Ret-Fc* in FIG. 7) and Table 7.

TABLE 6

Figure 7:
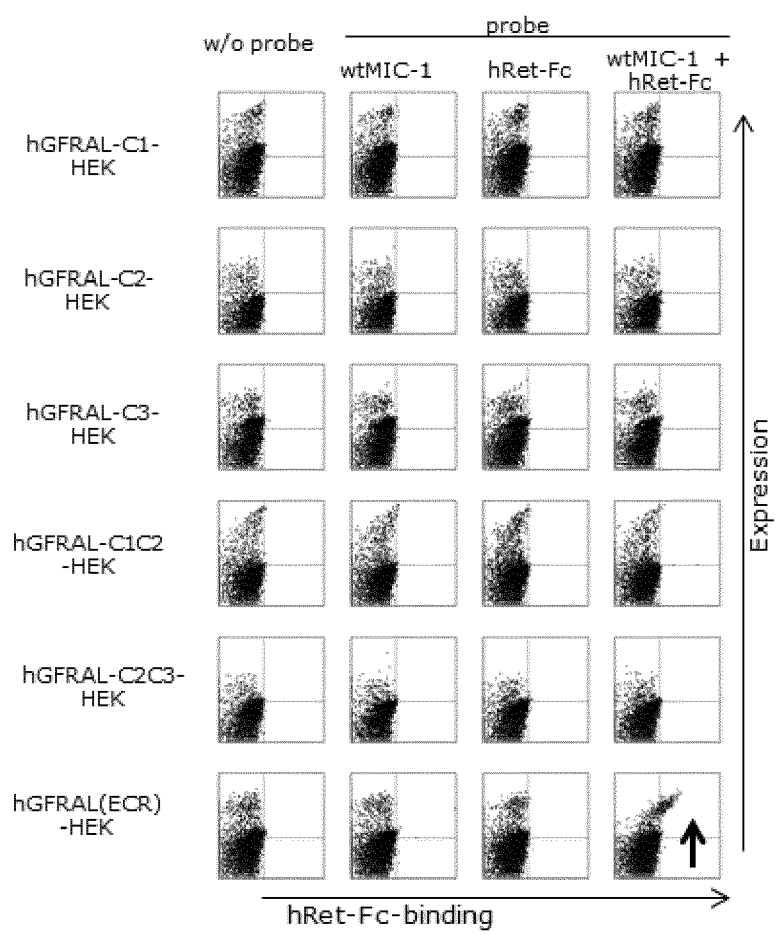
FIG. 7 shows that C3 domain of the extracellular region of GFRAL is necessary for Ret to bind to the MIC-1/GFRAL complex for forming MIC-1/GFRAL/Ret ternary complex, although GFRAL C3 is dispensable for MIC-1 binding to GFRAL.

Meaning of the four quadrants in the FACS dot-plot drawings of FIG. 7

|  | Bio-MIC-1 binding | hRet-Fc binding |
|---|---|---|
| Q1 (upper left) | + | − |
| Q2 (upper right) | + | + |
| Q3 (lower right) | − | + |
| Q4 (lower left) | − | − |

TABLE 7

Figure 8:
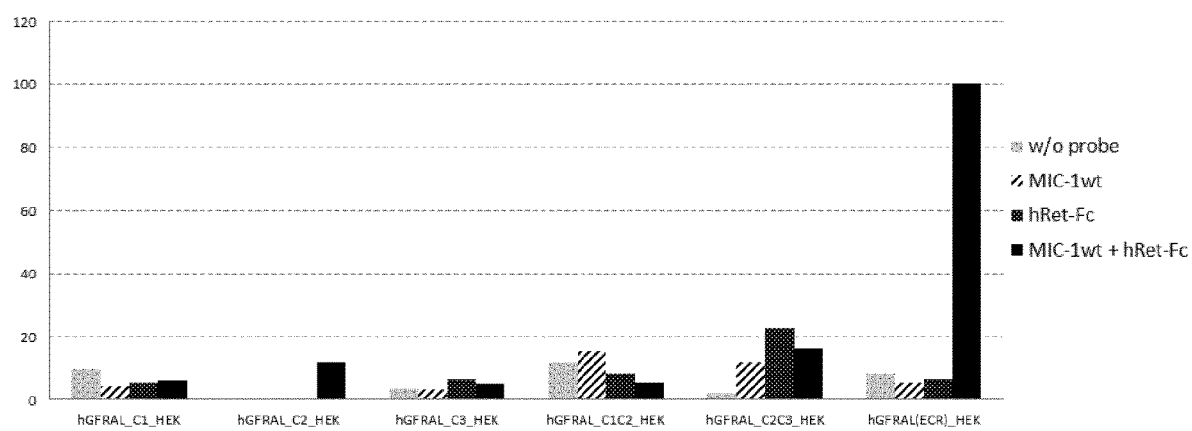
FIG. 8 shows the relative binding of Ret-Fc in the FACS dot-plot drawings of FIG. 7.

Relative binding of Ret-Fc* of FIG. 8

|  | hGFRAL_C1 | hGFRAL_C2 | hGFRAL_C3 | hGFRAL_C1C2 | hGFRAL_C2C3 | hGFRAL (ECR) |
|---|---|---|---|---|---|---|
| w/o probe | 10 | 0 | 4 | 12 | 2 | 8 |
| wtMIC-1 | 4 | 0 | 3 | 15 | 12 | 5 |
| hRet-Fc | 5 | 0 | 6 | 8 | 22 | 6 |
| wtMIC-1 + hRet-Fc | 6 | 12 | 6 | 5 | 16 | 100 |

*Binding between hRet-Fc and hGFRAL(ECR) with presence of wtMIC-1 was detected as the strong-est, thus was set up as 100%

Overall, data in Examples 15 and 16 indicates that GFRAL-C1C2 is critical for MIC-1 binding and GFRAL-C3 is essential for Ret binding to from MIC-1/GFRAL/Ret ternary complex.

Example 14

Generation of Stably-Transformed Mammalian Cells Expressing Both Full Length Human GFRAL and Full Length Human RET Cell Line: PC-12, HEK293
Expression Constructs
  pEL-Full Length-hGFRAL
  Human (Homo sapiens) GDNF family receptor alpha like (hGFRAL) DNA sequence (SEQ ID: 1) is from CCDS4957.1. The DNA sequence encoding the full length GFRAL protein was optimized to remove common restriction sites (EcoRI, BamHI, HindIII, and ApaI) while retaining the GFRAL peptide sequence.
  hGFRAL DNA was synthesized and cloned into expression vector pEL, which contains a CMV promoter to drive expression in the mammalian cells.
  Rat GFRAL (amino acid sequence is shown in SEQ ID NO: 22), cyno GFRAL (amino acid sequence is shown in SEQ ID NO: 20) and mouse GFRAL (amino acid sequence is shown in SEQ ID NO: 4) expression constructs were generated in a similar way as human GFRAL expression construct as described above, by cloning rat, cyno and mouse GFRAL cDNA sequences into expression vector pEL.
  pEL-Full length-hRET51
  Human (Homo sapiens) proto-oncogene tyrosine-protein kinase receptor's (RET51) DNA sequence is from CCDS7200.1 and UniProt P07949-1 (hRET51, amino acid sequence is shown in SEQ ID NO: 5). The DNA sequence encoding the full length GFRAL protein was optimized to remove common restriction sites (EcoRI, BamHI, HindIII, and ApaI) while retaining the RET peptide sequence.

hRET51 DNA was synthesized and cloned into expression vector pEL, which contains a CMV promoter to drive expression in the mammalian cells.

hRET43 (amino acid sequence is shown in SEQ ID NO: 17), hRET9 (amino acid sequence is shown in SEQ ID NO: 18), rat RET(amino acid sequence is shown in SEQ ID NO: 23), cyno RET (amino acid sequence is shown in SEQ ID NO: 21) and mouse RET (amino acid sequence is shown in SEQ ID NO: 19) expression constructs were generated in a similar way as human RET51 expression construct as described above, by cloning rat, cyno and mouse RET cDNA sequences into expression vector pEL. Please note that Rat RET, cyno RET and mouse RET are homolog of hRET51.

Reagent
DMEM (Gibco 10569)
Geneticin(Gibco 10131035)
Hygromycin B (Roche 10843555001)
Lipofectamine 2000 (Invitrogen 11668027)

Process:
1) Seeded 4E6 PC-12 or HEK293 cells in 10 cm dish for O/N.
2) Transfected PC-12 or HEK293 cells with 24 ug pEL-FL-hGFRAL, or pEL-FL-hRET51/43/9, or both pEL-FL-hGFRAL and pEL-FL-hRET51/43/9 in 60 ul Lipofectamine 2000 and culture at 37° C. for O/N.
3) Split the original plate to daughter plates at different ratios 1:10 (2), 1:100 (2), 1:500 (2) and 1:1000 (2),
4) 6 h after, added 10 mL DMEM (containing 2 mg/ml G418) to each dishes, the geneticin concentration in dishes was 1 mg/ml.
5) Cells were collected and mRNA was purified with QIAGEN RNeasy mini kit; cDNA was obtained by Reverse Transcription with Thermoscript RT-PCR system; qPCR with AB Power SYBR Green PCR Master Mix was carried out to test transfection efficiency and the cDNA were kept as positive control for further clones validation use.
6) Cells were with 1 mg/ml geneticin in DMEM for 3 weeks
7) Single clones were picked up to 24 well plate and cells were grew till full confluence
8) Expression of full length-hGFRAL and full length hRET51/43/9 were confirmed by western blot (Sigma, cat #HPA047372), and by qPCR (5'-gaatctaacta-cacgttcccatca-3' and 5'-cagaccacatcccctacaca-3') using the same procedure as above.
9) Positive clones were further validated by functional assay Example 15

Studying of MIC-1 Signaling Transduction

Reagents
DMEM (Gibco 10569)
Hygromycin B (Roche 10843555001)
Trypsin: T4424, Sigma
D-PBS: D8537, Sigma
P/S: 15140-122, Gibco
RIPA buffer (Thermo, cat #89900)
Anti-Ret (phospho Y1062) antibody (Abcam, cat #ab51103)
Phospho-Ret (Tyr905) Antibody (Cell Signaling, cat #3221S)
Phospho-Met (Tyr1234/1235) (D26) XP® Rab (Cell Signaling, cat #3077S)

Phospho-Met (Tyr1003) (13D11) Rabbit mAb (Cell Signaling, cat #3135S)
Phospho-p38 MAPK (Thr180/Tyr182) (D3F9) XP® Rabbit mAb (Cell Signaling, cat #4511)
Phospho-SAPK/JNK (Thr183/Tyr185) (81E11) Rabbit mAb (Cell Signaling, cat #4668)
Phospho-EGF Receptor (Tyr1068) (D7A5) XP® Rabbit mAb (Cell Signaling, cat #3777)
AlphaScreen SureFire ERK1/2 (p-T202/Y204) Assay Kit (PerkinElmer, Catalog #TGRES10K)
AlphaScreen SureFire Akt1/2/3 (p-5473) Assay Kit (Perkin Elmer, Catalog #TGRA4S10K)
AlphaScreen SureFire SMAD1(p-5463/465) Assay Kit (PerkinElmer, Catalog #TGRSM1S10K)
AlphaScreen SureFire SMAD3(p-5423/425) Assay Kit (PerkinElmer, Catalog #TGRSM3S10K)

PC12, HEK293 cells were transfected with full length human GFRAL, or full length human RET51/43/9, or co-transfected with full length human GFRAL and full length human RET51/43/9 using Lipfectamine LTX (Life technologies, 15338100) according to previous example. Twenty-four hours after transfection, cells were seeded on 96 well plates at 1E6/ml. Twenty-four hours later, cells were starved in serum free culture medium for 4 hrs and treated with wild type human wtMIC-1 as indicated for 15 mins. Cells were lysed by Surefire lysis buffer and ERK1/2 phosphorylation (pERK1/2) was measured by Surefire a-screen. Results showed that MIC-1 only induced ERK1/2 phosphorylation in cells co-transfected with full length human GFRAL and full length human RET51, but not in cells transfected with GFRAL only, or in cells transfected with RET51 only. Please see FIG. 9 and Table 8; FIG. 10 and Table 9; and FIG. 11 and Table 10. Results also showed that MIC-1 only induced pERK in cells co-transfected with hRET51 and hGFRAL, not in cells co-transfected with hRET43 and hGFRAL or hRET9 and hGFRAL. Please see FIG. 12 and Table 11.

TABLE 8

| wtMIC-1 induced ERK1/2 phosphorylation in PC12 cells expressing hGFRAL(FL) and hRET51(FL) ||
| --- | --- |
| wtMIC-1 log(nM) | pERK1/2 (Evision Unit) |
| 0.69897 | 800753.8 |
| 0.30103 | 796830.5 |
| −0.09691 | 739949.0 |
| −0.49485 | 709877.5 |
| −0.89279 | 611715.2 |
| −1.29073 | 532987.2 |
| −1.68867 | 496081.5 |
| −2.50000 | 564097.8 |

Figure 9:
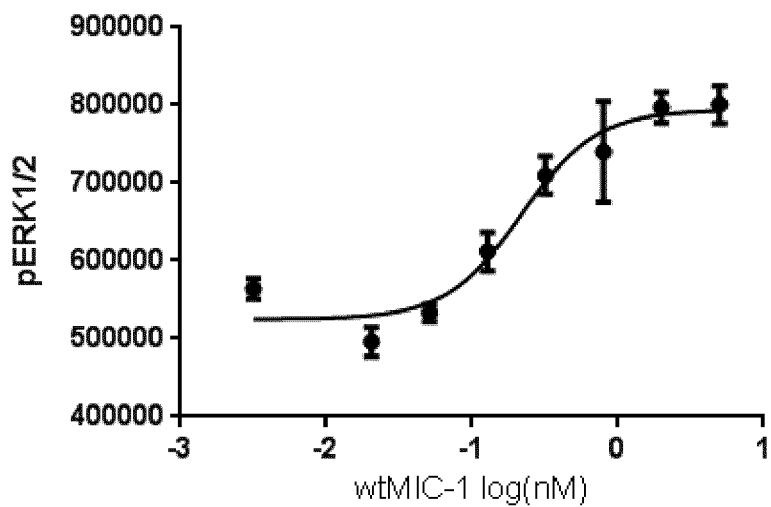
FIG. 9 shows that wtMIC-1 induced ERK1/2 phosphorylation in PC12 cells co-transfected with and expressed full length hGFRAL and full length hRET51.
Figure 10:
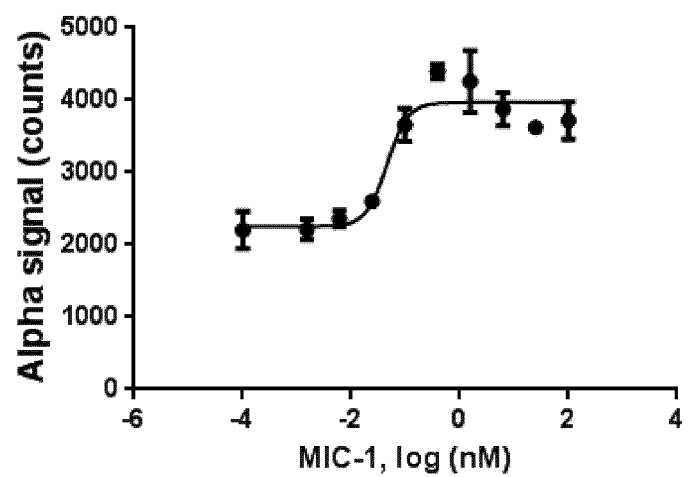
FIG. 10 shows that wtMIC-1 induced ERK1/2 phosphorylation in HEK293 cells co-transfected with and expressed full length hGFRAL and full length hRET51.

Results in Table 8 and FIG. 9 showed that wtMIC-1 dose dependently activated ERK1/2 phosphorylation in hGFRAL and hRET51 co-transfected PC12 cells with an EC50 around 0.2 nM.

TABLE 9

| wtMIC-1 induced ERK1/2 phosphorylation in HEK293 cells co-transfected with hGFRAL(FL) and hRET51(FL) ||
| --- | --- |
| wtMIC-1 (nM) | pERK1/2 (Evision Unit) |
| 100.000000 | 3565 |
| 25.000000 | 3569 |
| 6.250000 | 4215 |
| 1.562500 | 4522 |

TABLE 9-continued wtMIC-1 induced ERK1/2 phosphorylation in HEK293 cells
co-transfected with hGFRAL(FL) and hRET51(FL)

| wtMIC-1 (nM) | pERK1/2 (Evision Unit) |
|---|---|
| 0.390625 | 4361 |
| 0.09765625 | 3529 |
| 0.02441406 | 2632 |
| 0.006103516 | 2321 |

Results in Table 9 and FIG. 10 showed that wtMIC-1 dose dependently activated ERK1/2 phosphorylation in hGFRAL and hRET51 co-transfected HEK293 cells.

TABLE 10 wtMIC-1 did not induce ERK1/2 phosphorylation in PC-12
cells expressing only hGFRAL(FL) or only hRET51(FL)

| | pERK1/2 (Evision Unit) | | | |
|---|---|---|---|---|
| wtMIC-1 (nM) | no-ransfection (wt) | hGFRAL transfected | hRET51 transfected | hGFRAL/hRET51 co-transfected |
| 100.00000 | 96752.3 | 60239.2 | 66502.2 | 393718.7 |
| 33.33330 | 93058.5 | 51846.0 | 59253.7 | 371121.5 |
| 11.11110 | 105186.3 | 53627.0 | 65703.5 | 385059.0 |
| 3.70370 | 96438.67 | 56083.2 | 63068.2 | 375673.0 |
| 1.23460 | 100130.8 | 61954.2 | 65140.5 | 361845.5 |
| 0.41150 | 102684.8 | 61078.3 | 64341.7 | 303567.2 |
| 0.13720 | 108993.7 | 57031.0 | 65766.3 | 213397.5 |
| 0.04570 | 102958.8 | 57841.7 | 67729.7 | 163937.7 |
| 0.01520 | 106936.3 | 52780.5 | 64593.2 | 151551.3 |
| 0.00200 | 109256.7 | 49181.2 | 66674.5 | 146359.7 |

Figure 11:
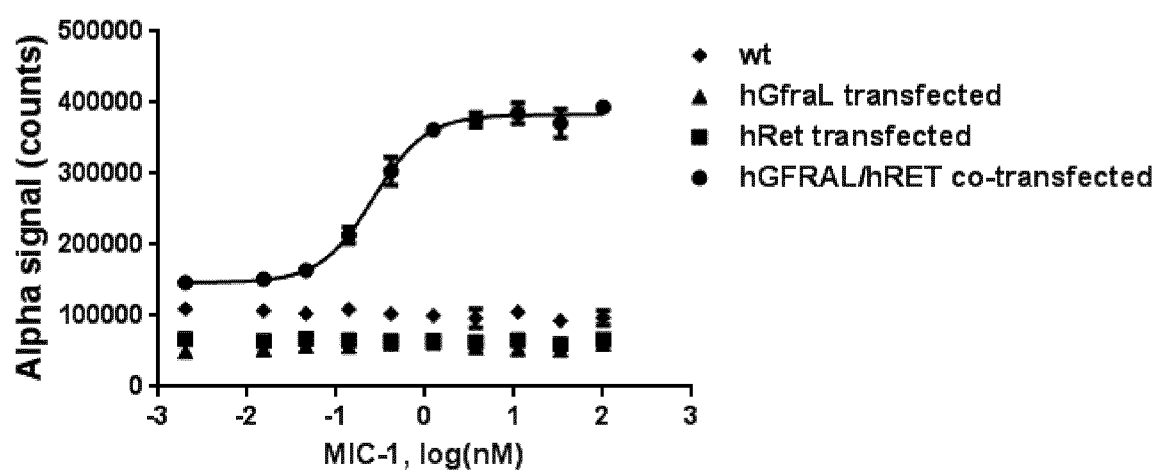
FIG. 11 shows that MIC-1 only induced ERK phosphorylation in cells co-transfected with GFRAL and RET, but not in cells transfected with GFRAL only, or in cells transfected with RET only.
Figure 12:
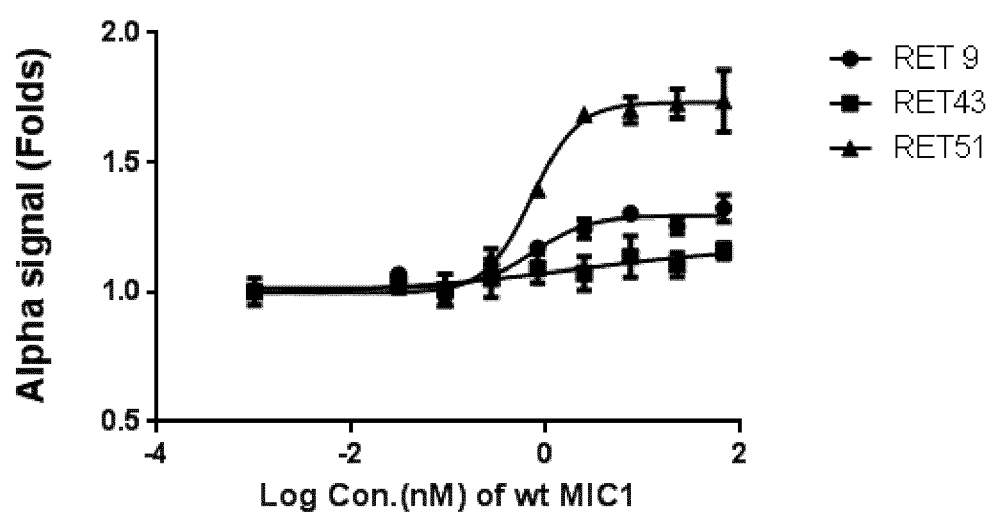
FIG. 12 shows that MIC-1 only induced ERK phosphorylation in cells co-transfected with hRET51 and hGFRAL, not in cells co-transfected with hRET43 and hGFRAL or hRET9 and hGFRAL FIG. 13 showed that MIC-1 can also induced ERK phosphorylation in cells co-transfected with rat GFRAL and rat RET, or cells co-transfected with cynomolgus (cyno) GFRAL and cyno RET.

Results in Table 10 and FIG. 11 showed that wtMIC-1 did not induce ERK1/2 phosphorylation in PC12 cells transfected with only hGFRAL or hRET51, but only cells co-transfected with both hGFRAL and hRET51. Thus, both GFRAL and RET are need for MIC-1 to have activity.

TABLE 11 wtMIC-1 did not induce pERK in HEK293 cells co-transfected
with RET43/9 and hGFRAL, but pERK only in HEK293 cells
co-transfected with RET51 and hGFRAL

| | pERK1/2 (Evision Unit) | | |
|---|---|---|---|
| wtMIC-1 (nM) | RET 9 | RET43 | RET51 |
| 66.666670 | 1.323266 | 1.158630 | 1.737150 |
| 22.222220 | 1.255731 | 1.105068 | 1.727052 |
| 7.407407 | 1.302666 | 1.136891 | 1.701729 |
| 2.469136 | 1.244610 | 1.072073 | 1.686027 |
| 0.823045 | 1.170909 | 1.090099 | 1.395468 |
| 0.274348 | 1.069708 | 1.051677 | 1.132260 |
| 0.091449 | 0.988070 | 1.009341 | 0.969390 |
| 0.030483 | 1.066978 | 1.034423 | 1.023812 |
| 0.001000 | 1.000000 | 1.000000 | 1.000000 |

Example 16

Cross-Species Reaction of MIC-1

BHK cells were co-transfected with full length rat GFRAL and rat RET (homolog of hRET51), or cyno GFRAL and cyno RET (homolog of hRET51) using Lipfectamine LTX (Life technologies, 15338100) according to previous example. Twenty-four hours after transfection, cells were seeded on 96 well plates at 1E6/ml. Twenty-four hours later, cells were starved in serum free culture medium for 4 hrs and treated with wild type human wtMIC-1 as indicated for 15 mins. Cells were lysed by Surefire lysis buffer and ERK1/2 phosphorylation (pERK1/2) was measured by Surefire a-screen.

Figure 13:
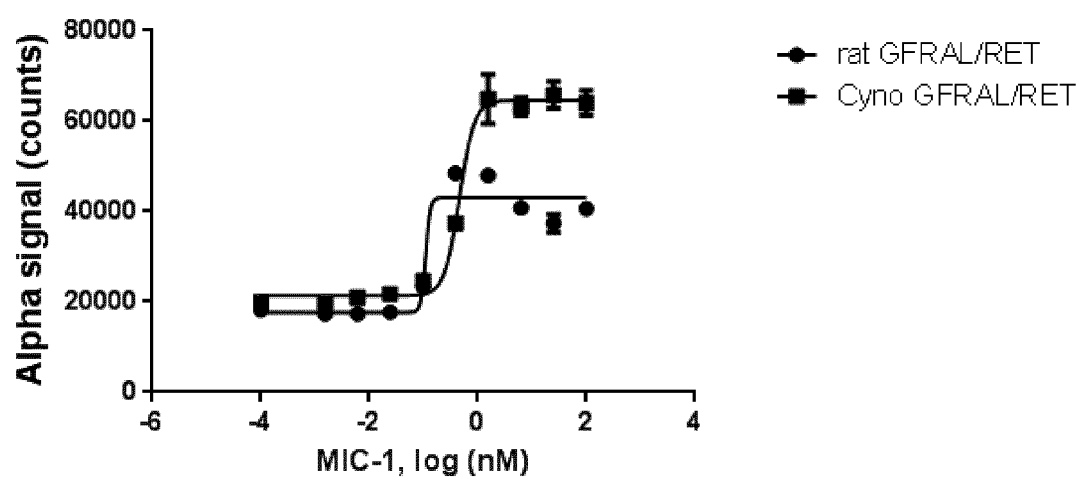

Results showed that MIC-1 also induced ERK1/2 phosphorylation in cells co-transfected with rat GFRAL and rat RET, or cells co-transfected with cyno GFRAL and cyno RET. This means that human MIC-1 has cross-species activity, which would significantly facilitate drug development, since the same MIC-1 compound could be applied to animals in pre-clinical trials and clinical trials. Please see FIG. 13 and Table 12.

TABLE 12 wtMIC-1 induced pERK in rat and cyno GFRAL/RET
transfected BHK21 cells

| | pERK1/2 (Evision Unit) | |
|---|---|---|
| wtMIC-1 (nM) | rat GFRAL/RET | Cyno GFRAL/RET |
| 100.000000 | 40572.00 | 63944.25 |
| 25.000000 | 37384.75 | 65745.25 |
| 6.250000 | 40738.75 | 63194.50 |
| 1.562500 | 47997.75 | 64888.25 |
| 0.390625 | 48433.75 | 37388.75 |
| 0.09765625 | 23426.75 | 24647.75 |
| 0.02441406 | 17716.50 | 21785.25 |
| 0.006103516 | 17309.50 | 20982.50 |
| 0.001525879 | 172810 | 19753.50 |
| 0.000100 | 18255.50 | 19986.25 |

Results in Table 12 showed that cross-species activity of human wtMIC-1 with rat GFRAL/RET and cyno GFRAL/RET.

Based on the results above, we believe GFRAL is the cell surface receptor that mediates the in vivo activities of MIC-1. In particular, GFRAL binds to MIC-1, then RET binds to the complex of GFRAL and MIC-1 to form ternary complex. Such ternary complex phosphorylates RET protein tyrosine kinase to induce in vivo activities of MIC-1 through signal pathways comprising at least comprising ERK/MAPK pathway by phosphorylation of ERK1/2 pathway.

Example 17

Further Studying of MIC-1 Signaling Transduction

Figure 14:
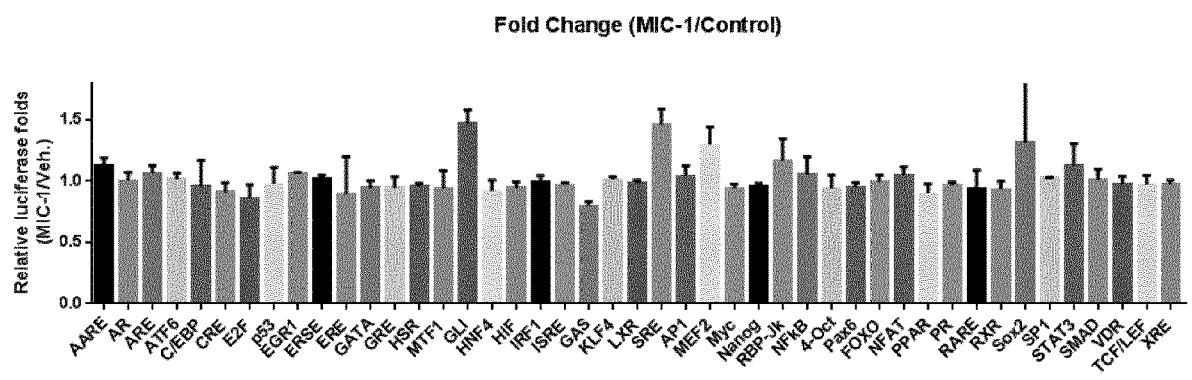
FIG. 14 showed that Hedgehog, MEF2 and MAPK/ERK signaling pathways were regulated upon MIC-1 treatment, as evidenced by up-regulation of GLI, MEF2 and SRE derived luciferase reporter activities respectively when tested by Cignal 45-pathway Reporter Array.

In order to profile MIC-1 induced signaling systematically, MIC-1 function on GFRAL/RET co-transfected BHK21 cells was examined by Cignal 45-pathway following the manufacturer's protocol.
Reagent:
Cignal 45-pathway Reporter Array (Qiagen: CCA-901L)
Dual-Glo® Luciferase Assay System (Promega: E2940)
Briefly, BHK21 cells were seeded on Cignal 45-pathway plates and transfected with hGFRAL and hRET plasmids as described above. The transfected were treated with 10 nM wild type hMIC-1 for 4 hours and Luciferase signal was quantified.
Cignal 45-pathways results showed that Hedgehog, MEF2 and MAPK/ERK signaling pathways were regulated upon MIC-1 treatment, as evidenced by significant upregulation of GLI, MEF2 and SRE derived luciferase reporter activities respectively (according to 1 way ANOVA, p<0.05 for MIC-1 vs. inactive MIC-1 analogue). Please see FIG. 14.

However, we did not observe the MIC-1 induced FOXO activity (corresponding to the pathway comprising AKT1/2/3 phosphorylation) in this experiment, which we believe was due to that MIC-1 response window or assay sensitivity of this specific pathway is not sufficient to be observed by this assay.

Furthermore, regulation of GLI and MEF2 signaling was confirmed by quantification of GLI and MEF2 mRNA expression in wtMIC-1 treated BHK21 cells by qPCR.

Example 18

Establishment of BHK21-hGFRAL-IRES-hRET-SRE-Luc Stable Cells

Figure 15:
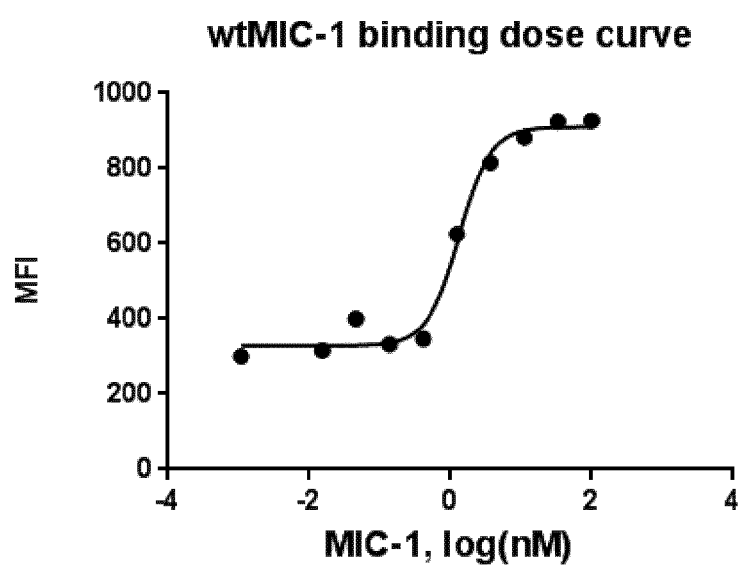
FIG. 15 shows that wtMIC-1 bound to BHK21 cells co-transfected and expressed full length hGFRAL and full length hRET in a dose-dependent manner.
Figure 16:
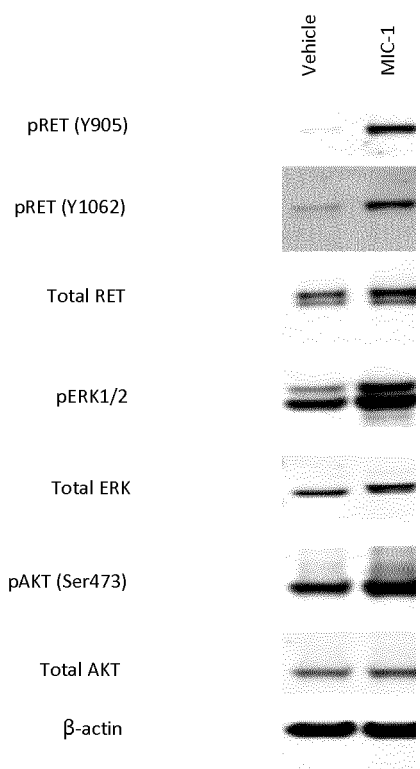
FIG. 16 shows that wtMIC-1 induced both phosphorylation of ERK and AKT in BHK21-hGFRAL-IRES-hRET stable cells. Western blot showed the protein level change of phosphorylation of ERK1/2 and AKT1/2/3 after wtMIC-1 induction.
Figure 17:
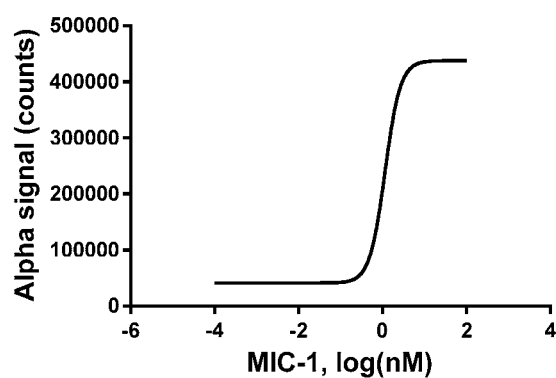
FIG. 17 shows that wtMIC-1 induced ERK1/2 phosphorylation in BHK21-hGFRAL-IRES-hRET stable cells in a dose-dependent manner.
Figure 18:
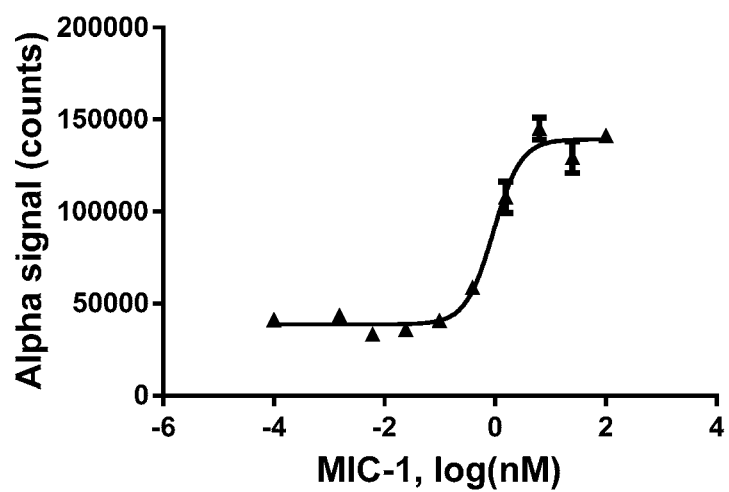
FIG. 18 shows that wtMIC-1 induced AKT1/2/3 phosphorylation in BHK21-hGFRAL-IRES-hRET stable cells in a dose-dependent manner.

The purpose of this example was to establish a cell based in vitro assay for testing MIC-1 activity. Mammalian cells were transfected and stably expressed full length hGFRAL and full length hRET51; and the activity of MIC-1 can be examined by detecting luciferase activity.
Cell line: BHK21 Cells (ATCC: tk-ts13)
Plasmid
 pEL-hGFRAL-IRES-hRET Plasmids expressing full length hGFRAL and full length hRET51 were constructed by inserting synthesized DNA nucleotides encoding full length hGFRAL and full length hRET51 into mammalian expression vector pEL. IRES (internal ribosome entry site) is a commonly used linker between two DNA sequences, so that the two DNA sequences can be simultaneously translated into mRNA. pEL vector backbone was provided by Taihegene CRO company.
 pGL4.33-SRE-Luc Plasmids expressing luciferase were constructed by inserting synthesized DNA sequence of luciferase into mammalian expression vector pGL4.33. SRE is the abbreviation of "serum response element". When MIC-1 binds to GFRAL and RET, ERK is phosphorylated as pERK. pERK can increase the expression of serum response factor, and serum response factor binds to SRE to up regulate the expression of luciferase, so that MIC-1 activity can be tested and indicated as the activity of luciferase. pGL4.33 vector backbone was provided by Taihegene CRO company.
Reagent
 DMEM (Gibco 10569)
 Geneticin(Gibco 10131035)
 Hygromycin B (Roche 10843555001)
 Lipofectamine 2000 (Invitrogen 11668027)
Process:
Generation of BHK21-hGFRAL-IRES-hRET Stable Cells Two millions of BHK21 cells were seeded in a 10 cm petri dish and cultured for overnight in culture medium (DMEM+10% FBS+1% PS). Cells were transfected with pEL-hGFRAL-IRES-hRET plasmids. Transfected cells were split into new 10 cm dishes at different densities and grew in selection medium (DMEM+10% FBS+1% PS+1 mg/ml G418) for more than 2 weeks to get single clones. The single clones were transferred to 6 well plates and cultured to 100% confluence. mRNA expression of hGFRAL and hRET was measured by qPCR. Successfully transfected clones were picked up and tested for MIC-1 binding (FIG. 15 and Table 13). MIC-1 induced both phosphorylation of ERK and AKT in BHK21-hGFRAL-IRES-hRET stable cells. Please see FIG. 16, FIG. 17 and Table 14, and FIG. 18 and Table 15. The results show that the ternary complex of MIC-1, GFRAL and RET phosphorylates RET protein tyrosine kinase to induce in vivo activities of MIC-1 through signal pathways comprising not only ERK/MAPK pathway by phosphorylation of ERK1/2 pathway, but also PI3K/Akt pathway by phosphorylation of AKT1/2/3.

One clone that had the best RET/ERK/AKT phosphorylation level was selected for further transfection of pGL4.33-SRE-Luc plasmids.

TABLE 13 wtMIC-1 binds to BHK21-hGFRAL-IRES-hRET stable cells (EC50 = 1.3 nM)

| wtMIC-1 (nM) | wtMIC-1 binding (MIF: median fluorescence intensity) |
|---|---|
| 100 | 926 |
| 33.33333333 | 924 |
| 11.11111111 | 882 |
| 3.703703704 | 816 |
| 1.234567901 | 625 |
| 0.411522634 | 347 |
| 0.137174211 | 333 |
| 0.045724737 | 400 |
| 0.015241579 | 316 |
| 0.001 | 300 |

TABLE 14 wtMIC-1 induced ERK phosphorylation in BHK21-hGFRAL-IRES-hRET stable cells

| wtMIC-1 (nM) | ERK1/2 phosphorylation (alpha signal (counts)) |
|---|---|
| 100 | 436226 |
| 25 | 429956 |
| 6.25 | 442116 |
| 1.5625 | 308222 |
| 0.390625 | 72323 |
| 0.097656 | 41955 |
| 0.024414 | 42171 |
| 0.006104 | 35645 |
| 0.001526 | 40198 |
| 0.0001 | 44930 |

TABLE 15 wtMIC-1 induced AKT phosphorylation in BHK21-hGFRAL-IRES-hRET stable cells

| wtMIC-1 (nM) | AKT1/2/3 phosphorylation (alpha signal (counts)) |
|---|---|
| 100 | 141354 |
| 25 | 129392 |
| 6.25 | 145118 |
| 1.5625 | 107735 |
| 0.390625 | 58760 |
| 0.097656 | 40976 |
| 0.024414 | 35777 |
| 0.006104 | 33394 |
| 0.001526 | 43367 |
| 0.0001 | 41320 |

Generation of BHK21-hGFRAL-IRES-hRET-SRE-Luc Stable Cells

The selected clone of BHK21-hGFRAL-IRES-hRET cells was grown to two million. Then the two million BHK21-hGFRAL-IRES-hRET cells were seeded in a 10 cm petri dish and cultured in culture medium 2 (DMEM+10% FBS+1% PS+1 mg/ml G418). Cells were transfected with pGL4.33-SRE-Luc plasmids (seq.2) following the standard protocol. Transfected cells were split into new 10 cm dishes at different densities and grew in selection medium (DMEM+10% FBS+1% PS+1 mg/ml G418+hygromycin 400 µg/ml) for more than 2 weeks to get single clones. The single clones were transferred to 6 well plates and cultured to 100% confluence. Clones were tested for induction of luciferase activity upon wtMIC-1 treatment. Clones that showed high luciferase activity induced by wtMIC-1 were cultured and cryopreserved.

Figure 19:
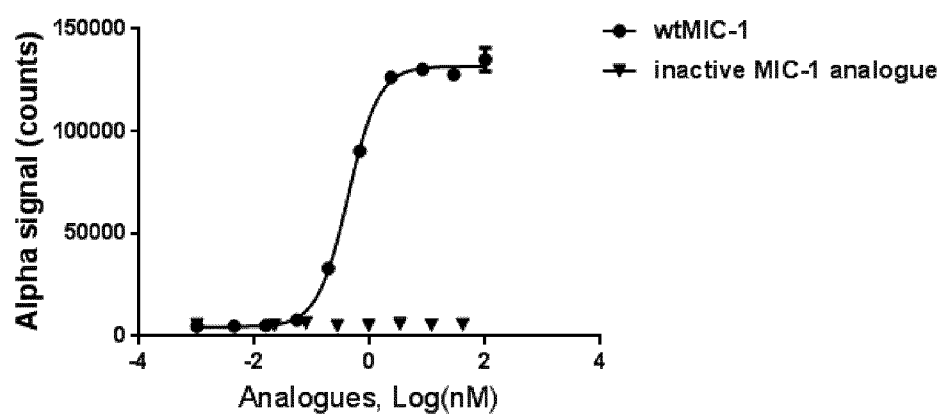
FIG. 19 shows that wtMIC-1 induced ERK1/2 phosphorylation in BHK21-hGFRAL-IRES-hRET-SRE-Luc stable cells cells in a dose-dependent manner.

MIC-1 Induced ERK Phosphorylation in BHK21-hGFRAL-IRES-hRET-SRE-Luc Stable Cells BHK21-hGFRAL-IRES-hRET-SRE-Luc stable cells were seeded at 2E4 cells per well in 96-well plates and cultured for overnight. Medium was removed and replenished with 100 µl serum free DMEM for 4 hours. Different concentrations of wtMIC-1 were added to the medium and incubated for 15 minutes. ERK1/2 was quantified by ERK1 (p-Thr 202) and ERK2 (p-Thr204) alphascreen Surefire assay kits following manufacturer instructions. Dose response curves were generated by nonlinear regression curve fit (4-parameters) with GraphPad Prism. Results were shown in FIG. 19 and Table 16.

TABLE 16 wtMIC-1 induced ERK1/2 phosphorylation in BHK21-hGFRAL-IRES-hRET-SRE-Luc stable cells

| wtMIC-1 (nM) | ERK1/2 phosphorylation (alpha signal (counts)) | Control (inactive MIC-1 analogue) (alpha signal (counts)) |
| --- | --- | --- |
| 100 | 134920.5 | 5502.5 |
| 28.57143 | 127624.5 | 5331.0 |
| 8.163265 | 130249.0 | 5783.5 |
| 2.332362 | 126250.5 | 5111.5 |
| 0.666389 | 90359.0 | 4970.0 |
| 0.190397 | 32908.5 | 6292.5 |
| 0.054399 | 7851.0 | 5058.5 |
| 0.015543 | 5010.0 | 5388.5 |
| 0.004441 | 4751.5 | N/A |
| 0.001 | 4736.0 | N/A |

MIC-1 Activated Luciferase in BHK21-hGFRAL-IRES-hRET-SRE-Luc Stable Cells

Figure 20:
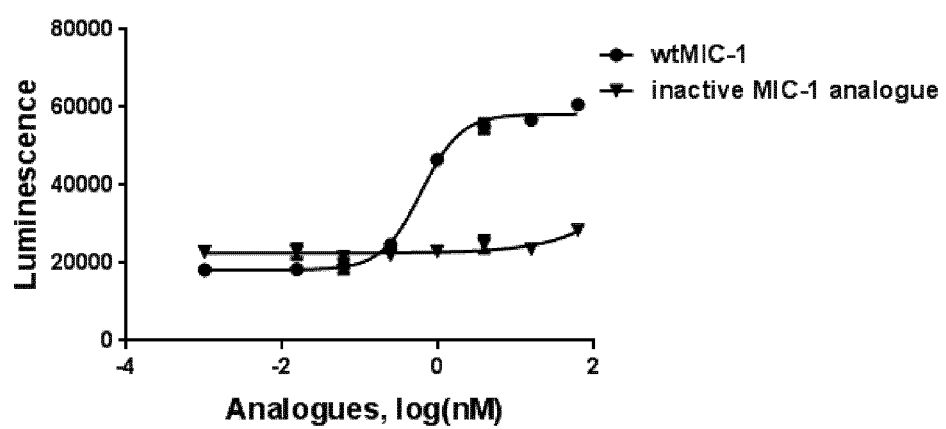
FIG. 20 shows that wtMIC-1 activated luciferase in BHK21-hGFRAL-IRES-hRET-SRE-Luc stable cells in a dose-dependent manner

BHK21-hGFRAL-IRES-hRET-SRE-Luc stable cells were seeded at 4E4 cells per well in 96-well plates and 6 hours after cell seeding, medium was removed and replenished with 100 µl serum free DMEM for overnight. Different concentrations of wtMIC-1 were added to the medium and incubated for 4 hours. Steady light plus (PE 6016751) was added to the plates and incubated for 30 min at room temperature. The signal was measured in Envision, ultra luminescence and dose response curves were generated by nonlinear regression curve fit (4-parameters) with GraphPad Prism. Results were shown in FIG. 20 and below Table 17.

TABLE 17 wtMIC-1 activated luciferase in BHK21-hGFRAL-IRES-hRET-SRE-Luc stable cells

| wtMIC-1 (nM) | Luminescence activity (alpha signal (counts)) | Control (inactive MIC-1 analogue) (alpha signal (counts)) |
| --- | --- | --- |
| 62.5 | 60700 | 28380 |
| 15.625 | 56800 | 23580 |
| 3.90625 | 55140 | 24780 |
| 0.976563 | 46560 | 22940 |
| 0.244141 | 24720 | 22000 |
| 0.061035 | 19220 | 21540 |
| 0.015259 | 18380 | 22960 |
| 0.001 | 18220 | 22860 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An in vitro cell line for determining the activity of a MIC-1 compound, wherein the cell line recombinantly expresses a human GDNF family receptor alpha like (GFRAL) comprising the amino acid sequence set forth in SEQ ID NO:2, a hRET comprising the amino acid sequence set forth in SEQ ID NO:5, and a reporter peptide.

2. The in vitro cell line according to claim 1, wherein the reporter peptide is selected from the group consisting of luciferase, bacterial β-galactosidase, trpE, Protein A, β-lactamase, alpha amylase, alcohol dehydrogenase, and yeast alpha mating factor.

3. The in vitro cell line according to claim 2, wherein the reporter peptide is luciferase.

* * * * *

SEQUENCE LISTING

<160> NUMBER OF SEQ ID NOS: 23

<210> SEQ ID NO 1
<211> LENGTH: 1910
<212> TYPE: DNA
<213> ORGANISM: Homo sapiens

<400> SEQUENCE: 1

```
ttattctgga cagttactct taagaaagtt gtcagaagaa acgcatctgc cttttttttc      60
caggtgaact gccgtgagtt gtccagcatg atagtgttta ttttcttggc tatggggtta     120
agcttggaaa atgaatacac ttcccaaacc aataattgca catatttaag agagcaatgc     180
ttacgtgatg caaatggatg taaacatgct tggagagtaa tggaagatgc ctgcaatgat     240
tcagatccag gtgacccctg caagatgagg aattcatcat actgtaacct gagtatccag     300
tacttagtgg aaagcaattt ccaatttaaa gagtgtcttt gcactgatga cttctattgt     360
actgtgaaca aactgcttgg aaaaaaatgt atcaataaat cagataacgt gaaagaggat     420
aaattcaaat ggaatctaac tacacgttcc catcatggat tcaaagggat gtggtcctgt     480
ttggaagtgg cagaggcatg tgtaggggat gtggtctgta atgcacagtt ggcctcttac     540
```

```
cttaaagctt gctcagcaaa tggaaatccg tgtgatctga acagtgccaa agcagccata    600
cggttcttct atcaaaatat acctttaac attgcccaga tgttggcttt ttgtgactgt    660
gctcaatctg atataccttg tcagcagtcc aaagaagctc ttcacagcaa acatgtgca    720
gtgaacatgg ttccaccccc tacttgcctc agtgtaattc gcagctgcca aaatgatgaa    780
ttatgcagga ggcactatag aacatttcag tcaaaatgct ggcagcgtgt gactagaaag    840
tgccatgaag atgagaattg cattagcacc ttaagcaaac aggacctcac ttgttcagga    900
agtgatgact gcaaagctgc ttacatagat atccttggga cggtccttca agtgcaatgt    960
acctgtagga ccattacaca aagtgaggaa tctttgtgta agattttcca gcacatgctt   1020
catagaaaat catgtttcaa ttatccaacc ctgtctaatg tcaaaggcat ggcattgtat   1080
acaagaaaac atgcaaacaa aatcacttta actggatttc attccccctt caatggagaa   1140
gtaatctatg ctgccatgtg catgacagtc acctgtggaa tccttctgtt ggttatggtc   1200
aagcttagaa cttccagaat atcaagtaaa gcaagagatc cttcaccgat ccaaatacct   1260
ggagaactct gattcattag gagtcatgga cctataacaa tcactctttt ctctgctttt   1320
cttctttcct cttttcttct cttctctcct ctcctctctt ctcctctcct cccctcccct   1380
ctctgttct ttttcttttt cttttctttt ttgtggtgga gttttgctct tgttgcccag   1440
gctgcagtac aatggctcaa tctcggttca ctgcaacctc tgcctccaag gttcaagtga   1500
ttttcctgcc tcagcctccc gagtagctgg gattacaggt acccgccacc acgcccagct   1560
aatttttttg tatttttagt agagatgggg ttttgccaaa ttggccaggg tggtctcaaa   1620
ctcctgacct caggtgatcc acccaccctcg gcctcccaaa gtgctgggat tacaggcgtg   1680
agcaaccacg tcaagacaac aatcactttc tttaaagcaa atcctacagc tggtcaacac   1740
actattccat ctgtcatcga gaagaaaat gttaaaatag acttaaaaat attgctttgt    1800
tacatataat aatatggcat gatgatgtta ttttttctt aatactcaag aaaaatatat    1860
ggtggtatct tttacaacac tggaacagaa ataaagttc ccttgaaggc                1910
```

<210> SEQ ID NO 2
<211> LENGTH: 394
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: TRANSMEM
<222> LOCATION: (352)..(371)

<400> SEQUENCE: 2

```
Met Ile Val Phe Ile Phe Leu Ala Met Gly Leu Ser Leu Glu Asn Glu
1               5                   10                  15

Tyr Thr Ser Gln Thr Asn Asn Cys Thr Tyr Leu Arg Glu Gln Cys Leu
            20                  25                  30

Arg Asp Ala Asn Gly Cys Lys His Ala Trp Arg Val Met Glu Asp Ala
        35                  40                  45

Cys Asn Asp Ser Asp Pro Gly Asp Pro Cys Lys Met Arg Asn Ser Ser
    50                  55                  60

Tyr Cys Asn Leu Ser Ile Gln Tyr Leu Val Glu Ser Asn Phe Gln Phe
65                  70                  75                  80

Lys Glu Cys Leu Cys Thr Asp Asp Phe Tyr Cys Thr Val Asn Lys Leu
                85                  90                  95

Leu Gly Lys Lys Cys Ile Asn Lys Ser Asp Asn Val Lys Glu Asp Lys
```

```
            100                 105                 110
Phe Lys Trp Asn Leu Thr Thr Arg Ser His His Gly Phe Lys Gly Met
        115                 120                 125

Trp Ser Cys Leu Glu Val Ala Glu Ala Cys Val Gly Asp Val Val Cys
130                 135                 140

Asn Ala Gln Leu Ala Ser Tyr Leu Lys Ala Cys Ser Ala Asn Gly Asn
145                 150                 155                 160

Pro Cys Asp Leu Lys Gln Cys Gln Ala Ala Ile Arg Phe Phe Tyr Gln
                165                 170                 175

Asn Ile Pro Phe Asn Ile Ala Gln Met Leu Ala Phe Cys Asp Cys Ala
            180                 185                 190

Gln Ser Asp Ile Pro Cys Gln Gln Ser Lys Glu Ala Leu His Ser Lys
        195                 200                 205

Thr Cys Ala Val Asn Met Val Pro Pro Thr Cys Leu Ser Val Ile
210                 215                 220

Arg Ser Cys Gln Asn Asp Glu Leu Cys Arg Arg His Tyr Arg Thr Phe
225                 230                 235                 240

Gln Ser Lys Cys Trp Gln Arg Val Thr Arg Lys Cys His Glu Asp Glu
                245                 250                 255

Asn Cys Ile Ser Thr Leu Ser Lys Gln Asp Leu Thr Cys Ser Gly Ser
            260                 265                 270

Asp Asp Cys Lys Ala Ala Tyr Ile Asp Ile Leu Gly Thr Val Leu Gln
        275                 280                 285

Val Gln Cys Thr Cys Arg Thr Ile Thr Gln Ser Glu Glu Ser Leu Cys
    290                 295                 300

Lys Ile Phe Gln His Met Leu His Arg Lys Ser Cys Phe Asn Tyr Pro
305                 310                 315                 320

Thr Leu Ser Asn Val Lys Gly Met Ala Leu Tyr Thr Arg Lys His Ala
                325                 330                 335

Asn Lys Ile Thr Leu Thr Gly Phe His Ser Pro Phe Asn Gly Glu Val
            340                 345                 350

Ile Tyr Ala Ala Met Cys Met Thr Val Thr Cys Gly Ile Leu Leu Leu
        355                 360                 365

Val Met Val Lys Leu Arg Thr Ser Arg Ile Ser Ser Lys Ala Arg Asp
    370                 375                 380

Pro Ser Ser Ile Gln Ile Pro Gly Glu Leu
385                 390

<210> SEQ ID NO 3
<211> LENGTH: 2080
<212> TYPE: DNA
<213> ORGANISM: Mus musculus

<400> SEQUENCE: 3
aacaattgaa tttgaataca attaggaaag ttcacagctc aaaacaaact ggtgaggaac    60
agctgacacc agaagctgac tctaattggc tggctcttag gaagcaaaac ctttacacag   120
aaacttcagt tgggatgttg gttggtgtca gctcatccgc ctttctccca gggagaccat   180
cttgagttgt ccaacatgct agtgttcatt ttcctggctg ttacgttaag ctcagaaaat   240
gaatcctctt cccaaacaaa tgattgtgca catttaatac agaaatgctt gattgatgca   300
aatggctgtg agcagtcatg gagatcaatg gaagacacct gccttactcc aggtgactcc   360
tgcaagataa ataattcact acattgtaac ctgagtatcc aggcttttggt ggaaaaaaat   420 ttccaattta aagagtgtct ttgtatggat gacctccact gtacagtaaa caaacttttt   480
```

-continued

```
ggaaaaaagt gcaccaataa gacagataac atggaaaagg acaataaaga taaatggaat    540
ctaactacta ctcctttcta tcatggattc aaacagatgc agtcttgttt ggaggtgaca    600
gaggcgtgtg tagggatgt ggtttgtaat gcacagttgg ccctttacct taaagcatgc    660
tcagcaaatg gaaatctgtg tgatgtgaaa cactgccaag cagccatacg gttcttctat    720
caaaatatgc cttttaacac tgcccagatg ttggcttttt gtgactgtgc tcaatctgat    780 atacctgtc agcaatccaa agaaactctt cacagcaagc catgtgcact gaatatagtt    840 ccaccccca cttgcctcag tgtaattcac acttgccgaa atgatgaatt atgcaggaca    900
cactaccgaa cattccagac agaatgctgg ccccacataa ctgggaagtg ccatgaagat    960
gagacctgca ttagcatgtt aggcaagcaa gaccttactt gttctgggag tgagagctgc   1020
agggctgcct tcctaggaac ctttgggaca gtcctgcaag tacccgtgc ttgcaggggc   1080 gttacacagg ctgaagaaca cgtgtgcatg attttccagc acatgcttca tagcaaatcg   1140
tgtttcaatt acccaactcc taatgtcaaa gacatttcct catatgaaaa aaagaattca   1200
aaagaaatta ctctgactgg attcaattct ttcttcaatg gagaactact ctatgttgtt   1260
gtatgcatgg cagttacctg tggaattctt ttccttggtga tgctcaagtt aaggatacaa   1320
agtgaaaaaa gagatccctc atccatcgaa atagctggag gtgtcatcat tcagtgagct   1380
gcagatcact taccaaccac atgtctgtgt gactaaccaa tggaaaatta catttgccaa   1440
taacgcaatt taagatggat ttgacaatat ttagtcatta tatgtaacag tgactggtac   1500
agtaatatac cacaatgatc acagatctgt ttttgttttt gtttttaatg tttgagtaaa   1560
tacttgttgt ggtgtcataa ctagttgata acattttctt taaagacaac aggtgtcatg   1620
taaaatgtga caaatttgct ggaagactat caatccacat atcaacttct atcttatgga   1680
actaatcata attagtgtgt gcagttttct gaacaaggtt atagttttcc attaagttgg   1740
taaaattaaa atgctaagta gaatattgag tatacttgtt atttatatat tcttacttag   1800
tgtccaatca ttaaacaaat tggtaacatt gaacatattt agttagatga ctgcttatga   1860
aaataagaac tgcatctta caaatttat aatttaaata gtattgaatt ttacttttta   1920
tttggtatgt taagattcat aatatataaa gcagctacat tggttgagaa aagtcaatgg   1980
ttactccagt aatgatatac tttgtgaatt tatttatttt tgctaattaa tgatcctgaa   2040
tgtaatcatg atgaaataaa aaagacatac ttaaattgct                         2080
```

<210> SEQ ID NO 4
<211> LENGTH: 393
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: VARSPLIC
<222> LOCATION: (1)..(393)
<223> OTHER INFORMATION: membrane protein; alternatively spliced
<220> FEATURE:
<221> NAME/KEY: TRANSMEM
<222> LOCATION: (350)..(370)

<400> SEQUENCE: 4

Met Leu Val Phe Ile Phe Leu Ala Val Thr Leu Ser Ser Glu Asn Glu
1               5                   10                  15

Ser Ser Ser Gln Thr Asn Asp Cys Ala His Leu Ile Gln Lys Cys Leu
            20                  25                  30

```
Ile Asp Ala Asn Gly Cys Glu Gln Ser Trp Arg Ser Met Glu Asp Thr
         35                  40                  45
Cys Leu Thr Pro Gly Asp Ser Cys Lys Ile Asn Asn Ser Leu His Cys
 50                  55                  60
Asn Leu Ser Ile Gln Ala Leu Val Glu Lys Asn Phe Gln Phe Lys Glu
 65                  70                  75                  80
Cys Leu Cys Met Asp Asp Leu His Cys Thr Val Asn Lys Leu Phe Gly
                 85                  90                  95
Lys Lys Cys Thr Asn Lys Thr Asp Asn Met Glu Lys Asp Asn Lys Asp
                100                 105                 110
Lys Trp Asn Leu Thr Thr Thr Pro Phe Tyr His Gly Phe Lys Gln Met
            115                 120                 125
Gln Ser Cys Leu Glu Val Thr Glu Ala Cys Val Gly Asp Val Val Cys
        130                 135                 140
Asn Ala Gln Leu Ala Leu Tyr Leu Lys Ala Cys Ser Ala Asn Gly Asn
145                 150                 155                 160
Leu Cys Asp Val Lys His Cys Gln Ala Ala Ile Arg Phe Phe Tyr Gln
                165                 170                 175
Asn Met Pro Phe Asn Thr Ala Gln Met Leu Ala Phe Cys Asp Cys Ala
                180                 185                 190
Gln Ser Asp Ile Pro Cys Gln Ser Lys Glu Thr Leu His Ser Lys
            195                 200                 205
Pro Cys Ala Leu Asn Ile Val Pro Pro Thr Cys Leu Ser Val Ile
        210                 215                 220
His Thr Cys Arg Asn Asp Glu Leu Cys Arg Thr His Tyr Arg Thr Phe
225                 230                 235                 240
Gln Thr Glu Cys Trp Pro His Ile Thr Gly Lys Cys His Glu Asp Glu
                245                 250                 255
Thr Cys Ile Ser Met Leu Gly Lys Gln Asp Leu Thr Cys Ser Gly Ser
                260                 265                 270
Glu Ser Cys Arg Ala Ala Phe Leu Gly Thr Phe Gly Thr Val Leu Gln
            275                 280                 285
Val Pro Cys Ala Cys Arg Gly Val Thr Gln Ala Glu Glu His Val Cys
        290                 295                 300
Met Ile Phe Gln His Met Leu His Ser Lys Ser Cys Phe Asn Tyr Pro
305                 310                 315                 320
Thr Pro Asn Val Lys Asp Ile Ser Ser Tyr Glu Lys Lys Asn Ser Lys
                325                 330                 335
Glu Ile Thr Leu Thr Gly Phe Asn Ser Phe Asn Gly Glu Leu Leu
            340                 345                 350
Tyr Val Val Cys Met Ala Val Thr Cys Gly Ile Leu Phe Leu Val
        355                 360                 365
Met Leu Lys Leu Arg Ile Gln Ser Glu Lys Arg Asp Pro Ser Ser Ile
370                 375                 380
Glu Ile Ala Gly Gly Val Ile Ile Gln
385                 390
```

<210> SEQ ID NO 5
<211> LENGTH: 1114
<212> TYPE: PRT
<213> ORGANISM: Homo sapiens
<220> FEATURE:
<221> NAME/KEY: SIGNAL
<222> LOCATION: (1)..(28)
<220> FEATURE:
<221> NAME/KEY: VARSPLIC
<222> LOCATION: (1)..(1114)
<223> OTHER INFORMATION: alternatively spliced
<220> FEATURE:
<221> NAME/KEY: TRANSMEM
<222> LOCATION: (637)..(667)

<400> SEQUENCE: 5

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

```
Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
            405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
        450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
            565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
        610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
            645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
        690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
            725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
        770                 775                 780

Pro His Val Ile Lys Leu Tyr Gly Ala Cys Ser Gln Asp Gly Pro Leu
785                 790                 795                 800
```

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
        1010                1015                1020

Ser Asp Ser Leu Ile Tyr Asp Asp Gly Leu Ser Glu Glu Glu Thr
        1025                1030                1035

Pro Leu Val Asp Cys Asn Asn Ala Pro Leu Pro Arg Ala Leu Pro
        1040                1045                1050

Ser Thr Trp Ile Glu Asn Lys Leu Tyr Gly Met Ser Asp Pro Asn
        1055                1060                1065

Trp Pro Gly Glu Ser Pro Val Pro Leu Thr Arg Ala Asp Gly Thr
        1070                1075                1080

Asn Thr Gly Phe Pro Arg Tyr Pro Asn Asp Ser Val Tyr Ala Asn
        1085                1090                1095

Trp Met Leu Ser Pro Ser Ala Ala Lys Leu Met Asp Thr Phe Asp
        1100                1105                1110

Ser

<210> SEQ ID NO 6
<211> LENGTH: 577
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 signal sequence
<220> FEATURE:
<221> NAME/KEY: MISC_FEATURE
<222> LOCATION: (17)..(348)
<223> OTHER INFORMATION: hGFRAL extracellular region
<220> FEATURE:
<221> NAME/KEY: MISC_FEATURE
<222> LOCATION: (349)..(358)
<223> OTHER INFORMATION: GGGGSGGGGS linker
<220> FEATURE:
<221> NAME/KEY: MISC_FEATURE
<222> LOCATION: (359)..(577)
<223> OTHER INFORMATION: mouse Anti-TNP light chain

<400> SEQUENCE: 6

Met Pro Leu Leu Leu Leu Pro Leu Leu Trp Ala Gly Ala Leu Ala
1               5                   10                  15

Gln Thr Asn Asn Cys Thr Tyr Leu Arg Glu Gln Cys Leu Arg Asp Ala
            20                  25                  30

Asn Gly Cys Lys His Ala Trp Arg Val Met Glu Asp Ala Cys Asn Asp
        35                  40                  45

Ser Asp Pro Gly Asp Pro Cys Lys Met Arg Asn Ser Ser Tyr Cys Asn
    50                  55                  60

Leu Ser Ile Gln Tyr Leu Val Glu Ser Asn Phe Gln Phe Lys Glu Cys
65                  70                  75                  80

Leu Cys Thr Asp Asp Phe Tyr Cys Thr Val Asn Lys Leu Leu Gly Lys
                85                  90                  95

Lys Cys Ile Asn Lys Ser Asp Asn Val Lys Glu Asp Lys Phe Lys Trp
            100                 105                 110

Asn Leu Thr Thr Arg Ser His His Gly Phe Lys Gly Met Trp Ser Cys
        115                 120                 125

Leu Glu Val Ala Glu Ala Cys Val Gly Asp Val Val Cys Asn Ala Gln
    130                 135                 140

Leu Ala Ser Tyr Leu Lys Ala Cys Ser Ala Asn Gly Asn Pro Cys Asp
145                 150                 155                 160

Leu Lys Gln Cys Gln Ala Ala Ile Arg Phe Phe Tyr Gln Asn Ile Pro
                165                 170                 175

Phe Asn Ile Ala Gln Met Leu Ala Phe Cys Asp Cys Ala Gln Ser Asp
            180                 185                 190

Ile Pro Cys Gln Gln Ser Lys Glu Ala Leu His Ser Lys Thr Cys Ala
        195                 200                 205

Val Asn Met Val Pro Pro Thr Cys Leu Ser Val Ile Arg Ser Cys
    210                 215                 220

Gln Asn Asp Glu Leu Cys Arg Arg His Tyr Arg Thr Phe Gln Ser Lys
225                 230                 235                 240

Cys Trp Gln Arg Val Thr Arg Lys Cys His Glu Asp Glu Asn Cys Ile
                245                 250                 255

Ser Thr Leu Ser Lys Gln Asp Leu Thr Cys Ser Gly Ser Asp Asp Cys
            260                 265                 270

Lys Ala Ala Tyr Ile Asp Ile Leu Gly Thr Val Leu Gln Val Gln Cys
        275                 280                 285

Thr Cys Arg Thr Ile Thr Gln Ser Glu Glu Ser Leu Cys Lys Ile Phe
    290                 295                 300

Gln His Met Leu His Arg Lys Ser Cys Phe Asn Tyr Pro Thr Leu Ser
305                 310                 315                 320

Asn Val Lys Gly Met Ala Leu Tyr Thr Arg Lys His Ala Asn Lys Ile
                325                 330                 335

Thr Leu Thr Gly Phe His Ser Pro Phe Asn Gly Glu Gly Gly Gly Gly
            340                 345                 350

Ser Gly Gly Gly Gly Ser Asp Val Val Met Thr Gln Thr Pro Leu Ser
        355                 360                 365

Leu Pro Val Ser Leu Gly Asp Gln Ala Ser Ile Ser Cys Arg Ser Ser

-continued

```
                370                 375                 380
Gln Ser Leu Leu His Ser Asn Gly Asn Thr Tyr Leu His Trp Tyr Leu
385                 390                 395                 400

Gln Lys Pro Gly Gln Ser Pro Lys Leu Leu Ile Tyr Lys Val Ser Asn
                405                 410                 415

Arg Phe Ser Gly Val Pro Asp Arg Phe Ser Gly Ser Gly Ser Gly Thr
                420                 425                 430

Asp Phe Thr Leu Lys Ile Ser Arg Val Glu Ala Glu Asp Leu Gly Val
                435                 440                 445

Tyr Phe Cys Ser Gln Ser Thr His Val Pro Trp Thr Phe Gly Gly Gly
                450                 455                 460

Thr Lys Leu Glu Ile Lys Arg Ala Asp Ala Ala Pro Thr Val Ser Ile
465                 470                 475                 480

Phe Pro Pro Ser Ser Glu Gln Leu Thr Ser Gly Gly Ala Ser Val Val
                485                 490                 495

Cys Phe Leu Asn Asn Phe Tyr Pro Lys Asp Ile Asn Val Lys Trp Lys
                500                 505                 510

Ile Asp Gly Ser Glu Arg Gln Asn Gly Val Leu Asn Ser Trp Thr Asp
                515                 520                 525

Gln Asp Ser Lys Asp Ser Thr Tyr Ser Met Ser Ser Thr Leu Thr Leu
                530                 535                 540

Thr Lys Asp Glu Tyr Glu Arg His Asn Ser Tyr Thr Cys Glu Ala Thr
545                 550                 555                 560

His Lys Thr Ser Thr Ser Pro Ile Val Lys Ser Phe Asn Arg Asn Glu
                565                 570                 575

Cys
```

<210> SEQ ID NO 7
<211> LENGTH: 575
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 Signal sequence
<220> FEATURE:
<221> NAME/KEY: MISC_FEATURE
<222> LOCATION: (17)..(340)
<223> OTHER INFORMATION: hGFRAL extracellular region
<220> FEATURE:
<221> NAME/KEY: MISC_FEATURE
<222> LOCATION: (341)..(575)
<223> OTHER INFORMATION: hIgG1.1_Fc

<400> SEQUENCE: 7

```
Met Pro Leu Leu Leu Leu Pro Leu Leu Trp Ala Gly Ala Leu Ala
1               5                   10                  15

Gln Thr Asn Asn Cys Thr Tyr Leu Arg Glu Gln Cys Leu Arg Asp Ala
                20                  25                  30

Asn Gly Cys Lys His Ala Trp Arg Val Met Glu Asp Ala Cys Asn Asp
                35                  40                  45

Ser Asp Pro Gly Asp Pro Cys Lys Met Arg Asn Ser Tyr Cys Asn
50                  55                  60

Leu Ser Ile Gln Tyr Leu Val Glu Ser Asn Phe Gln Phe Lys Glu Cys
65                  70                  75                  80

Leu Cys Thr Asp Asp Phe Tyr Cys Thr Val Asn Lys Leu Leu Gly Lys
                85                  90                  95
```

```
Lys Cys Ile Asn Lys Ser Asp Asn Val Lys Glu Asp Lys Phe Lys Trp
            100                 105                 110

Asn Leu Thr Thr Arg Ser His His Gly Phe Lys Gly Met Trp Ser Cys
            115                 120                 125

Leu Glu Val Ala Glu Ala Cys Val Gly Asp Val Val Cys Asn Ala Gln
            130                 135                 140

Leu Ala Ser Tyr Leu Lys Ala Cys Ser Ala Asn Gly Asn Pro Cys Asp
145                 150                 155                 160

Leu Lys Gln Cys Gln Ala Ala Ile Arg Phe Phe Tyr Gln Asn Ile Pro
                165                 170                 175

Phe Asn Ile Ala Gln Met Leu Ala Phe Cys Asp Cys Ala Gln Ser Asp
                180                 185                 190

Ile Pro Cys Gln Gln Ser Lys Glu Ala Leu His Ser Lys Thr Cys Ala
                195                 200                 205

Val Asn Met Val Pro Pro Thr Cys Leu Ser Val Ile Arg Ser Cys
210                 215                 220

Gln Asn Asp Glu Leu Cys Arg Arg His Tyr Arg Thr Phe Gln Ser Lys
225                 230                 235                 240

Cys Trp Gln Arg Val Thr Arg Lys Cys His Glu Asp Glu Asn Cys Ile
                245                 250                 255

Ser Thr Leu Ser Lys Gln Asp Leu Thr Cys Ser Gly Ser Asp Asp Cys
                260                 265                 270

Lys Ala Ala Tyr Ile Asp Ile Leu Gly Thr Val Leu Gln Val Gln Cys
                275                 280                 285

Thr Cys Arg Thr Ile Thr Gln Ser Glu Glu Ser Leu Cys Lys Ile Phe
                290                 295                 300

Gln His Met Leu His Arg Lys Ser Cys Phe Asn Tyr Pro Thr Leu Ser
305                 310                 315                 320

Asn Val Lys Gly Met Ala Leu Tyr Thr Arg Lys His Ala Asn Lys Ile
                325                 330                 335

Thr Leu Thr Gly Phe His Ser Pro Phe Asn Gly Glu Asp Lys Thr His
                340                 345                 350

Thr Cys Pro Pro Cys Pro Ala Pro Glu Ala Glu Gly Ala Pro Ser Val
                355                 360                 365

Phe Leu Phe Pro Pro Lys Pro Lys Asp Thr Leu Met Ile Ser Arg Thr
370                 375                 380

Pro Glu Val Thr Cys Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
                420                 425                 430

Val Leu Thr Val Leu His Gln Asp Trp Leu Asn Gly Lys Glu Tyr Lys
                435                 440                 445

Cys Lys Val Ser Asn Lys Ala Leu Pro Ser Ser Ile Glu Lys Thr Ile
                450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510
```

-continued

```
Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 8
<211> LENGTH: 574
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 signal sequence
<220> FEATURE:
<221> NAME/KEY: MISC_FEATURE
<222> LOCATION: (17)..(345)
<223> OTHER INFORMATION: mGFRAL extracellular region
<220> FEATURE:
<221> NAME/KEY: MISC_FEATURE
<222> LOCATION: (346)..(355)
<223> OTHER INFORMATION: GGGGSGGGGS linker
<220> FEATURE:
<221> NAME/KEY: MISC_FEATURE
<222> LOCATION: (357)..(575)
<223> OTHER INFORMATION: mouse Anti-TNP light chain

<400> SEQUENCE: 8

Met Pro Leu Leu Leu Leu Pro Leu Leu Trp Ala Gly Ala Leu Ala
1               5                   10                  15

Gln Thr Asn Asp Cys Ala His Leu Ile Gln Lys Cys Leu Ile Asp Ala
                20                  25                  30

Asn Gly Cys Glu Gln Ser Trp Arg Ser Met Glu Asp Thr Cys Leu Thr
            35                  40                  45

Pro Gly Asp Ser Cys Lys Ile Asn Asn Ser Leu His Cys Asn Leu Ser
50                  55                  60

Ile Gln Ala Leu Val Glu Lys Asn Phe Gln Phe Lys Glu Cys Leu Cys
65                  70                  75                  80

Met Asp Asp Leu His Cys Thr Val Asn Lys Leu Phe Gly Lys Lys Cys
                85                  90                  95

Thr Asn Lys Thr Asp Asn Met Glu Lys Asp Asn Lys Asp Lys Trp Asn
            100                 105                 110

Leu Thr Thr Thr Pro Phe Tyr His Gly Phe Lys Gln Met Gln Ser Cys
        115                 120                 125

Leu Glu Val Thr Glu Ala Cys Val Gly Asp Val Val Cys Asn Ala Gln
    130                 135                 140

Leu Ala Leu Tyr Leu Lys Ala Cys Ser Ala Asn Gly Asn Leu Cys Asp
145                 150                 155                 160

Val Lys His Cys Gln Ala Ala Ile Arg Phe Phe Tyr Gln Asn Met Pro
                165                 170                 175

Phe Asn Thr Ala Gln Met Leu Ala Phe Cys Asp Cys Ala Gln Ser Asp
            180                 185                 190

Ile Pro Cys Gln Gln Ser Lys Glu Thr Leu His Ser Lys Pro Cys Ala
        195                 200                 205

Leu Asn Ile Val Pro Pro Thr Cys Leu Ser Val Ile His Thr Cys
    210                 215                 220
```

-continued

```
Arg Asn Asp Glu Leu Cys Arg Thr His Tyr Arg Thr Phe Gln Thr Glu
225                 230                 235                 240

Cys Trp Pro His Ile Thr Gly Lys Cys His Glu Asp Glu Thr Cys Ile
            245                 250                 255

Ser Met Leu Gly Lys Gln Asp Leu Thr Cys Ser Gly Ser Glu Ser Cys
        260                 265                 270

Arg Ala Ala Phe Leu Gly Thr Phe Gly Thr Val Leu Gln Val Pro Cys
    275                 280                 285

Ala Cys Arg Gly Val Thr Gln Ala Glu Glu His Val Cys Met Ile Phe
290                 295                 300

Gln His Met Leu His Ser Lys Ser Cys Phe Asn Tyr Pro Thr Pro Asn
305                 310                 315                 320

Val Lys Asp Ile Ser Ser Tyr Glu Lys Lys Asn Ser Lys Glu Ile Thr
                325                 330                 335

Leu Thr Gly Phe Asn Ser Phe Phe Asn Gly Gly Gly Ser Gly Gly Gly
            340                 345                 350

Gly Gly Ser Asp Val Val Met Thr Gln Thr Pro Leu Ser Leu Pro Val
        355                 360                 365

Ser Leu Gly Asp Gln Ala Ser Ile Ser Cys Arg Ser Ser Gln Ser Leu
370                 375                 380

Leu His Ser Asn Gly Asn Thr Tyr Leu His Trp Tyr Leu Gln Lys Pro
385                 390                 395                 400

Gly Gln Ser Pro Lys Leu Leu Ile Tyr Lys Val Ser Asn Arg Phe Ser
                405                 410                 415

Gly Val Pro Asp Arg Phe Ser Gly Ser Gly Ser Gly Thr Asp Phe Thr
            420                 425                 430

Leu Lys Ile Ser Arg Val Glu Ala Glu Asp Leu Gly Val Tyr Phe Cys
        435                 440                 445

Ser Gln Ser Thr His Val Pro Trp Thr Phe Gly Gly Gly Thr Lys Leu
450                 455                 460

Glu Ile Lys Arg Ala Asp Ala Ala Pro Thr Val Ser Ile Phe Pro Pro
465                 470                 475                 480

Ser Ser Glu Gln Leu Thr Ser Gly Gly Ala Ser Val Val Cys Phe Leu
                485                 490                 495

Asn Asn Phe Tyr Pro Lys Asp Ile Asn Val Lys Trp Lys Ile Asp Gly
            500                 505                 510

Ser Glu Arg Gln Asn Gly Val Leu Asn Ser Trp Thr Asp Gln Asp Ser
        515                 520                 525

Lys Asp Ser Thr Tyr Ser Met Ser Ser Thr Leu Thr Leu Thr Lys Asp
530                 535                 540

Glu Tyr Glu Arg His Asn Ser Tyr Thr Cys Glu Ala Thr His Lys Thr
545                 550                 555                 560

Ser Thr Ser Pro Ile Val Lys Ser Phe Asn Arg Asn Glu Cys
                565                 570
```

```
<210> SEQ ID NO 9
<211> LENGTH: 356
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 Signal sequence
<220> FEATURE:
```

```
<221> NAME/KEY: MISC_FEATURE
<222> LOCATION: (17)..(127)
<223> OTHER INFORMATION: hGFRAL extracellular C1 domain
<220> FEATURE:
<221> NAME/KEY: MISC_FEATURE
<222> LOCATION: (128)..(137)
<223> OTHER INFORMATION: GGGGSGGGGS linker
<220> FEATURE:
<221> NAME/KEY: MISC_FEATURE
<222> LOCATION: (138)..(356)
<223> OTHER INFORMATION: mouse Anti-TNP light chain

<400> SEQUENCE: 9
```

| Met | Pro | Leu | Leu | Leu | Leu | Pro | Leu | Leu | Trp | Ala | Gly | Ala | Leu | Ala |
|---|---|---|---|---|---|---|---|---|---|---|---|---|---|---|
| 1 | | | | 5 | | | | | 10 | | | | | 15 |

| Gln | Thr | Asn | Asn | Cys | Thr | Tyr | Leu | Arg | Glu | Gln | Cys | Leu | Arg | Asp | Ala |
|---|---|---|---|---|---|---|---|---|---|---|---|---|---|---|---|
| | | | 20 | | | | | 25 | | | | | 30 | | |

Asn Gly Cys Lys His Ala Trp Arg Val Met Glu Asp Ala Cys Asn Asp
              35                  40                  45

Ser Asp Pro Gly Asp Pro Cys Lys Met Arg Asn Ser Ser Tyr Cys Asn
 50                  55                  60

Leu Ser Ile Gln Tyr Leu Val Glu Ser Asn Phe Gln Phe Lys Glu Cys
 65                  70                  75                  80

Leu Cys Thr Asp Asp Phe Tyr Cys Thr Val Asn Lys Leu Leu Gly Lys
                 85                  90                  95

Lys Cys Ile Asn Lys Ser Asp Asn Val Lys Glu Asp Lys Phe Lys Trp
                100                 105                 110

Asn Leu Thr Thr Arg Ser His His Gly Phe Lys Gly Met Trp Ser Gly
             115                 120                 125

Gly Gly Gly Ser Gly Gly Gly Gly Ser Asp Val Val Met Thr Gln Thr
         130                 135                 140

Pro Leu Ser Leu Pro Val Ser Leu Gly Asp Gln Ala Ser Ile Ser Cys
145                 150                 155                 160

Arg Ser Ser Gln Ser Leu Leu His Ser Asn Gly Asn Thr Tyr Leu His
                165                 170                 175

Trp Tyr Leu Gln Lys Pro Gly Gln Ser Pro Lys Leu Leu Ile Tyr Lys
                180                 185                 190

Val Ser Asn Arg Phe Ser Gly Val Pro Asp Arg Phe Ser Gly Ser Gly
            195                 200                 205

Ser Gly Thr Asp Phe Thr Leu Lys Ile Ser Arg Val Glu Ala Glu Asp
        210                 215                 220

Leu Gly Val Tyr Phe Cys Ser Gln Ser Thr His Val Pro Trp Thr Phe
225                 230                 235                 240

Gly Gly Gly Thr Lys Leu Glu Ile Lys Arg Ala Asp Ala Ala Pro Thr
                245                 250                 255

Val Ser Ile Phe Pro Pro Ser Ser Glu Gln Leu Thr Ser Gly Gly Ala
                260                 265                 270

Ser Val Val Cys Phe Leu Asn Asn Phe Tyr Pro Lys Asp Ile Asn Val
            275                 280                 285

Lys Trp Lys Ile Asp Gly Ser Glu Arg Gln Asn Gly Val Leu Asn Ser
        290                 295                 300

Trp Thr Asp Gln Asp Ser Lys Asp Ser Thr Tyr Ser Met Ser Ser Thr
305                 310                 315                 320

Leu Thr Leu Thr Lys Asp Glu Tyr Glu Arg His Asn Ser Tyr Thr Cys
                325                 330                 335

Glu Ala Thr His Lys Thr Ser Ser Pro Ile Val Lys Ser Phe Asn
                340                 345                 350

Arg Asn Glu Cys
        355

<210> SEQ ID NO 10
<211> LENGTH: 334
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 Signal sequence
<220> FEATURE:
<221> NAME/KEY: MISC_FEATURE
<222> LOCATION: (17)..(105)
<223> OTHER INFORMATION: hGFRAL extracellular C2 domain
<220> FEATURE:
<221> NAME/KEY: MISC_FEATURE
<222> LOCATION: (106)..(115)
<223> OTHER INFORMATION: GGGGSGGGGS linker
<220> FEATURE:
<221> NAME/KEY: MISC_FEATURE
<222> LOCATION: (116)..(334)
<223> OTHER INFORMATION: mouse Anti-TNP light chain

<400> SEQUENCE: 10

Met Pro Leu Leu Leu Leu Pro Leu Leu Trp Ala Gly Ala Leu Ala
1               5                   10                  15

Cys Leu Glu Val Ala Glu Ala Cys Val Gly Asp Val Cys Asn Ala
                20                  25                  30

Gln Leu Ala Ser Tyr Leu Lys Ala Cys Ser Ala Asn Gly Asn Pro Cys
                35                  40                  45

Asp Leu Lys Gln Cys Gln Ala Ala Ile Arg Phe Phe Tyr Gln Asn Ile
        50                  55                  60

Pro Phe Asn Ile Ala Gln Met Leu Ala Phe Cys Asp Cys Ala Gln Ser
65                  70                  75                  80

Asp Ile Pro Cys Gln Gln Ser Lys Glu Ala Leu His Ser Lys Thr Cys
                85                  90                  95

Ala Val Asn Met Val Pro Pro Thr Gly Gly Gly Gly Ser Gly Gly
                100                 105                 110

Gly Gly Ser Asp Val Val Met Thr Gln Thr Pro Leu Ser Leu Pro Val
        115                 120                 125

Ser Leu Gly Asp Gln Ala Ser Ile Ser Cys Arg Ser Ser Gln Ser Leu
130                 135                 140

Leu His Ser Asn Gly Asn Thr Tyr Leu His Trp Tyr Leu Gln Lys Pro
145                 150                 155                 160

Gly Gln Ser Pro Lys Leu Leu Ile Tyr Lys Val Ser Asn Arg Phe Ser
                165                 170                 175

Gly Val Pro Asp Arg Phe Ser Gly Ser Gly Ser Gly Thr Asp Phe Thr
            180                 185                 190

Leu Lys Ile Ser Arg Val Glu Ala Glu Asp Leu Gly Val Tyr Phe Cys
        195                 200                 205

Ser Gln Ser Thr His Val Pro Trp Thr Phe Gly Gly Gly Thr Lys Leu
    210                 215                 220

Glu Ile Lys Arg Ala Asp Ala Ala Pro Thr Val Ser Ile Phe Pro Pro
225                 230                 235                 240

Ser Ser Glu Gln Leu Thr Ser Gly Gly Ala Ser Val Val Cys Phe Leu
                245                 250                 255

Asn Asn Phe Tyr Pro Lys Asp Ile Asn Val Lys Trp Lys Ile Asp Gly

```
                260                 265                 270
Ser Glu Arg Gln Asn Gly Val Leu Asn Ser Trp Thr Asp Gln Asp Ser
            275                 280                 285

Lys Asp Ser Thr Tyr Ser Met Ser Ser Thr Leu Thr Leu Thr Lys Asp
            290                 295                 300

Glu Tyr Glu Arg His Asn Ser Tyr Thr Cys Glu Ala Thr His Lys Thr
305                 310                 315                 320

Ser Thr Ser Pro Ile Val Lys Ser Phe Asn Arg Asn Glu Cys
                325                 330

<210> SEQ ID NO 11
<211> LENGTH: 377
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 Signal sequence
<220> FEATURE:
<221> NAME/KEY: MISC_FEATURE
<222> LOCATION: (17)..(148)
<223> OTHER INFORMATION: hGFRAL extracellular C3 domain
<220> FEATURE:
<221> NAME/KEY: MISC_FEATURE
<222> LOCATION: (149)..(158)
<223> OTHER INFORMATION: GGGGSGGGGS linker
<220> FEATURE:
<221> NAME/KEY: MISC_FEATURE
<222> LOCATION: (159)..(377)
<223> OTHER INFORMATION: mouse Anti-TNP light chain

<400> SEQUENCE: 11

Met Pro Leu Leu Leu Leu Leu Pro Leu Leu Trp Ala Gly Ala Leu Ala
1               5                   10                  15

Cys Leu Ser Val Ile Arg Ser Cys Gln Asn Asp Glu Leu Cys Arg Arg
            20                  25                  30

His Tyr Arg Thr Phe Gln Ser Lys Cys Trp Gln Arg Val Thr Arg Lys
        35                  40                  45

Cys His Glu Asp Glu Asn Cys Ile Ser Thr Leu Ser Lys Gln Asp Leu
    50                  55                  60

Thr Cys Ser Gly Ser Asp Asp Cys Lys Ala Ala Tyr Ile Asp Ile Leu
65                  70                  75                  80

Gly Thr Val Leu Gln Val Gln Cys Thr Cys Arg Thr Ile Thr Gln Ser
                85                  90                  95

Glu Glu Ser Leu Cys Lys Ile Phe Gln His Met Leu His Arg Lys Ser
            100                 105                 110

Cys Phe Asn Tyr Pro Thr Leu Ser Asn Val Lys Gly Met Ala Leu Tyr
        115                 120                 125

Thr Arg Lys His Ala Asn Lys Ile Thr Leu Thr Gly Phe His Ser Pro
    130                 135                 140

Phe Asn Gly Glu Gly Gly Gly Gly Ser Gly Gly Gly Gly Ser Asp Val
145                 150                 155                 160

Val Met Thr Gln Thr Pro Leu Ser Leu Pro Val Ser Leu Gly Asp Gln
                165                 170                 175

Ala Ser Ile Ser Cys Arg Ser Ser Gln Ser Leu Leu His Ser Asn Gly
            180                 185                 190

Asn Thr Tyr Leu His Trp Tyr Leu Gln Lys Pro Gly Gln Ser Pro Lys
        195                 200                 205
```

```
Leu Leu Ile Tyr Lys Val Ser Asn Arg Phe Ser Gly Val Pro Asp Arg
210                 215                 220

Phe Ser Gly Ser Gly Ser Gly Thr Asp Phe Thr Leu Lys Ile Ser Arg
225                 230                 235                 240

Val Glu Ala Glu Asp Leu Gly Val Tyr Phe Cys Ser Gln Ser Thr His
                245                 250                 255

Val Pro Trp Thr Phe Gly Gly Gly Thr Lys Leu Glu Ile Lys Arg Ala
            260                 265                 270

Asp Ala Ala Pro Thr Val Ser Ile Phe Pro Pro Ser Glu Gln Leu
                275                 280                 285

Thr Ser Gly Gly Ala Ser Val Val Cys Phe Leu Asn Asn Phe Tyr Pro
290                 295                 300

Lys Asp Ile Asn Val Lys Trp Lys Ile Asp Gly Ser Glu Arg Gln Asn
305                 310                 315                 320

Gly Val Leu Asn Ser Trp Thr Asp Gln Asp Ser Lys Asp Ser Thr Tyr
                325                 330                 335

Ser Met Ser Ser Thr Leu Thr Leu Thr Lys Asp Glu Tyr Glu Arg His
            340                 345                 350

Asn Ser Tyr Thr Cys Glu Ala Thr His Lys Thr Ser Thr Ser Pro Ile
                355                 360                 365

Val Lys Ser Phe Asn Arg Asn Glu Cys
370                 375

<210> SEQ ID NO 12
<211> LENGTH: 445
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 Signal sequence
<220> FEATURE:
<221> NAME/KEY: MISC_FEATURE
<222> LOCATION: (17)..(216)
<223> OTHER INFORMATION: hGFRAL extracellular C1 and C2 domains
<220> FEATURE:
<221> NAME/KEY: MISC_FEATURE
<222> LOCATION: (217)..(226)
<223> OTHER INFORMATION: GGGGSGGGGS linker
<220> FEATURE:
<221> NAME/KEY: MISC_FEATURE
<222> LOCATION: (227)..(445)
<223> OTHER INFORMATION: mouse Anti-TNP light chain

<400> SEQUENCE: 12

Met Pro Leu Leu Leu Leu Pro Leu Leu Trp Ala Gly Ala Leu Ala
1               5                   10                  15

Gln Thr Asn Asn Cys Thr Tyr Leu Arg Glu Gln Cys Leu Arg Asp Ala
                20                  25                  30

Asn Gly Cys Lys His Ala Trp Arg Val Met Glu Asp Ala Cys Asn Asp
            35                  40                  45

Ser Asp Pro Gly Asp Pro Cys Lys Met Arg Asn Ser Ser Tyr Cys Asn
50                  55                  60

Leu Ser Ile Gln Tyr Leu Val Glu Ser Asn Phe Gln Phe Lys Glu Cys
65                  70                  75                  80

Leu Cys Thr Asp Asp Phe Tyr Cys Thr Val Asn Lys Leu Leu Gly Lys
                85                  90                  95

Lys Cys Ile Asn Lys Ser Asp Asn Val Lys Glu Asp Lys Phe Lys Trp
            100                 105                 110
```

```
Asn Leu Thr Thr Arg Ser His His Gly Phe Lys Gly Met Trp Ser Cys
        115                 120                 125

Leu Glu Val Ala Glu Ala Cys Val Gly Asp Val Val Cys Asn Ala Gln
    130                 135                 140

Leu Ala Ser Tyr Leu Lys Ala Cys Ser Ala Asn Gly Asn Pro Cys Asp
145                 150                 155                 160

Leu Lys Gln Cys Gln Ala Ala Ile Arg Phe Phe Tyr Gln Asn Ile Pro
                165                 170                 175

Phe Asn Ile Ala Gln Met Leu Ala Phe Cys Asp Cys Ala Gln Ser Asp
            180                 185                 190

Ile Pro Cys Gln Gln Ser Lys Glu Ala Leu His Ser Lys Thr Cys Ala
        195                 200                 205

Val Asn Met Val Pro Pro Thr Gly Gly Gly Ser Gly Gly Gly
    210                 215                 220

Gly Ser Asp Val Val Met Thr Gln Thr Pro Leu Ser Leu Pro Val Ser
225                 230                 235                 240

Leu Gly Asp Gln Ala Ser Ile Ser Cys Arg Ser Ser Gln Ser Leu Leu
                245                 250                 255

His Ser Asn Gly Asn Thr Tyr Leu His Trp Tyr Leu Gln Lys Pro Gly
            260                 265                 270

Gln Ser Pro Lys Leu Leu Ile Tyr Lys Val Ser Asn Arg Phe Ser Gly
        275                 280                 285

Val Pro Asp Arg Phe Ser Gly Ser Gly Ser Gly Thr Asp Phe Thr Leu
    290                 295                 300

Lys Ile Ser Arg Val Glu Ala Glu Asp Leu Gly Val Tyr Phe Cys Ser
305                 310                 315                 320

Gln Ser Thr His Val Pro Trp Thr Phe Gly Gly Gly Thr Lys Leu Glu
                325                 330                 335

Ile Lys Arg Ala Asp Ala Ala Pro Thr Val Ser Ile Phe Pro Pro Ser
            340                 345                 350

Ser Glu Gln Leu Thr Ser Gly Gly Ala Ser Val Val Cys Phe Leu Asn
        355                 360                 365

Asn Phe Tyr Pro Lys Asp Ile Asn Val Lys Trp Lys Ile Asp Gly Ser
    370                 375                 380

Glu Arg Gln Asn Gly Val Leu Asn Ser Trp Thr Asp Gln Asp Ser Lys
385                 390                 395                 400

Asp Ser Thr Tyr Ser Met Ser Ser Thr Leu Thr Leu Thr Lys Asp Glu
                405                 410                 415

Tyr Glu Arg His Asn Ser Tyr Thr Cys Glu Ala Thr His Lys Thr Ser
            420                 425                 430

Thr Ser Pro Ile Val Lys Ser Phe Asn Arg Asn Glu Cys
        435                 440                 445

<210> SEQ ID NO 13
<211> LENGTH: 466
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(16)
<223> OTHER INFORMATION: CD33 Signal sequence
<220> FEATURE:
<221> NAME/KEY: MISC_FEATURE
<222> LOCATION: (17)..(237)
<223> OTHER INFORMATION: hGFRAL extracellular C2 and C3 domains
```

<220> FEATURE:
<221> NAME/KEY: MISC_FEATURE
<222> LOCATION: (238)..(247)
<223> OTHER INFORMATION: GGGGSGGGGS linker
<220> FEATURE:
<221> NAME/KEY: MISC_FEATURE
<222> LOCATION: (248)..(466)
<223> OTHER INFORMATION: mouse Anti-TNP light chain

<400> SEQUENCE: 13

```
Met Pro Leu Leu Leu Leu Pro Leu Leu Trp Ala Gly Ala Leu Ala
1               5                   10                  15

Cys Leu Glu Val Ala Glu Ala Cys Val Gly Asp Val Val Cys Asn Ala
            20                  25                  30

Gln Leu Ala Ser Tyr Leu Lys Ala Cys Ser Ala Asn Gly Asn Pro Cys
            35                  40                  45

Asp Leu Lys Gln Cys Gln Ala Ala Ile Arg Phe Phe Tyr Gln Asn Ile
        50                  55                  60

Pro Phe Asn Ile Ala Gln Met Leu Ala Phe Cys Asp Cys Ala Gln Ser
65                  70                  75                  80

Asp Ile Pro Cys Gln Gln Ser Lys Glu Ala Leu His Ser Lys Thr Cys
                85                  90                  95

Ala Val Asn Met Val Pro Pro Thr Cys Leu Ser Val Ile Arg Ser
            100                 105                 110

Cys Gln Asn Asp Glu Leu Cys Arg Arg His Tyr Arg Thr Phe Gln Ser
            115                 120                 125

Lys Cys Trp Gln Arg Val Thr Arg Lys Cys His Glu Asp Glu Asn Cys
        130                 135                 140

Ile Ser Thr Leu Ser Lys Gln Asp Leu Thr Cys Ser Gly Ser Asp Asp
145                 150                 155                 160

Cys Lys Ala Ala Tyr Ile Asp Ile Leu Gly Thr Val Leu Gln Val Gln
                165                 170                 175

Cys Thr Cys Arg Thr Ile Thr Gln Ser Glu Glu Ser Leu Cys Lys Ile
            180                 185                 190

Phe Gln His Met Leu His Arg Lys Ser Cys Phe Asn Tyr Pro Thr Leu
            195                 200                 205

Ser Asn Val Lys Gly Met Ala Leu Tyr Thr Arg Lys His Ala Asn Lys
        210                 215                 220

Ile Thr Leu Thr Gly Phe His Ser Pro Phe Asn Gly Glu Gly Gly Gly
225                 230                 235                 240

Gly Ser Gly Gly Gly Gly Ser Asp Val Val Met Thr Gln Thr Pro Leu
                245                 250                 255

Ser Leu Pro Val Ser Leu Gly Asp Gln Ala Ser Ile Ser Cys Arg Ser
            260                 265                 270

Ser Gln Ser Leu Leu His Ser Asn Gly Asn Thr Tyr Leu His Trp Tyr
            275                 280                 285

Leu Gln Lys Pro Gly Gln Ser Pro Lys Leu Leu Ile Tyr Lys Val Ser
        290                 295                 300

Asn Arg Phe Ser Gly Val Pro Asp Arg Phe Ser Gly Ser Gly Ser Gly
305                 310                 315                 320

Thr Asp Phe Thr Leu Lys Ile Ser Arg Val Glu Ala Glu Asp Leu Gly
                325                 330                 335

Val Tyr Phe Cys Ser Gln Ser Thr His Val Pro Trp Thr Phe Gly Gly
            340                 345                 350

Gly Thr Lys Leu Glu Ile Lys Arg Ala Asp Ala Ala Pro Thr Val Ser
        355                 360                 365
```

-continued

```
Ile Phe Pro Pro Ser Ser Glu Gln Leu Thr Ser Gly Gly Ala Ser Val
    370                 375                 380

Val Cys Phe Leu Asn Asn Phe Tyr Pro Lys Asp Ile Asn Val Lys Trp
385                 390                 395                 400

Lys Ile Asp Gly Ser Glu Arg Gln Asn Gly Val Leu Asn Ser Trp Thr
                405                 410                 415

Asp Gln Asp Ser Lys Asp Ser Thr Tyr Ser Met Ser Ser Thr Leu Thr
            420                 425                 430

Leu Thr Lys Asp Glu Tyr Glu Arg His Asn Ser Tyr Thr Cys Glu Ala
        435                 440                 445

Thr His Lys Thr Ser Thr Ser Pro Ile Val Lys Ser Phe Asn Arg Asn
    450                 455                 460

Glu Cys
465

<210> SEQ ID NO 14
<211> LENGTH: 285
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(18)
<223> OTHER INFORMATION: signal sequence of mouse Ig heavy chain
<220> FEATURE:
<221> NAME/KEY: MISC_FEATURE
<222> LOCATION: (19)..(236)
<223> OTHER INFORMATION: mouse Anti-TNP fab heavy chain
<220> FEATURE:
<221> NAME/KEY: MISC_FEATURE
<222> LOCATION: (237)..(285)
<223> OTHER INFORMATION: human PDGFRB gene region containing the TM
<220> FEATURE:
<221> NAME/KEY: MISC_FEATURE
<222> LOCATION: (257)..(277)
<223> OTHER INFORMATION: human PDGFRB Transmembrane

<400> SEQUENCE: 14

Met Met Val Leu Ser Leu Leu Tyr Leu Leu Thr Ala Leu Pro Gly Ile
1               5                   10                  15

Leu Ser Glu Val Gln Ile Gln Glu Ser Gly Pro Ser Leu Val Lys Pro
            20                  25                  30

Ser Gln Thr Leu Ser Leu Thr Cys Ser Val Ser Gly Asp Ser Ile Thr
        35                  40                  45

Ser Gly Tyr Trp Asn Trp Ile Arg Lys Phe Pro Gly His Lys Ile Glu
    50                  55                  60

Tyr Met Gly Thr Ile Ser Tyr Ser Gly Asp Thr Tyr Tyr Asn Pro Ser
65                  70                  75                  80

Leu Lys Ser Arg Ile Ser Ile Thr Arg Asp Thr Ser Lys Asn Gln Tyr
                85                  90                  95

Tyr Leu His Leu Asn Ser Val Thr Thr Glu Asp Thr Ala Thr Tyr Tyr
            100                 105                 110

Cys Ala Arg Tyr Gly Ser Tyr Val Phe Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
```

```
            165                 170                 175
Ser Gly Ser Leu Ser Gly Val His Thr Phe Pro Ala Val Leu Gln
        180                 185                 190

Ser Asp Leu Tyr Thr Leu Ser Ser Val Thr Val Pro Ser Ser Thr
        195                 200                 205

Trp Pro Ser Glu Thr Val Thr Cys Asn Val Ala His Pro Ala Ser Ser
210                 215                 220

Thr Lys Val Asp Lys Lys Ile Val Pro Arg Asp Cys Ala Val Gly Gln
225                 230                 235                 240

Asp Thr Gln Glu Val Ile Val Val Pro His Ser Leu Pro Phe Lys Val
            245                 250                 255

Val Val Ile Ser Ala Ile Leu Ala Leu Val Val Leu Thr Ile Ile Ser
            260                 265                 270

Leu Ile Ile Leu Ile Met Leu Trp Gln Lys Lys Pro Arg
            275                 280                 285

<210> SEQ ID NO 15
<211> LENGTH: 253
<212> TYPE: PRT
<213> ORGANISM: Artificial Sequence
<220> FEATURE:
<223> OTHER INFORMATION: Chimeric peptide
<220> FEATURE:
<221> NAME/KEY: MISC_FEATURE
<222> LOCATION: (1)..(18)
<223> OTHER INFORMATION: signal sequence of mouse Ig heavy chain
<220> FEATURE:
<221> NAME/KEY: MISC_FEATURE
<222> LOCATION: (19)..(236)
<223> OTHER INFORMATION: mouse Anti-TNP fab heavy chain
<220> FEATURE:
<221> NAME/KEY: MISC_FEATURE
<222> LOCATION: (237)..(241)
<223> OTHER INFORMATION: GGGGS linker
<220> FEATURE:
<221> NAME/KEY: MISC_FEATURE
<222> LOCATION: (242)..(253)
<223> OTHER INFORMATION: HPC4 tag

<400> SEQUENCE: 15

Met Met Val Leu Ser Leu Leu Tyr Leu Leu Thr Ala Leu Pro Gly Ile
1               5                   10                  15

Leu Ser Glu Val Gln Ile Gln Glu Ser Gly Pro Ser Leu Val Lys Pro
            20                  25                  30

Ser Gln Thr Leu Ser Leu Thr Cys Ser Val Ser Gly Asp Ser Ile Thr
        35                  40                  45

Ser Gly Tyr Trp Asn Trp Ile Arg Lys Phe Pro Gly His Lys Ile Glu
    50                  55                  60

Tyr Met Gly Thr Ile Ser Tyr Ser Gly Asp Thr Tyr Tyr Asn Pro Ser
65                  70                  75                  80

Leu Lys Ser Arg Ile Ser Ile Thr Arg Asp Thr Ser Lys Asn Gln Tyr
                85                  90                  95

Tyr Leu His Leu Asn Ser Val Thr Thr Glu Asp Thr Ala Thr Tyr Tyr
            100                 105                 110

Cys Ala Arg Tyr Gly Ser Tyr Val Phe Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160
```

```
Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Val Thr Val Pro Ser Ser Thr
            195                 200                 205

Trp Pro Ser Glu Thr Val Thr Cys Asn Val Ala His Pro Ala Ser Ser
    210                 215                 220

Thr Lys Val Asp Lys Lys Ile Val Pro Arg Asp Cys Gly Gly Gly
225                 230                 235                 240

Ser Glu Asp Gln Val Asp Pro Arg Leu Ile Asp Gly Lys
                245                 250
```

```
<210> SEQ ID NO 16
<211> LENGTH: 112
<212> TYPE: PRT
<213> ORGANISM: Homo sapiens
<220> FEATURE:
<221> NAME/KEY: DISULFID
<222> LOCATION: (7)..(14)
<220> FEATURE:
<221> NAME/KEY: DISULFID
<222> LOCATION: (15)..(78)
<220> FEATURE:
<221> NAME/KEY: DISULFID
<222> LOCATION: (44)..(109)
<220> FEATURE:
<221> NAME/KEY: DISULFID
<222> LOCATION: (48)..(111)
<220> FEATURE:
<221> NAME/KEY: DISULFID
<222> LOCATION: (77)..(77)

<400> SEQUENCE: 16

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

```
<210> SEQ ID NO 17
<211> LENGTH: 1105
<212> TYPE: PRT
<213> ORGANISM: Homo sapiens

<400> SEQUENCE: 17

Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45
```

-continued

```
Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
 65                  70                  75                  80

His Glu Asn Asn Trp Ile Cys Ile Gln Glu Asp Thr Gly Leu Leu Tyr
                 85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
```

```
            465                 470                 475                 480
Leu His Tyr Met Val Ala Thr Asp Gln Gln Thr Ser Arg Gln Ala
                485                 490                 495
Gln Ala Gln Leu Leu Val Thr Val Glu Gly Ser Tyr Val Ala Glu Glu
            500                 505                 510
Ala Gly Cys Pro Leu Ser Cys Ala Val Ser Lys Arg Arg Leu Glu Cys
            515                 520                 525
Glu Glu Cys Gly Gly Leu Gly Ser Pro Thr Gly Arg Cys Glu Trp Arg
            530                 535                 540
Gln Gly Asp Gly Lys Gly Ile Thr Arg Asn Phe Ser Thr Cys Ser Pro
545                 550                 555                 560
Ser Thr Lys Thr Cys Pro Asp Gly His Cys Asp Val Val Glu Thr Gln
                565                 570                 575
Asp Ile Asn Ile Cys Pro Gln Asp Cys Leu Arg Gly Ser Ile Val Gly
                580                 585                 590
Gly His Glu Pro Gly Glu Pro Arg Gly Ile Lys Ala Gly Tyr Gly Thr
            595                 600                 605
Cys Asn Cys Phe Pro Glu Glu Lys Cys Phe Cys Glu Pro Glu Asp
            610                 615                 620
Ile Gln Asp Pro Leu Cys Asp Glu Leu Cys Arg Thr Val Ile Ala Ala
625                 630                 635                 640
Ala Val Leu Phe Ser Phe Ile Val Ser Val Leu Leu Ser Ala Phe Cys
                645                 650                 655
Ile His Cys Tyr His Lys Phe Ala His Lys Pro Pro Ile Ser Ser Ala
                660                 665                 670
Glu Met Thr Phe Arg Arg Pro Ala Gln Ala Phe Pro Val Ser Tyr Ser
            675                 680                 685
Ser Ser Gly Ala Arg Arg Pro Ser Leu Asp Ser Met Glu Asn Gln Val
            690                 695                 700
Ser Val Asp Ala Phe Lys Ile Leu Glu Asp Pro Lys Trp Glu Phe Pro
705                 710                 715                 720
Arg Lys Asn Leu Val Leu Gly Lys Thr Leu Gly Glu Gly Glu Phe Gly
                725                 730                 735
Lys Val Val Lys Ala Thr Ala Phe His Leu Lys Gly Arg Ala Gly Tyr
                740                 745                 750
Thr Thr Val Ala Val Lys Met Leu Lys Glu Asn Ala Ser Pro Ser Glu
                755                 760                 765
Leu Arg Asp Leu Leu Ser Glu Phe Asn Val Leu Lys Gln Val Asn His
770                 775                 780
Pro His Val Ile Lys Leu Tyr Gly Ala Cys Ser Gln Asp Gly Pro Leu
785                 790                 795                 800
Leu Leu Ile Val Glu Tyr Ala Lys Tyr Gly Ser Leu Arg Gly Phe Leu
                805                 810                 815
Arg Glu Ser Arg Lys Val Gly Pro Gly Tyr Leu Gly Ser Gly Gly Ser
            820                 825                 830
Arg Asn Ser Ser Ser Leu Asp His Pro Asp Glu Arg Ala Leu Thr Met
            835                 840                 845
Gly Asp Leu Ile Ser Phe Ala Trp Gln Ile Ser Gln Gly Met Gln Tyr
            850                 855                 860
Leu Ala Glu Met Lys Leu Val His Arg Asp Leu Ala Ala Arg Asn Ile
865                 870                 875                 880
Leu Val Ala Glu Gly Arg Lys Met Lys Ile Ser Asp Phe Gly Leu Ser
                885                 890                 895
```

-continued

```
Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
            915                 920                 925

Thr Thr Gln Ser Asp Val Trp Ser Phe Gly Val Leu Leu Trp Glu Ile
            930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
            995                 1000                1005

Met Val Lys Arg Arg Asp Tyr Leu Asp Leu Ala Ala Ser Thr Pro
        1010                1015                1020

Ser Asp Ser Leu Ile Tyr Asp Asp Gly Leu Ser Glu Glu Glu Thr
        1025                1030                1035

Pro Leu Val Asp Cys Asn Asn Ala Pro Leu Pro Arg Ala Leu Pro
        1040                1045                1050

Ser Thr Trp Ile Glu Asn Lys Leu Tyr Asp Ala Gln His Ser Ser
        1055                1060                1065

Ser Leu Val Gly Ala Ala Phe Gly Lys Ser Gln Gln Leu Phe Trp
        1070                1075                1080

Leu Cys Cys Gln His Cys Asn Phe Ala Glu Lys Ser Arg Ile Thr
        1085                1090                1095

Lys Leu Pro Ala Leu Gln Thr
        1100                1105

<210> SEQ ID NO 18
<211> LENGTH: 1072
<212> TYPE: PRT
<213> ORGANISM: Homo sapiens

<400> SEQUENCE: 18

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65              70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
        130                 135                 140

Val Tyr Phe Ser Phe Phe Asn Thr Ser Phe Pro Ala Cys Ser Ser Leu
```

```
            145                 150                 155                 160
Lys Pro Arg Glu Leu Cys Phe Pro Glu Thr Arg Pro Ser Phe Arg Ile
                    165                 170                 175
Arg Glu Asn Arg Pro Pro Gly Thr Phe His Gln Phe Arg Leu Leu Pro
                180                 185                 190
Val Gln Phe Leu Cys Pro Asn Ile Ser Val Ala Tyr Arg Leu Leu Glu
                195                 200                 205
Gly Glu Gly Leu Pro Phe Arg Cys Ala Pro Asp Ser Leu Glu Val Ser
            210                 215                 220
Thr Arg Trp Ala Leu Asp Arg Glu Gln Arg Glu Lys Tyr Glu Leu Val
225                 230                 235                 240
Ala Val Cys Thr Val His Ala Gly Ala Arg Glu Val Val Met Val
                    245                 250                 255
Pro Phe Pro Val Thr Val Tyr Asp Glu Asp Ser Ala Pro Thr Phe
                    260                 265                 270
Pro Ala Gly Val Asp Thr Ala Ser Ala Val Val Glu Phe Lys Arg Lys
                275                 280                 285
Glu Asp Thr Val Val Ala Thr Leu Arg Val Phe Asp Ala Asp Val Val
            290                 295                 300
Pro Ala Ser Gly Glu Leu Val Arg Arg Tyr Thr Ser Thr Leu Leu Pro
305                 310                 315                 320
Gly Asp Thr Trp Ala Gln Gln Thr Phe Arg Val Glu His Trp Pro Asn
                    325                 330                 335
Glu Thr Ser Val Gln Ala Asn Gly Ser Phe Val Arg Ala Thr Val His
                340                 345                 350
Asp Tyr Arg Leu Val Leu Asn Arg Asn Leu Ser Ile Ser Glu Asn Arg
            355                 360                 365
Thr Met Gln Leu Ala Val Leu Val Asn Asp Ser Asp Phe Gln Gly Pro
            370                 375                 380
Gly Ala Gly Val Leu Leu Leu His Phe Asn Val Ser Val Leu Pro Val
385                 390                 395                 400
Ser Leu His Leu Pro Ser Thr Tyr Ser Leu Ser Val Ser Arg Arg Ala
                    405                 410                 415
Arg Arg Phe Ala Gln Ile Gly Lys Val Cys Val Glu Asn Cys Gln Ala
                420                 425                 430
Phe Ser Gly Ile Asn Val Gln Tyr Lys Leu His Ser Ser Gly Ala Asn
                435                 440                 445
Cys Ser Thr Leu Gly Val Val Thr Ser Ala Glu Asp Thr Ser Gly Ile
            450                 455                 460
Leu Phe Val Asn Asp Thr Lys Ala Leu Arg Arg Pro Lys Cys Ala Glu
465                 470                 475                 480
Leu His Tyr Met Val Val Ala Thr Asp Gln Gln Thr Ser Arg Gln Ala
                    485                 490                 495
Gln Ala Gln Leu Leu Val Thr Val Glu Gly Ser Tyr Val Ala Glu Glu
                500                 505                 510
Ala Gly Cys Pro Leu Ser Cys Ala Val Ser Lys Arg Arg Leu Glu Cys
                515                 520                 525
Glu Glu Cys Gly Gly Leu Gly Ser Pro Thr Gly Arg Cys Glu Trp Arg
            530                 535                 540
Gln Gly Asp Gly Lys Gly Ile Thr Arg Asn Phe Ser Thr Cys Ser Pro
545                 550                 555                 560
Ser Thr Lys Thr Cys Pro Asp Gly His Cys Asp Val Val Glu Thr Gln
                    565                 570                 575
```

-continued

```
Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
            595                 600                 605

Cys Asn Cys Phe Pro Glu Glu Lys Cys Phe Cys Glu Pro Glu Asp
            610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
            675                 680                 685

Ser Ser Gly Ala Arg Arg Pro Ser Leu Asp Ser Met Glu Asn Gln Val
            690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
            755                 760                 765

Leu Arg Asp Leu Leu Ser Glu Phe Asn Val Leu Lys Gln Val Asn His
            770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
            835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
            915                 920                 925

Thr Thr Gln Ser Asp Val Trp Ser Phe Gly Val Leu Leu Trp Glu Ile
            930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990
```

```
Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Arg Ile Ser His Ala
    1055                1060                1065

Phe Thr Arg Phe
    1070

<210> SEQ ID NO 19
<211> LENGTH: 1115
<212> TYPE: PRT
<213> ORGANISM: Mus musculus

<400> SEQUENCE: 19

Met Ala Lys Ala Thr Ser Gly Ala Ala Gly Leu Gly Leu Lys Leu Ile
1               5                   10                  15

Leu Leu Leu Pro Leu Leu Gly Glu Ala Pro Leu Gly Leu Tyr Phe Ser
                20                  25                  30

Arg Asp Ala Tyr Trp Glu Arg Leu Tyr Val Asp Gln Pro Ala Gly Thr
            35                  40                  45

Pro Leu Leu Tyr Val His Ala Leu Arg Asp Ala Pro Gly Glu Val Pro
        50                  55                  60

Ser Phe Arg Leu Gly Gln His Leu Tyr Gly Val Tyr Arg Thr Arg Leu
65                  70                  75                  80

His Glu Asn Asp Trp Ile Arg Ile Asn Glu Thr Thr Gly Leu Leu Tyr
                85                  90                  95

Leu Asn Gln Ser Leu Asp His Ser Ser Trp Glu Gln Leu Ser Ile Arg
                100                 105                 110

Asn Gly Gly Phe Pro Leu Leu Thr Ile Phe Leu Gln Val Phe Leu Gly
            115                 120                 125

Ser Thr Ala Gln Arg Glu Gly Glu Cys His Trp Pro Gly Cys Thr Arg
        130                 135                 140

Val Tyr Phe Ser Phe Ile Asn Asp Thr Phe Pro Asn Cys Ser Ser Phe
145                 150                 155                 160

Lys Ala Gln Asp Leu Cys Ile Pro Glu Thr Ala Val Ser Phe Arg Val
                165                 170                 175

Arg Glu Asn Arg Pro Pro Gly Thr Phe Tyr His Phe His Met Leu Pro
                180                 185                 190

Val Gln Phe Leu Cys Pro Asn Ile Ser Val Lys Tyr Ser Leu Leu Gly
            195                 200                 205

Gly Asp Ser Leu Pro Phe Arg Cys Asp Pro Asp Cys Leu Glu Val Ser
        210                 215                 220

Thr Arg Trp Ala Leu Asp Arg Glu Leu Arg Glu Lys Tyr Val Leu Glu
225                 230                 235                 240

Ala Leu Cys Ile Val Ala Gly Pro Gly Ala Asn Lys Glu Thr Val Thr
                245                 250                 255

Leu Ser Phe Pro Val Thr Val Tyr Asp Glu Asp Asp Ser Ala Pro Thr
                260                 265                 270

Phe Ser Gly Gly Val Gly Thr Ala Ser Ala Val Val Glu Phe Lys Arg
            275                 280                 285
```

```
Lys Glu Gly Thr Val Val Ala Thr Leu Gln Val Phe Asp Ala Asp Val
290                 295                 300

Val Pro Ala Ser Gly Glu Leu Val Arg Arg Tyr Thr Asn Thr Leu Leu
305                 310                 315                 320

Ser Gly Asp Ser Trp Ala Gln Gln Thr Phe Arg Val Glu His Ser Pro
                325                 330                 335

Ile Glu Thr Leu Val Gln Val Asn Asn Asn Ser Val Arg Ala Thr Met
            340                 345                 350

His Asn Tyr Lys Leu Ile Leu Asn Arg Ser Leu Ser Ile Ser Glu Ser
        355                 360                 365

Arg Val Leu Gln Leu Ala Val Leu Val Asn Asp Ser Asp Phe Gln Gly
    370                 375                 380

Pro Gly Ala Gly Gly Ile Leu Val Leu His Phe Asn Val Ser Val Leu
385                 390                 395                 400

Pro Val Thr Leu Asn Leu Pro Arg Ala Tyr Ser Phe Pro Val Asn Lys
                405                 410                 415

Arg Ala Arg Arg Tyr Ala Gln Ile Gly Lys Val Cys Val Glu Asn Cys
                420                 425                 430

Gln Glu Phe Ser Gly Val Ser Ile Gln Tyr Lys Leu Gln Pro Ser Ser
            435                 440                 445

Ile Asn Cys Thr Ala Leu Gly Val Val Thr Ser Pro Glu Asp Thr Ser
450                 455                 460

Gly Thr Leu Phe Val Asn Asp Thr Glu Ala Leu Arg Arg Pro Glu Cys
465                 470                 475                 480

Thr Lys Leu Gln Tyr Thr Val Val Ala Thr Asp Arg Gln Thr Arg Arg
                485                 490                 495

Gln Thr Gln Ala Ser Leu Val Val Thr Val Glu Gly Thr Ser Ile Thr
            500                 505                 510

Glu Glu Val Gly Cys Pro Lys Ser Cys Ala Val Asn Lys Arg Arg Pro
        515                 520                 525

Glu Cys Glu Glu Cys Gly Gly Leu Gly Ser Pro Thr Gly Arg Cys Glu
    530                 535                 540

Trp Arg Gln Gly Asp Gly Lys Gly Ile Thr Arg Asn Phe Ser Thr Cys
545                 550                 555                 560

Ser Pro Ser Thr Arg Thr Cys Pro Asp Gly His Cys Asp Ala Val Glu
                565                 570                 575

Ser Arg Asp Ala Asn Ile Cys Pro Gln Asp Cys Leu Arg Ala Asp Ile
                580                 585                 590

Val Gly Gly His Glu Arg Gly Glu Arg Gln Gly Ile Lys Ala Gly Tyr
            595                 600                 605

Gly Ile Cys Asn Cys Phe Pro Asp Glu Lys Lys Cys Phe Cys Glu Pro
        610                 615                 620

Glu Asp Ser Gln Gly Pro Leu Cys Asp Ala Leu Cys Arg Thr Ile Ile
625                 630                 635                 640

Thr Ala Ala Leu Phe Ser Leu Ile Ile Ser Ile Leu Leu Ser Ile Phe
                645                 650                 655

Cys Val Cys His His Lys His Gly His Lys Pro Pro Ile Ala Ser
                660                 665                 670

Ala Glu Met Thr Phe Cys Arg Pro Ala Gln Gly Phe Pro Ile Ser Tyr
            675                 680                 685

Ser Ser Ser Gly Thr Arg Arg Pro Ser Leu Asp Ser Thr Glu Asn Gln
        690                 695                 700
```

```
Val Pro Val Asp Ser Phe Lys Ile Pro Glu Asp Pro Lys Trp Glu Phe
705                 710                 715                 720

Pro Arg Lys Asn Leu Val Leu Gly Lys Thr Leu Gly Glu Gly Glu Phe
                725                 730                 735

Gly Lys Val Val Lys Ala Thr Ala Phe Arg Leu Lys Gly Arg Ala Gly
            740                 745                 750

Tyr Thr Thr Val Ala Val Lys Met Leu Lys Glu Asn Ala Ser Gln Ser
        755                 760                 765

Glu Leu Arg Asp Leu Leu Ser Glu Phe Asn Leu Leu Lys Gln Val Asn
    770                 775                 780

His Pro His Val Ile Lys Leu Tyr Gly Ala Cys Ser Gln Asp Gly Pro
785                 790                 795                 800

Leu Leu Leu Ile Val Glu Tyr Ala Lys Tyr Gly Ser Leu Arg Gly Phe
                805                 810                 815

Leu Arg Asp Ser Arg Lys Ile Gly Pro Ala Tyr Val Ser Gly Gly Gly
            820                 825                 830

Ser Arg Asn Ser Ser Ser Leu Asp His Pro Asp Glu Arg Val Leu Thr
        835                 840                 845

Met Gly Asp Leu Ile Ser Phe Ala Trp Gln Ile Ser Arg Gly Met Gln
850                 855                 860

Tyr Leu Ala Glu Met Lys Leu Val His Arg Asp Leu Ala Ala Arg Asn
865                 870                 875                 880

Ile Leu Val Ala Glu Gly Arg Lys Met Lys Ile Ser Asp Phe Gly Leu
                885                 890                 895

Ser Arg Asp Val Tyr Glu Glu Asp Ser Tyr Val Lys Lys Ser Lys Gly
            900                 905                 910

Arg Ile Pro Val Lys Trp Met Ala Ile Glu Ser Leu Phe Asp His Ile
        915                 920                 925

Tyr Thr Thr Gln Ser Asp Val Trp Ser Phe Gly Val Leu Leu Trp Glu
    930                 935                 940

Ile Val Thr Leu Gly Gly Asn Pro Tyr Pro Gly Ile Pro Pro Glu Arg
945                 950                 955                 960

Leu Phe Asn Leu Leu Lys Thr Gly His Arg Met Glu Arg Pro Asp Asn
                965                 970                 975

Cys Ser Glu Glu Met Tyr Arg Leu Met Leu Gln Cys Trp Lys Gln Glu
            980                 985                 990

Pro Asp Lys Arg Pro Val Phe Ala Asp Ile Ser Lys Asp Leu Glu Lys
        995                 1000                1005

Met Met Val Lys Ser Arg Asp Tyr Leu Asp Leu Ala Ala Ser Thr
1010                1015                1020

Pro Ser Asp Ser Leu Leu Tyr Asp Asp Gly Leu Ser Glu Glu Glu
1025                1030                1035

Thr Pro Leu Val Asp Cys Asn Asn Ala Pro Leu Pro Arg Ser Leu
1040                1045                1050

Pro Ser Thr Trp Ile Glu Asn Lys Leu Tyr Gly Met Ser Asp Pro
1055                1060                1065

Asn Trp Pro Gly Glu Ser Pro Val Pro Leu Thr Arg Ala Asp Gly
1070                1075                1080

Thr Ser Thr Gly Phe Pro Arg Tyr Ala Asn Asp Ser Val Tyr Ala
1085                1090                1095

Asn Trp Met Val Ser Pro Ser Ala Ala Lys Leu Met Asp Thr Phe
1100                1105                1110

Asp Ser
```

1115

<210> SEQ ID NO 20
<211> LENGTH: 394
<212> TYPE: PRT
<213> ORGANISM: Macaca fascicularis

<400> SEQUENCE: 20

Met Ile Val Leu Ile Phe Leu Ala Leu Gly Leu Ser Leu Glu Asn Glu
1               5                   10                  15

Tyr Thr Ser Gln Thr Asn Asn Cys Thr Tyr Leu Arg Glu Gln Cys Leu
            20                  25                  30

His Asp Ala Asn Gly Cys Lys His Ala Trp Arg Ile Met Glu Asp Ala
        35                  40                  45

Cys Asn Asp Ser Asp Pro Gly Asp Pro Cys Lys Met Asn Asn Ser Ser
    50                  55                  60

Tyr Cys Asn Leu Ser Ile Gln Tyr Leu Val Glu Ser Asn Phe Arg Phe
65                  70                  75                  80

Lys Glu Cys Leu Cys Thr Asp Asp Phe Tyr Cys Thr Val Asn Lys Leu
                85                  90                  95

Leu Gly Lys Glu Cys Val Asn Lys Ser Asp Asn Met Arg Glu Asp Lys
            100                 105                 110

Phe Lys Trp Asn Leu Thr Thr His Ser His Gly Phe Lys Gly Met
        115                 120                 125

Trp Ser Cys Leu Glu Val Ala Glu Ala Cys Val Gly Asp Val Val Cys
130                 135                 140

Asn Ala Gln Leu Ala Ser Tyr Leu Lys Ala Cys Ser Ala Asn Gly Asn
145                 150                 155                 160

Pro Cys Asp Val Lys His Cys Gln Ala Ala Ile Arg Phe Phe Tyr Gln
                165                 170                 175

Asn Ile Pro Phe Asn Ile Ala Gln Met Leu Ala Phe Cys Asp Cys Ser
            180                 185                 190

Gln Ser Asp Ile Pro Cys Gln Gln Ser Lys Glu Ala Leu His Ser Lys
        195                 200                 205

Pro Cys Ala Leu Asn Met Val Pro Pro Thr Cys Leu Asn Val Ile
    210                 215                 220

Arg Ser Cys Gln Asn Asp Glu Leu Cys Arg Arg His Tyr Arg Thr Phe
225                 230                 235                 240

Gln Ser Lys Cys Trp Gln Arg Val Thr Arg Lys Cys His Glu Asp Glu
                245                 250                 255

Asn Cys Ile Ser Ala Leu Ser Lys Gln Asp Leu Thr Cys Ser Gly Ser
            260                 265                 270

Asp Asp Cys Lys Ala Ala Tyr Ile Asp Ile Leu Gly Thr Val Leu Gln
        275                 280                 285

Val Gln Cys Asn Cys Arg Thr Ile Thr Gln Ser Glu Glu Ser Leu Cys
    290                 295                 300

Lys Ile Phe Gln His Met Leu His Arg Lys Ser Cys Phe Asn Tyr Pro
305                 310                 315                 320

Thr Leu Ser Asn Val Lys Ser Met Ala Leu Tyr Thr Arg Lys His Thr
                325                 330                 335

Asn Lys Ile Thr Leu Thr Gly Phe Gln Ser Pro Phe Asn Gly Glu Val
            340                 345                 350

Ile Tyr Ala Ala Met Cys Met Thr Val Thr Cys Gly Ile Leu Leu Leu
        355                 360                 365

Val Met Val Lys Leu Arg Thr Ser Arg Ile Ser Ser Lys Ala Arg Asp
370                 375                 380

Pro Ser Leu Ser Gln Val Pro Gly Glu Leu
385                 390

<210> SEQ ID NO 21
<211> LENGTH: 1117
<212> TYPE: PRT
<213> ORGANISM: Macaca fascicularis

<400> SEQUENCE: 21

Met Ala Lys Ala Thr Ser Gly Ala Ala Gly Leu Arg Leu Leu Leu Leu
1               5                   10                  15

Leu Leu Leu Leu Leu Pro Leu Leu Gly Lys Val Ala Leu Gly Leu
                20                  25                  30

Tyr Phe Ser Arg Asp Ala Tyr Trp Glu Lys Leu Tyr Val Asp Gln Pro
            35                  40                  45

Ala Gly Thr Pro Leu Leu Tyr Val His Ala Leu Arg Asp Ala Pro Glu
        50                  55                  60

Glu Val Pro Ser Phe Arg Leu Gly Gln His Leu Tyr Gly Thr Tyr Arg
65                  70                  75                  80

Thr Arg Leu His Glu Asn Asn Trp Ile Cys Ile Gln Glu Asp Thr Gly
                85                  90                  95

Leu Leu Tyr Leu Asn Arg Ser Leu Asp Arg Ser Ser Trp Glu Lys Leu
            100                 105                 110

Ser Gly Arg Asn Arg Gly Phe Pro Leu Leu Thr Val Tyr Leu Lys Val
        115                 120                 125

Phe Leu Ser Pro Thr Ser Leu Arg Glu Gly Glu Cys Gln Trp Pro Gly
130                 135                 140

Cys Ala Arg Val Tyr Phe Ser Phe Phe Asn Thr Ser Phe Pro Ala Cys
145                 150                 155                 160

Thr Ser Leu Lys Pro Arg Glu Leu Cys Phe Pro Glu Thr Arg Pro Ser
                165                 170                 175

Phe Arg Ile Arg Glu Asn Arg Pro Pro Gly Thr Phe His Gln Phe Arg
            180                 185                 190

Leu Leu Pro Val Gln Phe Leu Cys Pro Asn Ile Ser Val Ala Tyr Arg
        195                 200                 205

Leu Leu Glu Gly Glu Gly Leu Pro Phe Arg Cys Ala Pro Asp Ser Leu
    210                 215                 220

Glu Val Ser Thr Arg Trp Ala Leu Asp Arg Glu Gln Arg Glu Lys Tyr
225                 230                 235                 240

Glu Leu Val Ala Val Cys Thr Val His Ala Gly Ala Arg Glu Glu Val
                245                 250                 255

Val Met Val Pro Phe Pro Val Thr Val Tyr Asp Glu Asp Asp Ser Ala
            260                 265                 270

Pro Thr Phe Pro Ala Gly Val Asp Thr Ala Ser Ala Val Val Glu Phe
        275                 280                 285

Lys Arg Lys Glu Asp Thr Val Val Ala Thr Leu Arg Val Phe Asp Ala
    290                 295                 300

Asp Val Val Pro Ala Ser Gly Glu Leu Val Arg Arg Tyr Thr Ser Thr
305                 310                 315                 320

Leu Leu Pro Gly Asp Thr Trp Thr Gln Gln Thr Phe Arg Val Glu His
                325                 330                 335

Trp Pro Asn Glu Thr Ser Val Gln Ala Asn Gly Ser Phe Val Arg Ala
            340                 345                 350

-continued

Thr Val His Asp Tyr Arg Leu Val Leu Asn Arg Asn Leu Ser Ile Ser
              355                 360                 365

Glu Asn Arg Thr Met Gln Leu Ala Val Leu Val Asn Asp Ser Asp Phe
    370                 375                 380

Gln Gly Pro Gly Ala Gly Val Leu Leu Leu His Phe Asn Val Ser Val
385                 390                 395                 400

Leu Pro Val Ser Leu His Leu Pro Ser Ser Tyr Ser Leu Ser Val Ser
                405                 410                 415

Arg Arg Ala Arg Arg Phe Ala Gln Ile Gly Lys Val Cys Val Glu Asn
                420                 425                 430

Cys Gln Ala Phe Ser Gly Ile Asn Val Gln Tyr Glu Leu His Ser Ser
                435                 440                 445

Gly Ala Asn Cys Ser Thr Leu Gly Val Val Thr Ser Ala Glu Asp Thr
    450                 455                 460

Ser Gly Ile Leu Phe Val Asn Asp Thr Lys Ala Leu Arg Arg Pro Lys
465                 470                 475                 480

Cys Ala Glu Leu His Tyr Met Val Val Ala Thr Asn His Gln Thr Ser
                485                 490                 495

Arg Gln Ala Gln Ala Gln Leu Leu Val Thr Val Glu Gly Leu Tyr Val
                500                 505                 510

Ala Glu Glu Ala Gly Cys Pro Leu Ser Cys Ala Val Ser Lys Arg Arg
                515                 520                 525

Pro Glu Cys Glu Glu Cys Gly Gly Leu Gly Ser Pro Thr Gly Arg Cys
    530                 535                 540

Glu Trp Arg Gln Gly Asp Gly Lys Gly Ile Thr Arg Asn Phe Ser Thr
545                 550                 555                 560

Cys Ser Pro Ser Thr Lys Thr Cys Pro Asp Gly His Cys Asp Val Val
                565                 570                 575

Glu Thr Gln Asp Ile Asn Ile Cys Pro Gln Asp Cys Leu Arg Gly Ser
                580                 585                 590

Ile Val Gly Gly His Glu Pro Gly Glu Pro Arg Gly Ile Lys Ala Gly
                595                 600                 605

Tyr Gly Thr Cys Asn Cys Phe Pro Glu Glu Lys Cys Phe Cys Glu
    610                 615                 620

Pro Glu Asp Ile Gln Asp Pro Leu Cys Asp Glu Leu Cys Arg Thr Val
625                 630                 635                 640

Ile Ala Ala Val Leu Phe Ser Phe Ile Val Ser Val Leu Leu Ser
                645                 650                 655

Ala Phe Cys Ile His Arg Tyr His Lys Phe Ala His Lys Pro Pro Ile
                660                 665                 670

Pro Ser Ala Glu Met Thr Phe Arg Arg Pro Ala Gln Ala Phe Pro Val
                675                 680                 685

Ser Tyr Ser Ser Ser Gly Ala Arg Arg Pro Ser Leu Asp Ser Met Glu
    690                 695                 700

Asn Gln Val Ser Val Asp Ala Phe Lys Ile Pro Glu Asp Pro Lys Trp
705                 710                 715                 720

Glu Phe Pro Arg Lys Asn Leu Val Leu Gly Lys Thr Leu Gly Glu Gly
                725                 730                 735

Glu Phe Gly Lys Val Val Lys Ala Thr Ala Phe Arg Leu Lys Gly Arg
                740                 745                 750

Ala Gly Tyr Thr Thr Val Ala Val Lys Met Leu Lys Glu Asn Ala Ser
                755                 760                 765

```
Pro Ser Glu Leu Arg Asp Leu Leu Ser Glu Phe Asn Leu Leu Lys Gln
770                 775                 780

Val Asn His Pro His Val Ile Lys Leu Tyr Gly Ala Cys Ser Gln Asp
785                 790                 795                 800

Gly Pro Leu Leu Leu Ile Val Glu Tyr Ala Lys Tyr Gly Ser Leu Arg
                805                 810                 815

Gly Phe Leu Arg Glu Ser Arg Lys Val Gly Pro Gly Tyr Leu Gly Ser
            820                 825                 830

Gly Gly Ser Arg Asn Ser Ser Leu Asp His Pro Asp Glu Arg Ala
        835                 840                 845

Leu Thr Met Gly Asp Leu Ile Ser Phe Ala Trp Gln Ile Ser Arg Gly
850                 855                 860

Met Gln Tyr Leu Ala Glu Met Lys Leu Val His Arg Asp Leu Ala Ala
865                 870                 875                 880

Arg Asn Ile Leu Val Ala Glu Gly Arg Lys Met Lys Ile Ser Asp Phe
                885                 890                 895

Gly Leu Ser Arg Asp Val Tyr Glu Glu Asp Ser Tyr Val Lys Arg Ser
            900                 905                 910

Lys Gly Arg Ile Pro Val Lys Trp Met Ala Ile Glu Ser Leu Phe Asp
        915                 920                 925

His Ile Tyr Thr Thr Gln Ser Asp Val Trp Ser Phe Gly Val Leu Leu
930                 935                 940

Trp Glu Ile Val Thr Leu Gly Gly Asn Pro Tyr Pro Gly Ile Pro Pro
945                 950                 955                 960

Glu Arg Leu Phe Asn Leu Leu Lys Thr Gly His Arg Met Glu Arg Pro
                965                 970                 975

Asp Asn Cys Ser Glu Glu Met Tyr Arg Leu Met Leu Gln Cys Trp Lys
            980                 985                 990

Gln Glu Pro Asp Lys Arg Pro Val Phe Ala Asp Ile Ser Lys Asp Leu
        995                 1000                1005

Glu Lys Met Met Val Lys Ser Arg Asp Tyr Leu Asp Leu Ala Ala
    1010                1015                1020

Ser Thr Pro Ser Asp Ser Leu Leu Tyr Asp Asp Gly Leu Ser Glu
    1025                1030                1035

Glu Glu Thr Pro Leu Val Asp Cys Asn Asn Ala Pro Leu Pro Arg
    1040                1045                1050

Ala Leu Pro Ser Thr Trp Ile Glu Asn Lys Leu Tyr Gly Met Ser
    1055                1060                1065

Asp Pro Asn Trp Pro Gly Glu Ser Pro Val Pro Leu Thr Arg Ala
    1070                1075                1080

Asp Gly Thr Asn Thr Gly Phe Pro Arg Tyr Ala Asn Asp Ser Val
    1085                1090                1095

Tyr Ala Asn Trp Met Leu Ser Pro Ser Ala Ala Lys Leu Met Asp
    1100                1105                1110

Thr Phe Asp Ser
    1115

<210> SEQ ID NO 22
<211> LENGTH: 394
<212> TYPE: PRT
<213> ORGANISM: Rattus norvegicus

<400> SEQUENCE: 22

Met Leu Val Phe Ile Phe Leu Ala Val Arg Leu Ser Ser Glu Asn Glu
1               5                   10                  15
```

-continued

Ser Ser Ser Gln Thr Asn Asp Cys Ala Tyr Phe Met Arg Gln Cys Leu
            20                  25                  30

Thr Asp Thr Asp Gly Cys Lys Gln Ser Trp Arg Ser Met Glu Asp Ala
            35                  40                  45

Cys Leu Val Ser Gly Asp Ser Cys Lys Ile Asn Asn Pro Leu Pro Cys
 50                  55                  60

Asn Leu Ser Ile Gln Ser Leu Val Glu Lys His Phe Gln Phe Lys Gly
 65                  70                  75                  80

Cys Leu Cys Thr Asp Asp Leu His Cys Thr Val Asn Lys Ile Phe Gly
                85                  90                  95

Lys Lys Cys Thr Asn Lys Thr Asp Ser Met Lys Lys Asp Asn Lys Tyr
            100                 105                 110

Lys Arg Asn Leu Thr Thr Pro Leu Tyr His Asp Thr Gly Phe Lys Gln
            115                 120                 125

Met Gln Ser Cys Leu Glu Val Thr Glu Ala Cys Val Gly Asp Val Val
130                 135                 140

Cys Asn Ala Gln Leu Ala Leu Tyr Leu Lys Ala Cys Thr Ala Asn Gly
145                 150                 155                 160

Asn Leu Cys Asp Val Lys His Cys Gln Ala Ala Ile Arg Phe Phe Tyr
                165                 170                 175

Gln Asn Met Pro Phe Asn Thr Ala Gln Met Leu Ala Phe Cys Asp Cys
            180                 185                 190

Ala Gln Ser Asp Ile Pro Cys Gln Gln Ser Lys Glu Thr Leu His Ser
            195                 200                 205

Lys Pro Cys Ala Leu Asn Val Val Pro Pro Thr Cys Leu Ser Val
    210                 215                 220

Ile His Thr Cys Arg Asn Asp Glu Leu Cys Arg Thr Tyr Tyr Arg Thr
225                 230                 235                 240

Phe Gln Thr Glu Cys Trp Pro His Val Ala Gly Lys Cys Arg Glu Asp
                245                 250                 255

Glu Thr Cys Ile Ser Met Leu Gly Lys Gln Asp Leu Thr Cys Ser Gly
            260                 265                 270

Ser Asp Ser Cys Arg Ala Ala Tyr Leu Gly Thr Phe Gly Thr Val Leu
            275                 280                 285

Gln Val Pro Cys Ala Cys Arg Ser Ile Thr Gln Gly Glu Glu Pro Leu
            290                 295                 300

Cys Met Ala Phe Gln His Met Leu His Ser Lys Ser Cys Phe Asn Tyr
305                 310                 315                 320

Pro Thr Pro Asn Val Lys Asp Ile Ser Ser Tyr Glu Arg Lys His Ser
                325                 330                 335

Lys Glu Ile Thr Leu Thr Gly Phe Asn Ser Pro Phe Ser Gly Glu Leu
            340                 345                 350

Ile Tyr Val Val Cys Met Val Thr Ser Gly Ile Leu Ser Leu
            355                 360                 365

Val Met Leu Lys Leu Arg Ile Pro Ser Lys Lys Arg Asp Pro Ala Pro
        370                 375                 380

Ile Glu Ile Ala Gly Ala Val Ile Ile Gln
385                 390

<210> SEQ ID NO 23
<211> LENGTH: 1115
<212> TYPE: PRT
<213> ORGANISM: Rattus norvegicus

```
<400> SEQUENCE: 23

Met Ala Lys Ala Arg Ser Gly Ala Ala Gly Leu Gly Leu Lys Leu Phe
1               5                   10                  15

Leu Leu Leu Pro Leu Leu Gly Glu Ala Pro Leu Gly Leu Tyr Phe Ser
            20                  25                  30

Arg Asp Ala Tyr Trp Glu Arg Leu Tyr Val Asp Gln Pro Ala Gly Thr
        35                  40                  45

Pro Leu Leu Tyr Val His Ala Leu Arg Asp Ala Pro Gly Glu Val Pro
    50                  55                  60

Ser Phe Arg Leu Gly Gln Tyr Leu Tyr Gly Val Tyr Arg Thr Arg Leu
65                  70                  75                  80

His Glu Asn Asp Trp Ile His Ile Asp Ser Gly Thr Gly Leu Leu Tyr
                85                  90                  95

Leu Asn Gln Ser Leu Asp His Ser Ser Trp Glu Gln Leu Ser Ile Arg
            100                 105                 110

Asn Gly Gly Phe Pro Leu Leu Thr Val Phe Leu Gln Val Phe Leu Gly
        115                 120                 125

Ser Thr Ala Gln Arg Glu Gly Glu Cys His Trp Pro Gly Cys Ala Arg
    130                 135                 140

Val Tyr Phe Ser Phe Ile Asn Asp Thr Phe Pro Asn Cys Ser Ser Phe
145                 150                 155                 160

Lys Ala Arg Asp Leu Cys Thr Pro Glu Thr Gly Val Ser Phe Arg Ile
                165                 170                 175

Arg Glu Asn Arg Pro Pro Gly Thr Phe Tyr Gln Phe Arg Met Leu Pro
            180                 185                 190

Val Gln Phe Leu Cys Pro Asn Ile Ser Val Lys Tyr Lys Leu Leu Glu
        195                 200                 205

Gly Asp Gly Leu Pro Phe Arg Cys Asp Pro Asp Cys Leu Glu Val Ser
    210                 215                 220

Thr Arg Trp Ala Leu Asp Arg Glu Leu Gln Glu Lys Tyr Val Leu Glu
225                 230                 235                 240

Ala Glu Cys Ala Val Ala Gly Pro Gly Ala Asn Lys Glu Lys Val Ala
                245                 250                 255

Val Ser Phe Pro Val Thr Val Tyr Asp Glu Asp Ser Pro Pro Thr
            260                 265                 270

Phe Ser Gly Gly Val Gly Thr Ala Ser Ala Val Glu Phe Lys Arg
        275                 280                 285

Lys Glu Gly Thr Val Val Ala Thr Leu Gln Val Phe Asp Ala Asp Val
    290                 295                 300

Val Pro Ala Ser Gly Glu Leu Val Arg Arg Tyr Thr Ser Thr Leu Leu
305                 310                 315                 320

Ser Gly Asp Ser Trp Ala Gln Gln Thr Phe Arg Val Glu His Thr Pro
                325                 330                 335

Asn Glu Thr Leu Val Gln Ser Asn Asn Ser Val Arg Ala Thr Met
            340                 345                 350

His Asn Tyr Lys Leu Val Leu Asn Arg Ser Leu Ser Ile Ser Glu Ser
            355                 360                 365

Arg Val Leu Gln Leu Val Leu Val Asn Asp Ser Asp Phe Gln Gly
    370                 375                 380

Pro Gly Ser Gly Val Leu Phe Leu His Phe Asn Val Ser Val Leu Pro
385                 390                 395                 400

Val Thr Leu Asn Leu Pro Met Ala Tyr Ser Phe Pro Val Asn Arg Arg
                405                 410                 415
```

```
Ala Arg Arg Tyr Ala Gln Ile Gly Lys Val Cys Val Glu Asn Cys Gln
            420                 425                 430

Glu Phe Ser Gly Val Ser Ile Gln Tyr Lys Leu Gln Pro Ser Ser Thr
            435                 440                 445

Asn Cys Ser Ala Leu Gly Val Val Thr Ser Thr Glu Asp Thr Ser Gly
            450                 455                 460

Thr Leu Tyr Val Asn Asp Thr Glu Ala Leu Arg Arg Pro Glu Cys Thr
465                 470                 475                 480

Glu Leu Gln Tyr Thr Val Val Ala Thr Asp Arg Gln Thr Arg Arg Gln
                485                 490                 495

Thr Gln Ala Ser Leu Val Val Thr Val Glu Gly Thr Tyr Ile Ala Glu
            500                 505                 510

Glu Val Gly Cys Pro Lys Ser Cys Ala Val Asn Lys Arg Arg Pro Glu
            515                 520                 525

Cys Glu Glu Cys Gly Gly Leu Gly Ser Pro Thr Gly Arg Cys Glu Trp
            530                 535                 540

Arg Gln Gly Asp Gly Lys Gly Ile Thr Arg Asn Phe Ser Thr Cys Ser
545                 550                 555                 560

Pro Ser Thr Arg Thr Cys Pro Asp Gly His Cys Asp Ala Leu Glu Ser
                565                 570                 575

Arg Asp Ile Asn Ile Cys Pro Gln Asp Cys Leu Arg Gly Pro Ile Val
            580                 585                 590

Gly Gly His Glu Arg Gly Glu Arg Gln Gly Ile Lys Ala Gly Tyr Gly
            595                 600                 605

Ile Cys Asn Cys Phe Pro Asp Glu Lys Lys Cys Phe Cys Glu Pro Glu
            610                 615                 620

Asp Ser Gln Gly Pro Leu Cys Asp Glu Leu Cys Arg Thr Val Ile Thr
625                 630                 635                 640

Ala Ala Val Leu Phe Ser Phe Ile Ile Ser Val Leu Leu Ser Thr Phe
                645                 650                 655

Cys Ile His Arg Tyr His Lys His Ala His Lys Pro Pro Ile Ala Ser
            660                 665                 670

Ala Glu Met Thr Phe Cys Arg Pro Ala Gln Gly Phe Pro Ile Ser Tyr
            675                 680                 685

Ser Ser Ser Gly Thr Arg Arg Pro Ser Leu Asp Ser Met Glu Asn Gln
            690                 695                 700

Val Ser Val Asp Ser Phe Lys Ile Pro Glu Asp Pro Lys Trp Glu Phe
705                 710                 715                 720

Pro Arg Lys Asn Leu Val Leu Gly Lys Thr Leu Gly Glu Gly Glu Phe
            725                 730                 735

Gly Lys Val Val Lys Ala Thr Ala Phe Arg Leu Lys Gly Arg Ala Gly
            740                 745                 750

Tyr Thr Thr Val Ala Val Lys Met Leu Lys Glu Asn Ala Ser Gln Ser
            755                 760                 765

Glu Leu Arg Asp Leu Leu Ser Glu Phe Asn Leu Leu Lys Gln Val Asn
            770                 775                 780

His Pro His Val Ile Lys Leu Tyr Gly Ala Cys Ser Gln Asp Gly Pro
785                 790                 795                 800

Leu Leu Leu Ile Val Glu Tyr Ala Lys Tyr Gly Ser Leu Arg Gly Phe
                805                 810                 815

Leu Arg Asp Ser Arg Lys Ile Gly Pro Ala Tyr Val Ser Gly Gly
            820                 825                 830
```

-continued

```
Ser Arg Asn Ser Ser Ser Leu Asp His Pro Asp Glu Arg Val Leu Thr
        835                 840                 845

Met Gly Asp Leu Ile Ser Phe Ala Trp Gln Ile Ser Arg Gly Met Gln
850                     855                 860

Tyr Leu Ala Glu Met Lys Leu Val His Arg Asp Leu Ala Ala Arg Asn
865                 870                 875                 880

Ile Leu Val Ala Glu Gly Arg Lys Met Lys Ile Ser Asp Phe Gly Leu
                885                 890                 895

Ser Arg Asp Val Tyr Glu Glu Asp Ser Tyr Val Lys Lys Ser Lys Gly
            900                 905                 910

Arg Ile Pro Val Lys Trp Met Ala Ile Glu Ser Leu Phe Asp His Ile
        915                 920                 925

Tyr Thr Thr Gln Ser Asp Val Trp Ser Phe Gly Val Leu Leu Trp Glu
930                 935                 940

Ile Val Thr Leu Gly Gly Asn Pro Tyr Pro Gly Ile Pro Pro Glu Arg
945                 950                 955                 960

Leu Phe Asn Leu Leu Lys Thr Gly His Arg Met Glu Arg Pro Asp Asn
                965                 970                 975

Cys Ser Glu Glu Met Tyr Arg Leu Met Leu Gln Cys Trp Lys Gln Glu
            980                 985                 990

Pro Asp Lys Arg Pro Val Phe Ala Asp Ile Ser Lys Asp Leu Glu Lys
        995                 1000                1005

Met Met Val Lys Ser Arg Asp Tyr Leu Asp Leu Ala Ala Ser Thr
        1010                1015                1020

Pro Ser Asp Ser Leu Leu Tyr Asp Asp Gly Leu Ser Glu Glu Glu
    1025                1030                1035

Thr Pro Leu Val Asp Cys Asn Ser Ala Pro Leu Pro Arg Ser Leu
    1040                1045                1050

Pro Ser Thr Trp Ile Glu Asn Lys Leu Tyr Gly Met Ser Asp Pro
    1055                1060                1065

Asn Trp Pro Gly Glu Ser Pro Val Pro Leu Thr Arg Ala Asp Gly
    1070                1075                1080

Thr Ser Thr Gly Phe Pro Arg Tyr Ala Asn Asp Ser Val Tyr Ala
    1085                1090                1095

Asn Trp Met Val Ser Pro Ser Ala Ala Lys Leu Met Asp Thr Phe
    1100                1105                1110

Asp Ser
1115
```